US008017313B2

(12) United States Patent
Adams et al.

(10) Patent No.: US 8,017,313 B2
(45) Date of Patent: Sep. 13, 2011

(54) HUMAN G PROTEIN-COUPLED RECEPTOR AND MODULATORS THEREOF FOR THE TREATMENT OF CARDIOVASCULAR DISORDERS

(75) Inventors: John W. Adams, San Diego, CA (US); Daniel T. Connolly, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 401 days.

(21) Appl. No.: 10/561,132

(22) PCT Filed: Jun. 17, 2004

(86) PCT No.: PCT/US2004/019574
§ 371 (c)(1),
(2), (4) Date: Feb. 23, 2007

(87) PCT Pub. No.: WO2005/003786
PCT Pub. Date: Jan. 13, 2005

(65) Prior Publication Data
US 2007/0231792 A1 Oct. 4, 2007

Related U.S. Application Data

(60) Provisional application No. 60/480,046, filed on Jun. 20, 2003.

(51) Int. Cl.
*C12Q 1/00* (2006.01)
*C07K 14/705* (2006.01)

(52) U.S. Cl. .......................................... 435/4; 530/350

(58) Field of Classification Search ........................ None
See application file for complete search history.

(56) References Cited

U.S. PATENT DOCUMENTS 7,049,096 B2 * 5/2006 Feder et al. ................. 435/69.1
2002/0146692 A1 10/2002 Yamazaki et al.

FOREIGN PATENT DOCUMENTS

WO   WO 02/28898 A2    4/2002
WO   WO 2004/040000 A2  5/2004

OTHER PUBLICATIONS

Ji et al., G protein-coupled receptors. J. Biol. Chem. 273:17299-17302, 1998.*
Abe J et al: "Ig-Hepta, a novel member of the G protein-coupled hepta-helical receptor (GPCR) family that has immunoglobulin-like . . . ", J Biol Chem (1999) 274:19957-19964.
Adams JW et al: "G-proteins in growth and apoptosis: lessons from the heart," Oncogene (2001) 20:1626-1634.
Akal-Strader et al, Residues in the first extracellular loop of a G protein-coupled receptor play a role in signal transduction. J Biol Chem. 2002 277:30581-90.
Bai et al, Structure and function of the extracellular calcium-sensing receptor. Int J Mol Med. 1999 4:115-25 (Review).
Califano SPLASH: structural pattern localization analysis by sequential histograms. Bioinformatics. 2000 16:341-57.
Chollet et al, Biophysical approaches to G protein-coupled receptors: structure, function and dynamics. J Comput Aided Mol Des. 1999 13:209-19 (Review).
Chung DA et al, Mutagenesis and peptide analysis of the DRY motif in the alpha2A adrenergic receptor: evidence for alternate mechanisms in G protein-coupled receptors. Biochem Biophys Res Commun. 2002 293:1233-41.
Filizola et al, BUNDLE: a program for building the transmembrane domains of G-protein-coupled receptors. J Comput Aided Mol Des. 1998 12:111-8.
Gimpl et al, The oxytocin receptor system: structure, function, and regulation. Physiol Rev. 2001 81:629-83 (Review).
Gouldson et al, Domain swapping in G-protein coupled receptor dimers. Protein Eng. 1998 11:1181-93.
Gouldson et al, Dimerization and domain swapping in G-protein-coupled receptors: a computational study. Neuropsychopharmacology. 2000 23:S60-77.
Hurley et al, Structure-function studies of the eighth hydrophobic domain of a serotonin receptor. J Neurochem. 1999 72:413-21.
Krasnoperov et al, Structural requirements for alpha-latrotoxin binding and alpha-latrotoxin-stimulated secretion. A study with calcium-independent receptor of alpha-latrotoxin (CIRL) deletion mutants. J Biol Chem. 1999 274:3590-6.
Missale et al, Dopamine receptors: from structure to function. Physiol Rev. 1998 78:189-225 (Review).
Mouledous et al, Functional inactivation of the nociceptin receptor by alanine substitution of glutamine 286 at the C terminus of transmembrane segment VI: evidence from a site-directed mutagenesis study of the ORL1 receptor transmembrane-binding domain. Mol Pharmacol. 2000 57:495-502.
Olah et al, The role of receptor structure in determining adenosine receptor activity. Pharmacol Ther. 2000 85:55-75 (Review).
Orry et al, Modeling and docking the endothelin G-protein-coupled receptor. Biophys J. 2000 79:3083-94. Palczewski et al, Crystal structure of rhodopsin: A G protein-coupled receptor. Science 2000 289:739-45.

(Continued)

*Primary Examiner* — Ruixiang Li
(74) *Attorney, Agent, or Firm* — James S. Keddie; Carol L. Francis; Bozicevic, Field & Francis

(57) ABSTRACT

The present invention relates to methods of identifying whether a candidate compound is a modulator of a G protein-coupled receptor (GPCR). In some embodiments, the GPCR is mammalian, preferably human. In some embodiments, the GPCR is expressed endogenously by cardiomyocytes. In some embodiments, the GPCR is coupled to Gq. In some embodiments, the GPCR increases the intracellular level of inositol 1,4,5-triphosphate (IP3). In some embodiments, a modulator of the GPCR is a modulator of cardiomyocyte hypertrophy. The present invention further relates to methods of using a modulator of the GPCR. Preferred modulators are inverse agonists and antagonists. Inverse agonists and antagonists of the invention are useful as therapeutic agents for the prevention or treatment of heart disease, including hypertrophic cardiomyopathy and congestive heart failure, in particular hypertrophic cardiomyopathy resulting from post-myocardial infarction remodeling, cardiac valve disease, sustained cardiac afterload, myocarditis, and familial hypertrophic cardiomyopathy.

12 Claims, 7 Drawing Sheets

OTHER PUBLICATIONS

Sealfon et al, Functional domains of the gonadotropin-releasing hormone receptor. Cell Mol Neurobiol. 1995 15:25-42 (Review).

Shin N et al, Molecular modeling and site-specific mutagenesis of the histamine-binding site of the histamine H4 receptor. Mol Pharmacol. 2002 62:38-47.

Ulloa-Aguirre et al, Structure-activity relationships of G protein-coupled receptors. Arch Med Res. 1999 30:420-35 (Review).

Yang et al, Molecular determinants of human melanocortin-4 receptor responsible for antagonist SHU9119 selective activity. J Biol Chem. 2002 277:20328-35.

\* cited by examiner

Figure 3. Immunostaining of RUP40 in rat heart
Anti-RUP40
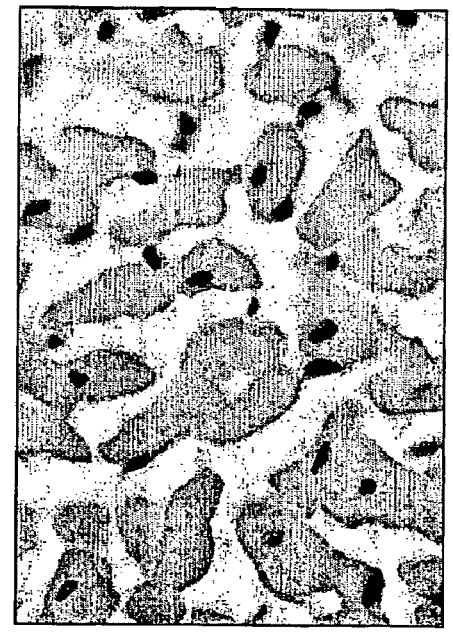
Negative Control
Cardiac myocytes

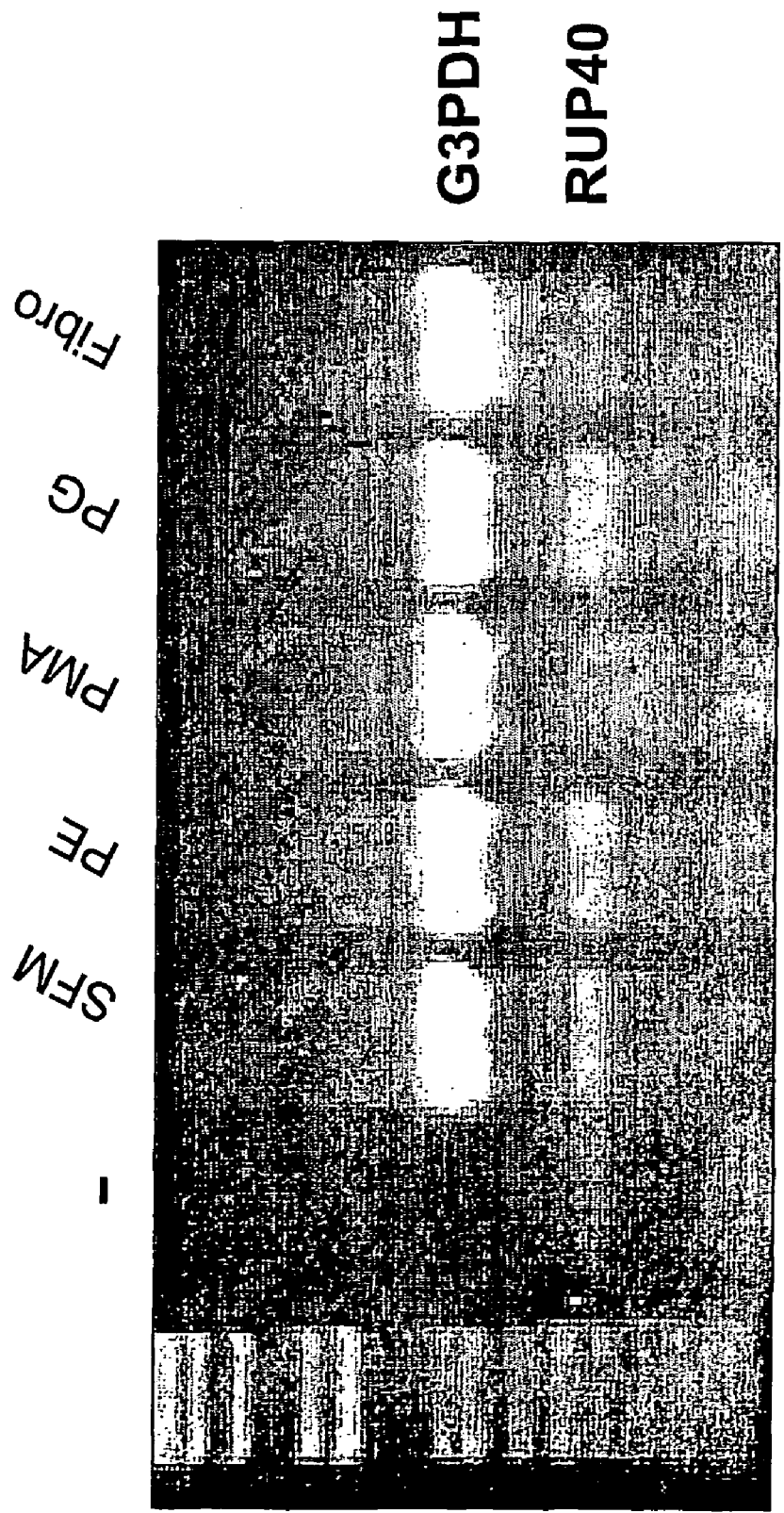
Figure 4. RUP40 is expressed in cardiomyocytes.

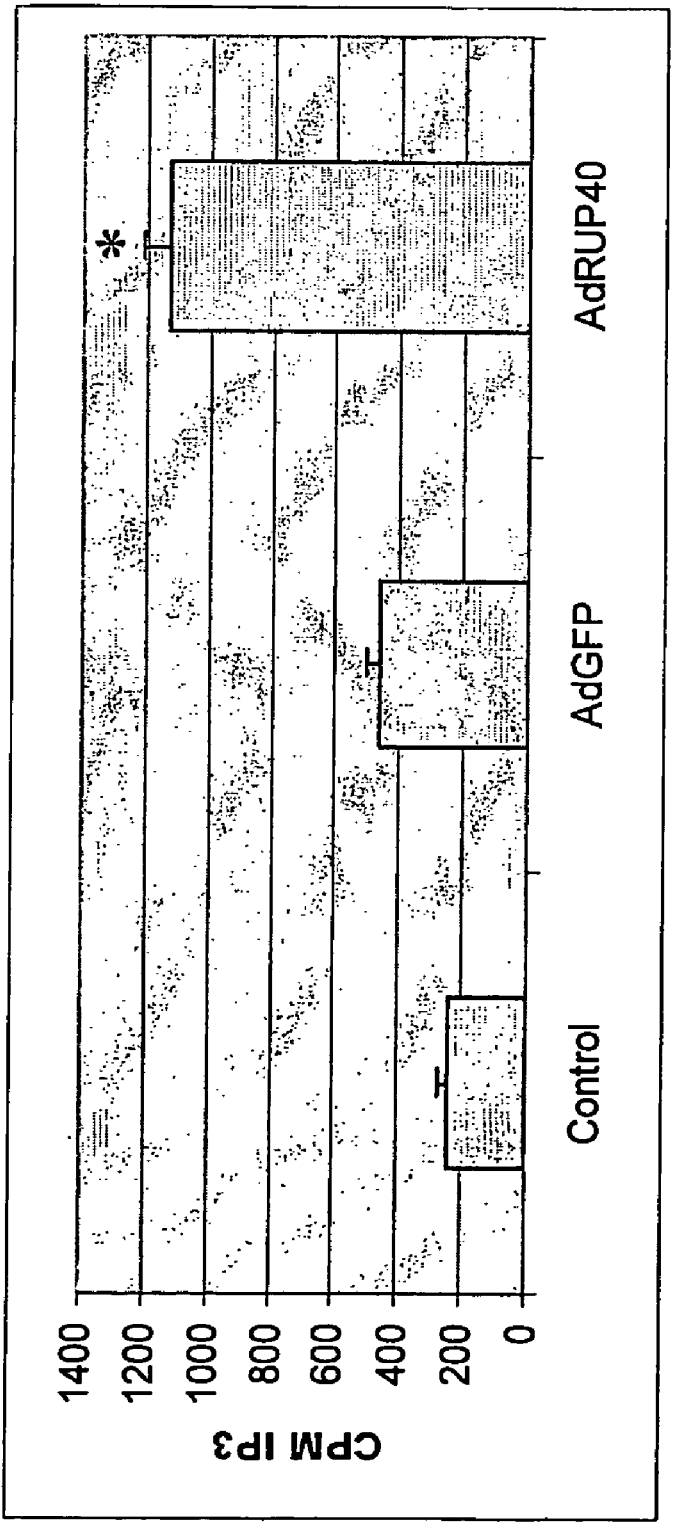
Figure 5. Overexpression of RUP40 in cardiomyocytes stimulates increased IP3 accumulation.

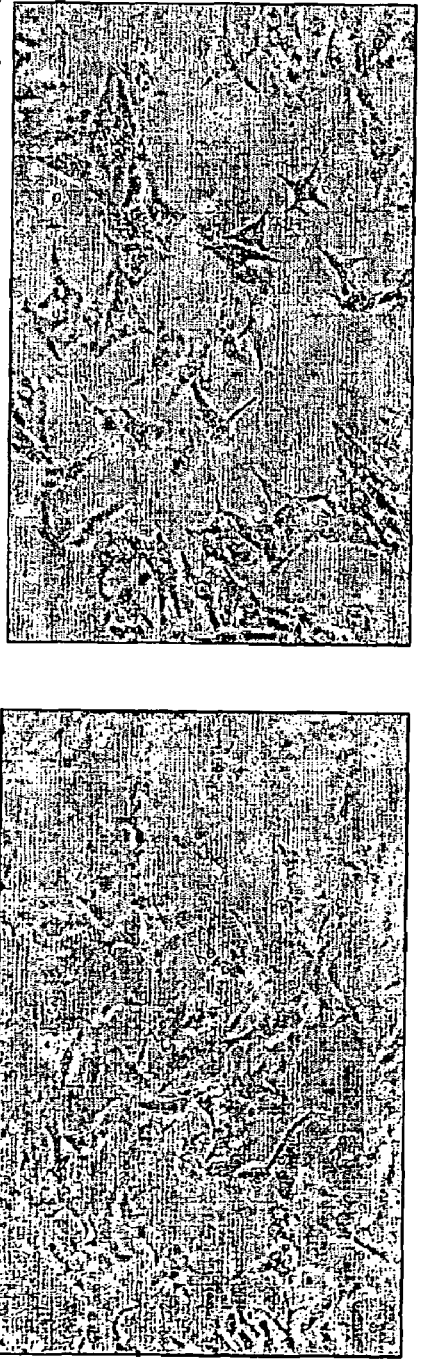
Figure 6A. Overexpression of RUP40 stimulates hypertrophy of cardiomyocytes
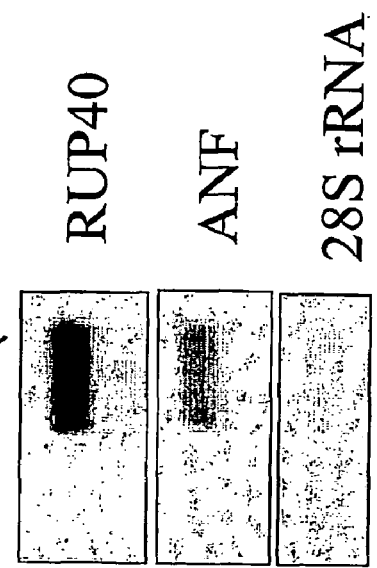
Figure 6B. Overexpression of RUP40 stimulates increased ANF expression in cardiomyocytes

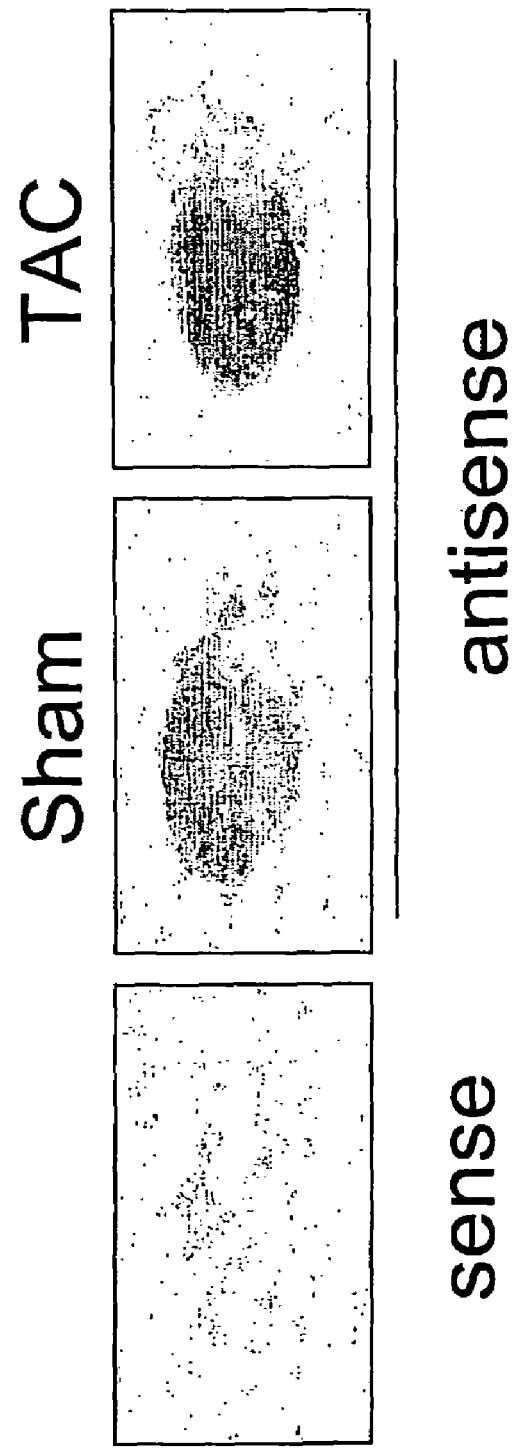
Figure 7. Myocardial expression of RUP40 mRNA in mouse heart: sham versus pressure overload

HUMAN G PROTEIN-COUPLED RECEPTOR AND MODULATORS THEREOF FOR THE TREATMENT OF CARDIOVASCULAR DISORDERS

This application claims the benefit of priority from the following provisional application, filed via U.S. Express mail with the United States Patent and Trademark Office on the indicated date: U.S. Provisional No. 60/480,046, filed Jun. 20, 2003. The disclosure of the foregoing application is herein incorporated by reference in its entirety.

FIELD OF THE INVENTION

The present invention relates to methods of identifying whether a candidate compound is a modulator of a G protein-coupled receptor (GPCR). In some embodiments, the GPCR is mammalian, preferably human. In some embodiments, the GPCR is expressed endogenously by cardiomyocytes. In some embodiments, the GPCR is coupled to Gq. In some embodiments, the GPCR increases the intracellular level of inositol 1,4,5-triphosphate (IP3). In some embodiments, a modulator of the GPCR is a modulator of cardiomyocyte hypertrophy. The present invention further relates to methods of using a modulator of the GPCR. Preferred modulators are inverse agonists and antagonists. Inverse agonists and antagonists of the invention are useful as therapeutic agents for the prevention or treatment of heart disease, including hypertrophic cardiomyopathy and congestive heart failure, in particular hypertrophic cardiomyopathy resulting from post-myocardial infarction remodeling, cardiac valve disease, sustained cardiac afterload, myocarditis, and familial hypertrophic cardiomyopathy.

BACKGROUND OF THE INVENTION

A. Congestive Heart Failure

Congestive heart failure (CHF) affects nearly 5 million Americans with over 500,000 new cases diagnosed annually. By definition, CHF is a clinical syndrome in which heart disease reduces cardiaC output, increases venous pressures, and is accompanied by molecular abnormalities that cause progressive deterioration of the failing heart (From; Heart Failure: Pathophysiology, Molecular Biology, and Clinical Management, Katz, AM, Lippincott Williams and Wilkins, 2000). Despite decades of research a detailed understanding of the causes of CHF are still unclear. However, scientific and clinical findings clearly demonstrate that an early phase of the disease process consists of a maladaptive response of the myocardium to stress known as 'cardiac hypertrophy' (also, 'hypertrophic cardiomyopathy'). Chronic overload on the heart in the setting of unremitting hypertension, valve disease, or tissue damage (myocardial infarction) results in a hypertrophic growth response which is initially adaptive in so far as cardiac output is temporarily restored but gradually becomes maladaptive over time resulting in decreased contractile function, cardiac dilatation and failure. Because the 5-year survival rate, once heart failure becomes symptomatic, is less that 50%, any definition of heart failure that does not consider the molecular processes that accelerate myocardial hypertrophy overlooks a major clinical feature of this syndrome.

Cell culture and small animal studies have clearly demonstrated that G-protein coupled receptors on cardiac myocytes are highly important regulators of cardiac contractile function and are also involved in the regulation of myocyte hypertrophy (for review see; Adams and Brown, Oncogene, 20, 1626-1634, 2001). In fact, the positive effects of ACE inhibitors for treatment of CHF in humans is thought to at least partially involve the reduction of maladaptive hypertrophy via indirect inhibition of angiotensin II receptor activation in the myocardium.

However, despite improvements in pharmacological therapies for CHF over the past ten years (ACE inhibitors, beta-blockers) only a 20-30% reduction in mortality has been demonstrated with current optimal therapies. In the future, development of better drugs and identification of new therapeutic targets will likely improve the clinical outcome of patients with CHF.

B. G Protein-Coupled Receptors

Although a number of receptor classes exist in humans, by far the most abundant and therapeutically relevant is represented by the G protein-coupled receptor (GPCR) class. It is estimated that there are some 30,000-40,000 genes within the human genome, and of these, approximately 2% are estimated to code for GPCRs.

GPCRs represent an important area for the development of pharmaceutical products: from approximately 20 of the 100 known GPCRs, approximately 60% of all prescription pharmaceuticals have been developed. For example, in 1999, of the top 100 brand name prescription drugs, the following drugs interact with GPCRs (the primary diseases and/or disorders treated related to the drug is indicated in parentheses):

| | |
|---|---|
| Claritin ® (allergies) | Prozac ® (depression) |
| Vasotec ® (hypertension) | Paxil ® (depression) |
| Zoloft ® (depression) | Zyprexa ® (psychotic disorder) |
| Cozaar ® (hypertension) | Imitrex ® (migraine) |
| Zantac ® (reflux) | Propulsid ® (reflux disease) |
| Risperdal ® (schizophrenia) | Serevent ® (asthma) |
| Pepcid ® (reflux) | Gaster ® (ulcers) |
| Atrovent ® (bronchospasm) | Effexor ® (depression) |
| Depakote ® (epilepsy) | Cardura ® (prostatic hypertrophy) |
| Allegra ® (allergies) | Lupron ® (prostate cancer) |
| Zoladex ® (prostate cancer) | Diprivan ® (anesthesia) |
| BuSpar ® (anxiety) | Ventolin ® (bronchospasm) |
| Hytrin ® (hypertension) | Wellbutrin ® (depression) |
| Zyrtec ® (rhinitis) | Plavix ® (MI/stroke) |
| Toprol-XL ® (hypertension) | Tenormin ® (angina) |
| Xalatan ® (glaucoma) | Singulair ® (asthma) |
| Diovan ® (hypertension) | Hamal ® (prostatic hyperplasia) |
| (Med Ad News 1999 Data). | |

GPCRs share a common structural motif, having seven sequences of between 22 to 24 hydrophobic amino acids that form seven alpha helices, each of which spans the membrane [each span is identified by number, i.e., transmembrane-1 (TM-1), transmembrane-2 (TM-2), etc.]. The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane [these are referred to as "extracellular" regions 1, 2 and 3 (EC-1, EC-2 and EC-3), respectively]. The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane [these are referred to as "intracellular" regions 1, 2 and 3 (IC-1, IC-2 and IC-3), respectively]. The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor), there is a Change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, T., 43 *Life Sciences* 1095 (1988). Although other G proteins exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

Gs-coupled GPCRs elevate intracellular cAMP levels. Gi-, Go-, or Gz-coupled GPCRs lower intracellular cAMP levels. Gq-coupled GPCRs elevate intracellular IP3 and Ca2+ levels.

There are also promiscuous G proteins, which appear to couple several classes of GPCRs to the phospholipase C pathway, such as G15 or G16 [Offermanns & Simon, J Biol Chem (1995) 270:15175-80], or chimeric G proteins designed to couple a large number of different GPCRs to the same pathway, e.g. phospholipase C [Milligan & Rees, Trends in Pharmaceutical Sciences (1999) 20:118-24].

The melanophore technology (see infra) is useful in interrogating the G-protein coupling of a GPCR and also for identifying whether a compound is a modulator of the GPCR.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation" (see, e.g., PCT Application Number PCT/US98/07496 published as WO 98/46995 on 22 Oct. 1998; the disclosure of which is hereby incorporated by reference in its entirety).

SUMMARY OF THE INVENTION

RUP40 is a class II GPCR comprising a heptahelical domain similar to that of the secretin family. Nucleotide sequence encoding human RUP40 polypeptide is given in SEQ ID NO:1. The amino acid sequence of said encoded human RUP40 polypeptide is given in SEQ ID NO:2. Nucleotide sequence encoding rat RUP40 polypeptide is given in SEQ ID NO:3. The amino acid sequence of said encoded rat RUP40 polypeptide is given in SEQ ID NO:4. Nucleotide sequence encoding partial mouse RUP40 polypeptide is given in SEQ ID NO:5. The amino acid sequence of said encoded partial mouse RUP40 polypeptide is given in SEQ ID NO:6.

RUP40 is predicted to have a signal peptide, an SEA module, and a GPCR proteolytic site (GPS) domain. Proteolytic cleavage of the signal peptide is predicted to occur approximately between amino acids 21 and 22 of SEQ ID NO:2 for human RUP40 and approximately between amino acids 24 and 25 of SEQ ID NO:4 for rat RUP40 (SignalP; www.cbs.dtu.dk/services/SignalP-2.0/). Proteolytic cleavage within the SEA module is predicted to occur approximately between amino acids 226 and 227 of SEQ ID NO:2 for human RUP40 and approximately between amino acids 223 and 224 of SEQ ID NO:4 for rat RUP40 [Abe J et al., (2002) J Biol Chem 277:23391-8; the disclosure of which is hereby incorporated by reference in its entirety]. The GPS domain is predicted to correspond approximately to amino acids 954 to 997 of SEQ ID NO:2 for human RUP40 and approximately to amino acids 954-1000 of SEQ ID NO:4 for rat RUP40 [Krasnoperov, V et al., J Biol Chem (2002) 277:46518-26; the disclosure of which is hereby incorporated by reference in its entirety]. Proteolytic cleavage within the GPS domain is predicted to occur approximately between amino acids 990 and 991 of SEQ ID NO:2 for human RUP40 and approximately between amino acids 993 and 994 of SEQ ID NO:4 for rat RUP40 [Krasnoperov, V et al., J Biol Chem (2002) 277:46518-26].

RUP40 is highly expressed in mammalian heart, lung, aorta, and adipose. In the heart, RUP40 is highly expressed by left ventricle. Within ventricle, RUP40 is expressed by cardiomyocytes. Applicants have determined that overexpression of RUP40 in cardiomyocytes results in increased IP3 accumulation and a subsequent increase in atrial natriuretic factor (ANF) expression and hypertrophy. Under conditions of pressure overload in mice subjected to transverse aortic constriction (TAC) resulting in cardiac hypertrophy, levels of RUP40 mRNA are maintained or increased slightly. The combination of high-level myocardial expression and the capacity to generate hypertrophic signaling makes RUP40 an attractive therapeutic target for the treatment of hypertrophic cardiomyopathy resulting from a hemodynamic or genetic disorder. Inverse agonists and antagonists of the invention are useful as therapeutic agents for the prevention or treatment of heart disease, including hypertrophic cardiomyopathy and congestive heart failure, in particular hypertrophic cardiomyopathy resulting from post-myocardial infarction remodeling, cardiac valve disease, sustained cardiac afterload, myocarditis, and familial hypertrophic cardiomyopathy.

In a first aspect, the invention features a method of identifying whether a candidate compound is a modulator of a RUP40 GPCR, wherein the receptor couples to a G protein, said receptor comprising an amino acid sequence selected from the group consisting of:
  (a) amino acids 1-1,346 of SEQ ID NO:2;
  (b) amino acids 1-990 of SEQ ID NO:2;
  (c) amino acids 991-1,346 of SEQ ID NO:2;
  (d) amino acids 954-997 of SEQ ID NO:2;
  (e) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
  (f) amino acids 1-1,349 of SEQ ID NO:4;
  (g) amino acids 1-993 of SEQ ID NO:4;
  (h) amino acids 994-1,349 of SEQ ID NO:4;
  (i) amino acids 954-1000 of SEQ ID NO:4; and
  (j) amino acids 1-141 of SEQ ID NO:6;
or a biologically active fragment of the amino acid sequence of SEQ ID NO:2 or 4; or a constitutively activated mutant of the amino acid sequence of SEQ ID NO:2 or 4 or said biologically active fragment thereof;
comprising the steps of:
  (i) contacting the candidate compound with the receptor;
  (ii) determining whether the receptor functionality is modulated;
wherein a change in receptor functionality is indicative of the candidate compound being a modulator of a RUP40 GPCR.

In some embodiments, said biologically active fragment of RUP40 GPCR of SEQ ID NO:2 or 4 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, n1=2, n2=994, and c=1,349 for RUP40 GPCR of SEQ ID NO:4. In some embodiments, said biologically active fragment of RUP40 GPCR is selected from amino acids 2-1,346,22-1,346,227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, said biologically active fragment of RUP40 GPCR is selected from amino acids 2-1,349,25-1,349,224-1,349, and 994-1,349 of SEQ ID NO:4, where amino acid 25 is understood to be the approximate site of predicted signal peptide cleavage, amino acid 224 is understood to be the approximate site of predicted proteolytic cleavage within the SEA module, and amino acid 994 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2. In some embodiments, n1=25, n2=994, and c=1,349 for RUP40 GPCR of SEQ ID NO:4. In some embodiments, n1=224, n2=994, and c=1,349 for RUP40 GPCR of SEQ ID NO:4.

Methods of making a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2, 4 or 6 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 801 of SEQ ID NO:2, or comprising a substitution of methionine for threonine at amino acid position 856 of SEQ ID NO:2 is envisioned to be within the scope of the invention. In some embodiments, an allelic variant of RUP40 GPCR of SEQ ID NO:2 is the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8.

Mammalian orthologs of human RUP40 GPCR of SEQ ID NO:2 are envisioned to be within the scope of the invention. In some embodiments, said mammalian ortholog encompasses mouse RUP40, rat RUP40, pig RUP40, and non-human primate RUP40.

Variants of said RUP40 GPCR comprising an amino acid sequence at least 95%, at least 96%, at least 97%, at least 98%, at least 99%, at least, 99.1%, at least 99.2%, at least 99.3%, at least 99.4%, at least 99.5%, at least 99.6%, at least 99.7%, at least 99.8%, or at least 99.9% identical to any of (a) to (j) are envisioned to be within the scope of the invention. Percent identity can be determined conventionally using known computer programs. Such algorithms and programs include, but are by no means limited to, TBLASTN, BLASTP, FASTA, TFASTA, and CLUSTALW [Pearson and Lipman (1988) Proc Natl Acad Sci USA 85:2444-8; Altschul et al. (1990) J Mol Biol 215:403-10; Thompson et al. (1994) Nucleic Acids Res 22:4673-80; Higgins et al. (1996) Meth Enzymol 266:383-402; Altschul et al. (1997) Nucleic Acids Res 25:3389-3402; Altschul et al. (1993) Nature Genetics 3:266-272; the disclosures of which are hereby incorporated by reference in their entireties].

In some embodiments, protein sequence homologies are evaluated using the Basic Local Alignment Search Tool ("BLAST"), which is well known in the art [See, e.g., Karlin and Altschul (1990) Proc Natl Acad Sci USA 87:2264-8; Altschul et al., 1990, 1993, 1997, all supra].

In some embodiments, the method for determining percent identity between two amino acid sequences is a method for determining the best overall match between a query sequence (e.g., the amino acid sequence of SEQ ID NO:2) and a sequence to be interrogated, also referred to as a global sequence alignment, using the FASTDB computer program based on the algorithm of Brutlag et al. [Comp App Biosci (1990) 6:237-245; the disclosure of which is hereby incorporated by reference in its entirety]. In a sequence alignment the query and interrogated sequences are both amino acid sequences. The results of said global sequence alignment is in percent identity. Preferred parameters used in a FASTDB amino acid alignment are: Matrix=PAM 0, k-tuple=2, Mismatch Penalty=1, Joining Penalty=20, Randomization Group=25, Length=0, Cutoff Score=1, Window Size=sequence length, Gap Penalty=5, Gap Size Penalty=0.05, Window Size=247 or the length of the interrogated amino acid sequence, whichever is shorter.

If the interrogated sequence is shorter than the query sequence due to N- or C-terminal deletions, not because of internal deletions, the results, in percent identity, must be manually corrected because the FASTDB program does not account for N- and C-terminal truncations of the interrogated sequence when calculating global percent identity. For interrogated sequences truncated at the N- and C-termini, relative to the query sequence, the percent identity is corrected by calculating the number of residues of the query sequence that are N- and C-terminal of the interrogated sequence, that are not matched/aligned with a corresponding interrogated sequence residue, as a percent of the total bses of the query sequence. Whether a residue is matched/aligned is determined by results of the FASTDB sequence alignment. This percentage is then subtracted from the perecent identity, calculated by the above FASTDB program using the specified parameters, to arrive at a final percent identity score. This final percent identity score is what is used for the purposes of the present invention. Only residues to the N- and C-termini of the interrogated sequence, which are not matched/aligned with the query sequence, are considered for the purposes of manually adjusting the percent identity score. That is, only query amino acid residues outside the farthest N- and C-terminal residues of the interrogated sequence.

For example, a 90 amino acid residue interrogated sequence is aligned with a 100-residue query sequence to determine percent identity. The deletion occurs at the N-terminus of the interrogated sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched, the final percent identity would be 90%.

In another example, a 90-residue interrogated sequence is compared with a 100-residue query sequence. This time the deletions are internal so there are no residues at the N- or C-termini of the interrogated sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other corrections are made for the purposes of the present invention.

In some embodiments, said RUP40 GPCR is recombinant.

In some embodiments, said RUP40 GPCR comprises heterologous amino acid sequence. In some embodiments, said heterologous amino acid sequence is an epitope tag. In some embodiments, said epitope tag is hemagglutinin (HA) epitope tag. In some embodiments, said epitope tag is c-myc epitope tag. In some embodiments, said epitope tag is V5 epitope tag. Procedures for providing said HA, c-myc or V5 tag are well known to those of ordinary skill in the art (Clontech, Palo Alto, Calif. and Invitrogen, Carlsbad, Calif., for example).

In some embodiments, said receptor further comprises proteolytic cleavage of a signal peptide:

In some embodiments, said receptor further comprises proteolytic cleavage within an SEA module.

In some embodiments, said receptor further comprises proteolytic cleavage within a GPS domain.

In some embodiments, said contacting is carried out in the presence of a known ligand of the GPCR. In some embodiments, said known ligand is an agonist of the GPCR.

The invention also relates to a method of identifying whether a candidate compound is a modulator of a cardiovascular disorder, comprising the steps of:
(a) contacting the candidate compound with a RUP40 GPCR, wherein the receptor couples to a G protein, said receptor comprising an amino acid sequence selected from the group consisting of:
  (i) amino acids 1-1,346 of SEQ ID NO:2;
  (ii) amino acids 1-990 of SEQ ID NO:2;
  (iii) amino acids 991-1,346 of SEQ ID NO:2;
  (iv) amino acids 954-997 of SEQ ID NO:2;
  (v) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
  (vi) amino acids 1-1,349 of SEQ ID NO:4;
  (vii) amino acids 1-993 of SEQ ID NO:4;
  (viii) amino acids 994-1,349 of SEQ ID NO:4;
  (ix) amino acids 954-1000 of SEQ ID NO:4; and
  (x) amino acids 1-141 of SEQ ID NO:6;
  or a biologically active fragment of the amino acid sequence of SEQ ID NO:2 or 4; or a constitutively activated mutant of the amino acid sequence of SEQ ID NO:2 or 4 or said biologically active fragment thereof;
(b) determining whether the receptor functionality is modulated;

wherein a change in receptor functionality is indicative of the candidate compound being a modulator of a cardiovascular disorder.

In some embodiments, said biologically active fragment of RUP40 GPCR of SEQ ID NO:2 or 4 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, n1=2, n2=994, and c=1,349 for RUP40 GPCR of SEQ ID NO:4. In some embodiments, said biologically active fragment of RUP40 GPCR is selected from amino acids 2-1,346,22-1,346,227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, said biologically active fragment of RUP40 GPCR is selected from amino acids 2-1,349,25-1,349,224-1,349, and 994-1,349 of SEQ ID NO:4, where amino acid 25 is understood to be the approximate site of predicted signal peptide cleavage, amino acid 224 is understood to be the approximate site of predicted proteolytic cleavage within the SEA module, and amino acid 994 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2. In some embodiments, n1=25, n2=994, and c=1,349 for RUP40 GPCR of SEQ ID NO:4. In some embodiments, n1=224, n2=994, and c=1,349 for RUP40 GPCR of SEQ ID NO:4.

Methods of making a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2, 4 or 6 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 801 of SEQ ID NO:2, or comprising a substitution of methionine for threonine at amino acid position 856 of SEQ ID NO:2 is envisioned to be within the scope of the invention. In some embodiments, an allelic variant of RUP40 GPCR of SEQ ID NO:2 is the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8.

Mammalian orthologs of human RUP40 GPCR of SEQ ID NO:2 are envisioned to be within the scope of the invention.

In some embodiments, said mammalian ortholog encompasses mouse RUP40, rat RUP40, pig RUP40, and non-human primate RUP40.

Variants of said RUP40 GPCR comprising an amino acid sequence at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to any of (i) to (x) are envisioned to be within the scope of the invention.

In some embodiments, said RUP40 GPCR is recombinant

In some embodiments, said RUP40 GPCR comprises heterologous amino acid sequence. In some embodiments, said heterologous amino acid sequence is an epitope tag. In some embodiments, said epitope tag is hemagglutinin (HA) epitope tag. In some embodiments, said epitope tag is c-myc epitope tag. In some embodiments, said epitope tag is V5 epitope tag. Procedures for providing said HA, c-myc or V5 tag are well known to those of ordinary skill in the art (Clontech, Palo Alto, Calif. and Invitrogen, Carlsbad, Calif., for example).

In some embodiments, said receptor further comprises proteolytic cleavage of a signal peptide.

In some embodiments, said receptor further comprises proteolytic cleavage within an SEA module.

In some embodiments, said receptor further comprises proteolytic cleavage within a GPS domain.

In some embodiments, said contacting is carried out in the presence of a known ligand of the GPCR. In some embodiments, said known ligand is an agonist of the GPCR.

In some embodiments, said cardiovascular disorder is heart disease. Heart disease includes but is not limited to congestive heart failure, congestive cardiomyopathy, heart hypertrophy, left ventricular hypertrophy, right ventricular hypertrophy, post-infarction heart rupture, ventricular septal rupture, endocarditis (including bacterial); heart aneurysm, pulmonary heart disease, rheumatic heart disease, and ventricular dysfunction. Heart disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Heart disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy.

In some embodiments, said cardiovascular disorder is hypertrophic cardiomyopathy. In some embodiments, said hypertrophic cardiomyopathy results from a hemodynamic disorder. In some embodiments, said hypertrophic cardiomyopathy results from a genetic disorder.

In some embodiments, said hypertrophic cardiomyopathy resulting from a disorder selected from the group consisting of:
  (a) post-myocardial infarction remodeling;
  (b) cardiac valve disease;
  (c) sustained cardiac afterlod;
  (d) myocarditis; and
  (e) familial hypertrophic cardiomyopathy.

In some embodiments, said cardiovascular disorder is congenital heart defect. Congenital heart defect includes but is not limited to aortic coarctation, aortopulmonary septal defect, trilogy of Fallot, ventricular heart septal defect, and familial hypertrophic cardiomyopathy.

In certain embodiments, a decrease in receptor functionality is indicative of the candidate compound being a compound that blocks or decreases cardiomyocyte hypertrophy.

In certain embodiments, a decrease in receptor functionality is indicative of the candidate compound being a compound that blocks or decreases hypertrophic cardiomyopathy in a mammal.

In certain embodiments, a decrease in receptor functionality is indicative of the candidate compound being useful for the prevention of or treatment for hypertrophic cardiomyopathy in a mammal.

The invention also relates to a method of determining whether a candidate compound is a modulator of a RUP40 GPCR, comprising the steps of:
  (a) culturing RUP40 GPCR-expressing host cells under conditions that would allow expression of a recombinant RUP40 GPCR, said host cells being transfected with an expression vector comprising a polynucleotide encoding said recombinant RUP40 GPCR comprising an amino acid sequence selected from the group consisting of
    (i) amino acids 1-1,346 of SEQ ID NO:2;
    (ii) amino acids 1-990 of SEQ ID NO:2;
    (iii) amino acids 991-1,346 of SEQ ID NO:2;
    (iv) amino acids 954-997 of SEQ ID NO:2;
    (v) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
    (vi) amino acids 1-1,349 of SEQ ID NO:4;
    (vii) amino acids 1-993 of SEQ ID NO:4;
    (viii) amino acids 994-1,349 of SEQ NO:4;
    (ix) amino acids 954-1000 of SEQ ID NO:4; and
    (x) amino acids 1-141 of SEQ ID NO:6;
  or a biologically active fragment of the amino acid sequence of SEQ ID NO:2 or 4; or a constitutively activated mutant of the amino acid sequence of SEQ ID NO:2 or 4 or said biologically active fragment thereof;
  (b) contacting the RUP40 GPCR-expressing host cells of step (a) with the candidate compound;
  (c) contacting control host cells with the candidate compound of step (b), wherein said control host cells do not express recombinant RUP40 GPCR protein;
  (d) measuring the modulating effect of the candidate compound which interacts with the recombinant RUP40 GPCR from the host cells of step (a) and control host cells of step (c); and
  (e) comparing the modulating effect of the test compound on the host cells and control host cells.

In some embodiments, said biologically active fragment of RUP40 GPCR of SEQ ID NO:2 or 4 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, n1=2, n2=994, and c=1,349 for RUP40 GPCR of SEQ ID NO:4. In some embodiments, said biologically active fragment of RUP40 GPCR is selected from amino acids 2-1,346, 22-1,346, 227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, said biologically active fragment of RUP40 GPCR is selected from amino acids 2-1,349,25-1,349,224-1,349, and 994-1,349 of SEQ ID NO:4, where amino acid 25 is understood to be the approximate site of predicted signal peptide cleavage, amino acid 224 is understood to be the approximate site of predicted proteolytic cleavage with the SEA domain, and amino acid 994 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2. In some embodiments, n1=25, n2=994, and c=1,349 for RUP40 GPCR of SEQ ID NO:4. In some embodiments, n1=224, n2=994, and c=1,349 for RUP40 GPCR of SEQ ID NO:4.

Methods of making a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2, 4 or 6 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 801 of SEQ BD NO:2, comprising a substitution of methionine for threonine at amino acid position 856 of SEQ ID NO:2 is envisioned to be within the scope of the invention. In some embodiments, an allelic variant of RUP40 GPCR of SEQ ID NO:2 is the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8.

Mammalian orthologs of human RUP40 GPCR of SEQ ID NO:2 are envisioned to be within the scope of the invention. In some embodiments, said mammalian ortholog encompasses mouse RUP40, rat RUP40, pig RUP40, and non-human primate RUP40.

Variants of said RUP40 GPCR comprising an amino acid sequence at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to any of (i) to (x) are envisioned to be within the scope of the invention.

In some embodiments, said RUP40 GPCR comprises heterologous amino acid sequence. In some embodiments, said heterologous amino acid sequence is an epitope tag. In some embodiments, said epitope tag is hemagglutinin (HA) epitope tag. In some embodiments, said epitope tag is c-myc epitope tag. In some embodiments, said epitope tag is V5 epitope tag.

In some embodiments, said receptor further comprises proteolytic cleavage of a signal peptide.

In some embodiments, said receptor further comprises proteolytic cleavage within an SEA module.

In some embodiments, said receptor further comprises proteolytic cleavage within a GPS domain.

In some embodiments, said transfection is transient. In other some embodiments, said transfection is stable.

In some embodiments, said expression vector is pCMV. In some other embodiments, said expression vector is adenoviral. An exemplary adenoviral vector may be purchased as AdEasy™ from Qbiogene (Carlsbad, Calif.) [He, T C et al., Proc. Natl. Acad. Sci. USA (1998) 95:2509-14; and U.S. Pat. No. 5,922,576; the disclosures of which are hereby incorporated by reference in their entireties]. Other suitable vectors will be readily apparent to those of ordinary skill in the art.

In some embodiments, said host cell is mammalian and selected from the group consisting of 293, 293T, CHO and COS-7. In other some embodiments, said host cell is melanophore. In other some embodiments, said host cell is cardiomyocyte. Other suitable host cells will be readily apparent to those of ordinary skill in the art.

The invention also relates to a method of determining whether a candidate compound is a modulator of a RUP40 GPCR, comprising the steps of:

(a) culturing RUP40 GPCR-expressing host cells under conditions that would allow expression of a recombinant RUP40 GPCR, said host cells being transfected with an expression vector comprising a polynucleotide encoding said recombinant RUP40 GPCR comprising an amino acid sequence selected from the group consisting of:
  (i) amino acids 1-1,346 of SEQ ID NO:2;
  (ii) amino acids 1-990 of SEQ ID NO:2;
  (iii) amino acids 991-1,346 of SEQ ID NO:2;
  (iv) amino acids 954-997 of SEQ ID NO:2;
  (v) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
  (vi) amino acids 1-1,349 of SEQ ID NO:4;
  (vii) amino acids 1-993 of SEQ ID NO:4;
  (viii) amino acids 994-1,349 of SEQ ID NO:4;
  (ix) amino acids 954-1000 of SEQ ID NO:4; and
  (x) amino acids 1-141 of SEQ ID NO:6;
or a biologically active fragment of the amino acid sequence of SEQ ID NO:2 or 4; or a constitutively activated mutant of the amino acid sequence of SEQ ID NO:2 or 4 or said biologically active fragment thereof;

(b) contacting a first population of RUP40 GPCR-expressing cells of step (a) with a known ligand of said RUP40 GPCR;

(c) contacting a second population of RUP40 GPCR-expressing cells of step (a) with the candidate compound and with the known RUP40 GPCR ligand;

(d) contacting control host cells with the candidate compound of step (c), wherein said control host cells do not express recombinant RUP40 GPCR protein;

(e) measuring the modulating effect of the candidate compound, which interacts with recombinant RUP40 GPCR, in the presence and absence of the known RUP40 GPCR ligand, from the cells of step (b), step (c) and step (d); and (f) comparing the modulating effect of the candidate compound as determined from step (b), step (c) and step (d).

In some embodiments, said biologically active fragment of RUP40 GPCR of SEQ ID NO:2 or 4 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, n1=2, n2=994, and c=1,349 for RUP40 GPCR of SEQ ID NO:4. In some embodiments, said biologically active fragment of RUP40 GPCR is selected from amino acids 2-1,346,22-1,346,227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, said biologically active fragment of RUP40 GPCR is selected from amino acids 2-1,349,25-1,349,224-1,349, and 994-1,349 of SEQ ID NO:4, where amino acid 25 is understood to be the approximate site of predicted signal peptide cleavage, amino acid 224 is understood to be the approximate site of predicted proteolytic cleavage within the SEA module, and amino acid 994 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2. In some embodiments, n1=25, n2=994, and c=1,349 for RUP40 GPCR of SEQ ID NO:4. In some embodiments, n1=224, n2=994, and c=1,349 for RUP40 GPCR of SEQ ID NO:4.

Methods of making a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2, 4 or 6 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 801 of SEQ ID NO:2, or comprising a substitution of methionine for threonine at amino acid position 856 of SEQ ID NO:2 is envisioned to be within the scope of the invention. In some embodiments, an allelic variant of RUP40 GPCR of SEQ ID NO:2 is the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8.

Mammalian orthologs of human RUP40 GPCR of SEQ ID NO:2 are envisioned to be within the scope of the invention. In some embodiments, said mammalian ortholog encompasses mouse RUP40, rat RUP40, pig RUP40, and non-human primate RUP40.

Variants of said RUP40 GPCR comprising an amino acid sequence at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to any of (i) to (x) are envisioned to be within the scope of the invention.

In some embodiments, said RUP40 GPCR comprises heterologous amino acid sequence. In some embodiments, said heterologous amino acid sequence is an epitope tag. In some embodiments, said epitope tag is hemagglutinin (HA) epitope tag. In some embodiments, said epitope tag is c-myc epitope tag. In some embodiments, said epitope tag is V5 epitope tag.

In some embodiments, said receptor further comprises proteolytic cleavage of a signal peptide.

In some embodiments, said receptor further comprises proteolytic cleavage within an SEA module.

In some embodiments, said receptor further comprises proteolytic cleavage within a GPS domain.

In some embodiments, said ligand is an agonist of said RUP40 GPCR.

In some embodiments, said transfection is transient. In other some embodiments, said transfection is stable.

In some embodiments, said expression vector is pCMV. In some other embodiments, said expression vector is adenoviral. Other suitable vectors will be readily apparent to those of ordinary skill in the art.

In some embodiments, said host cell is mammalian and selected from the group consisting of 293, 293T, CRO and COS-7. In other some embodiments, said host cell is melanophore. In other some embodiments, said host cell is cardiomyocyte. Other suitable host cells will be readily apparent to those of ordinary skill in the art.

The invention also relates to a method of determining whether a candidate compound is a modulator of a RUP40 GPCR, comprising the steps of:

(a) culturing RUP40 GPCR-expressing host cells under conditions that would allow expression of a recombinant RUP40 GPCR, said host cells being transfected with an expression vector comprising a polynucleotide encoding said recombinant RUP40 GPCR comprising an amino acid sequence selected from the group consisting of:
  (i) amino acids 1-1,346 of SEQ ID NO:2;
  (ii) amino acids 1-990 of SEQ ID NO:2;
  (iii) amino acids 991-1,346 of SEQ ID NO:2;
  (iv) amino acids 954-997 of SEQ ID NO:2;
  (v) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
  (vi) amino acids 1-1,349 of SEQ ID NO:4;
  (vii) amino acids 1-993 of SEQ ID NO:4;
  (viii) amino acids 994-1,349 of SEQ ID NO:4;
  (ix) amino acids 954-1000 of SEQ ID NO:4; and
  (x) amino acids 1-141 of SEQ ID NO:6;
  or a biologically active fragment of the amino acid sequence of SEQ ID NO:2 or 4; or a constitutively activated mutant of the amino acid sequence of SEQ ID NO:2 or 4 or said biologically active fragment thereof;

(b) contacting a first population of the RUP40 GPCR-expressing host cells of step (a) with the candidate compound;

(c) not contacting a second population of the RUP40 GPCR-expressing cells of step (a) with the candidate compound of step (b);

(d) contacting control host cells to the candidate compound of step (b), wherein said control host cells do not express recombinant RUP40 GPCR protein;

(e) measuring the modulating effect of the candidate compound, which interacts with recombinant RUP40 GPCR protein, from the cells of step (b) and step (c) and from the cells of step (d); and (f) comparing the modulating effect of the candidate compound as determined from step (b) and step (c) and from step (d).

In some embodiments, said biologically active fragment of RUP40 GPCR of SEQ ID NO:2 or 4 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, n1=2, n2=994, and c=1,349 for RUP40 GPCR of SEQ ID NO:4. In some embodiments, said biologically active fragment of RUP40 GPCR is selected from amino acids 2-1,346, 22-1,346, 227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, said biologically active fragment of RUP40 GPCR is selected from amino acids 2-1,349, 25-1,349, 224-1,349, and 994-1,349 of SEQ ID NO:4, where amino acid 25 is understood to be the approximate site of predicted signal peptide cleavage, amino acid 224 is understood to be the approximate site of predicted proteolytic cleavage within the SEA module, and amino acid 994 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2. In some embodiments, n1=25, n2=994, and c=1,349 for RUP40 GPCR of SEQ ID NO:4. In some embodiments, n1=224, n2=994, and c=1,349 for RUP40 GPCR of SEQ ID NO:4.

Methods of making a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2, 4 or 6 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 801 of SEQ ID NO:2, or comprising a substitution of methionine for threonine at amino acid position 856 of SEQ ID NO:2 is envisioned to be within the scope of the invention. In some embodiments, an allelic variant of RUP40 GPCR of SEQ ID NO:2 is the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8.

Mammalian orthologs of human RUP40 GPCR of SEQ ID NO:2 are envisioned to be within the scope of the invention. In some embodiments, said mammalian ortholog encompasses mouse RUP40, rat RUP40, pig RUP40, and non-human primate RUP40.

Variants of said RUP40 GPCR comprising an amino acid sequence at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to any of (i) to (x) are envisioned to be within the scope of the invention.

In some embodiments, said RUP40 GPCR comprises heterologous amino acid sequence. In some embodiments, said heterologous amino acid sequence is an epitope tag. In some embodiments, said epitope tag is hemagglutinin (HA) epitope tag. In some embodiments, said epitope tag is c-myc epitope tag. In some embodiments, said epitope tag is V5 epitope tag.

In some embodiments, said receptor further comprises proteolytic cleavage of a signal peptide.

In some embodiments, said receptor further comprises proteolytic cleavage within an SEA module.

In some embodiments, said receptor further comprises proteolytic cleavage within a GPS domain.

In some embodiments, said transfection is transient. In other some embodiments, said transfection is stable.

In some embodiments, said expression vector is pCMV. In some other embodiments, said expression vector is adenoviral. Other suitable vectors will be readily apparent to those of ordinary skill in the art.

In some embodiments, said host cell is mammalian and selected from the group consisting of 293, 293T, CHO and COS-7. In other some embodiments, said host cell is melanophore. In other some embodiments, said host cell is cardiomyocyte. Other suitable host cells will be readily apparent to those of ordinary skill in the art.

In some embodiments, said G protein is Gq

In some embodiments, said G protein elevates the level of intracellular IP3.

In some embodiments, said G protein elevates the level of intracellular Ca2+.

In other some embodiments, said determining is through the use of a Melanophore assay.

In other some embodiments, said determining is through the measurement of the level of a second messenger selected from the group consisting of cyclic AMP (cAMP), cyclic GMP (cGMP), inositol 1,4,5-triphosphate (IP3), diacylglycerol (DAG), MAP kinase activity. MAPK/ERK kinase kinase-1 (MEKK1) activity, and Ca2+. In some preferred embodiments, said second messenger is IP3. In some preferred embodiments, the level of IP3 is reduced. In some preferred embodiments, the level of cardiomyocyte IP3 is reduced. In some embodiments, said second messenger is MEKK1 activity. In some embodiments, the level of MEKK1 activity is reduced. In some embodiments, the level of cardiomyocyte MEKK1 activity is reduced. In some preferred embodiments, said second messenger is Ca2+ In some preferred embodiments, the level of intracellular Ca2+ is reduced. In some preferred embodiments, the level of cardiomyocyte Ca2+ is reduced. In some embodiments, said Ca2+ measurement is carried out by FLIPR.

In some embodiments, said determining is carried out with membrane comprising said GPCR. In some embodiments, said membrane is made by homogenization of the cells with a Brinkman Polytron™. In some embodiments, said membrane preparation is made by homogenization with 3 bursts of 10-20 sec duration each of said polytron.

In some embodiments, said determining is through the measurement of a activity mediated by a reduction in intracellular IP3 level. In some embodiments, said activity is inhibition of cardiomyocyte hypertrophy.

In some embodiments, said determining is through AP1-reporter assay. In other some embodiments, said determining is through SRF reporter assay. In some embodiments, said reporter is luciferase. In some embodiments, said reporter is fi-galactosidase.

In some embodiments, said recombinant host cell further comprises promiscuous G15 or G16 alpha subunit and said determining is through measurement of intracellular Ca2+. In some embodiments, said Ca2+ measurement is carried out by FLIPR.

In some embodiments, said recombinant host cell further comprises promiscuous G15 or G16 subunit and said determining is through measurement of intracellular IP3.

In some preferred embodiments, said determining is through the measurement of GTPγS binding to membrane comprising said GPCR. In some preferred embodiments, said GTPγS is labeled with [$^{35}$S]. In some preferred embodiments, said GTPγS binding to membrane comprising said GPCR is reduced.

In some embodiments, said method further comprises the step of comparing the modulation of the receptor caused by the candidate compound to a second modulation of the receptor caused by contacting the receptor with a known modulator of the receptor. In some embodiments, said known modulator is an inverse agonist or an antagonist.

In some embodiments, the candidate compound is not a polypeptide.

In some embodiments, the candidate compound is not an antibody or an antigen-binding fragment thereof.

In some embodiments, the candidate compound is a small molecule.

In some embodiments, the candidate compound is a small molecule, with the proviso that the small molecule is pot a polypeptide.

In some embodiments, the candidate compound is a small molecule, with the proviso that the small molecule is not an antibody or an antigen-binding fragment thereof.

In some embodiments, the candidate compound is a polypeptide, with the proviso that the polypeptide is not an antibody or an antigen-binding fragment thereof.

In some embodiments, the candidate compound is a lipid.

In some embodiments, the candidate compound is an antibody or an antigen-binding fragment thereof.

In some embodiments, said method further comprises synthesis of said identified modulator.

In some embodiments, said method further comprises:
  optionally, determining the structure of the compound; and
  providing the compound or modulator or the name or structure of the compound.

In some embodiments, said method further comprises:
  optionally, determining the structure of the compound;
  optionally, providing the name or structure of the compound; and producing or synthesizing the compound.

In a second aspect, the invention features a modulator of a GPCR identified according to a method of the first aspect or screened according to the twenty-third aspect.

In some embodiments, said modulator is selected from the group consisting of agonist, partial agonist, inverse agonist and antagonist. In some preferred embodiments, said modulator is an inverse agonist or an antagonist.

In some embodiments, said modulator is an inverse agonist or an antagonist of RUP40 GPCR having the amino acid sequence of SEQ ID NO:2 with an IC50 of less than 100 μM, of less than 10 μM, or of less than 1 μM. In some embodiments, said modulator is an inverse agonist or an antagonist with an IC50 of less than a value selected from the interval of 1 μM to 100 μM. In some embodiments, said modulator is an inverse agonist or an antagonist with an IC50 of less than a value selected from the interval of 1 μM to 10 μM. In some embodiments, said modulator is an inverse agonist or an antagonist with an IC50 of less than 100 μM, of less than 10 μM, or of less than 1 μM in GTPγS binding assay carried out with membrane from transiently or stably transfected CHO cells, in pigment dispersion assay carried out in transiently transfected melanophores, or by IP3 assay in adenovirus infected cardiomyocytes expressing recombinant RUP40 GPCR polypeptide having the amino acid sequence of SEQ ID NO:2. In some embodiments, said modulator is an inverse agonist or antagonist with an IC50 of less than 100 μM in said assay. In some embodiments, said modulator is an inverse agonist or an antagonist with an IC50 of less than 90 μM in said assay. In some embodiments, said modulator is an inverse agonist or an antagonist with an IC50 of less than 80 μM in said assay. In some embodiments, said modulator is an inverse agonist or an antagonist with an IC50 of less than 70 μM in said assay. In some embodiments, said modulator is an inverse agonist or an antagonist with an IC50 of less than 60 μM in said assay. In some embodiments, said modulator is an inverse agonist or an antagonist with an IC50 of less than 50 μM in said assay. In some embodiments, said modulator is an inverse agonist or an antagonist with an IC50 of less than 40 μM in said assay. In some embodiments, said modulator is an inverse agonist or an antagonist with an IC50 of less than 30 μM in said assay. In some embodiments, said modulator is an inverse agonist or an antagonist with an IC50 of less than 20 μM in said assay. In some embodiments, said modulator is an inverse agonist or an antagonist with an IC50 of less than 10 μM in said assay. In some embodiments, said Modulator is an inverse agonist or an antagonist with an IC50 of less than 9 μM in said assay. In some embodiments, said modulator is an inverse agonist or an antagonist with an IC50 of less than 8 μM in said assay. In some embodiments, said modulator is an inverse agonist or an antagonist with an IC50 of less than 7 μM in said assay. In some embodiments, said modulator is an inverse agonist or an antagonist with an IC50 of less than 6 μM in said assay. In some embodiments, said modulator is an inverse agonist or an antagonist with an IC50 of less than 5 μM in said assay. In some embodiments, said modulator is an inverse agonist or an antagonist with an IC50 of less than 4 μM in said assay. In some embodiments, said modulator is an inverse agonist or an antagonist with an IC50 of less than 3 μM in said assay. In some embodiments, said modulator is an inverse agonist or an antagonist with an IC50 of less than 2 μM in said assay. In some embodiments, said modulator is an inverse agonist or an antagonist with an IC50 of less than 1 μM in said assay. In some embodiments, said modulator is an inverse agonist or an antagonist with an IC50 in said assay of less than a value selected from the interval of 1 μM to 100 μM. In some embodiments, said modulator is an inverse agonist or an antagonist with an IC50 in said assay of less than a value selected from the interval of 1 μM to 10 μM. In some embodiments, said inverse agonist or antagonist is an inverse agonist. In some embodiments, said inverse agonist or antagonist is an antagonist.

In some embodiments, said modulator is selective for the GPCR.

In some embodiments, said modulator is a modulator of a heart disease. In some embodiments, said heart disease is congestive heart failure. In some embodiments, said heart disease is hypertrophic cardiomyopathy. In some embodiments, said modulator is a modulator of cardiomyocyte hypertrophy.

In some embodiments, said modulator is orally bioavailable. In some embodiments, said oral bioavailability can be shown to be at least 1%, at least 5%, at least 10%, at least 15%, at least 20%, at least 25%, at least 30%, at least 35%, at least 40%, or at least 45% relative to intraperitoneal administration. In some embodiments, said oral bioavailablity can be shown to be at least 1%, at least 5%, at least 10%, or at least 15% relative to intraperitoneal administration. In some embodiments, said oral bioavailability can be shown to be at least 1%, at least 5%, at least 10%, at least 15%, at least 20%, at least 25%, at least 30%, at least 35%, at least 40%, or at least 45% relative to intravenous administration. In some embodiments, said oral bioavailablity can be shown to be at least 1%, at least 5%, at least 10%, or at least 15% relative to intravenous administration.

In some embodiments, said modulator is not a polypeptide.

In some embodiments, said modulator is not an antibody or an antigen-binding fragment thereof.

In some embodiments, said modulator is a small molecule.

In some embodiments, said modulator is a small molecule, with the proviso that the small molecule is not a polypeptide.

In some embodiments, said modulator is a small molecule, with the proviso that the small molecule is not an antibody or an antigen-binding fragment thereof.

In some embodiments, said modulator is a polypeptide, with the proviso that the polypeptide is not an antibody or an antigen-binding fragment thereof.

In some embodiments, said modulator is a lipid.

In some embodiments, said modulator is an antibody or an antigen-binding fragment thereof.

In a third aspect, the invention features a method of modulating the activity of a RUP40 GPCR, wherein the receptor couples to a G protein, said receptor comprising an amino acid sequence selected from the group consisting of:
(a) amino acids 1-1,346 of SEQ ID NO:2;
(b) amino acids 1-990 of SEQ ID NO:2;
(c) amino acids 991-1,346 of SEQ ID NO:2;
(d) amino acids 954-997 of SEQ ID NO:2;
(e) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8
(f) amino acids 1-1,349 of SEQ ID NO:4;
(g) amino acids 1-993 of SEQ ID NO:4;
(h) amino acids 994-1,349 of SEQ ID NO:4;
(i) amino acids 954-1000 of SEQ ID NO:4; and
(j) amino acids 1-141 of SEQ ID NO:6;
or a biologically active fragment of the amino acid sequence of SEQ ID NO:2 or 4; or a constitutively activated mutant of the amino acid sequence of SEQ ID NO:2 or 4 or said biologically active fragment thereof;
comprising the step of contacting the receptor with the modulator of the second aspect In some embodiments, said biologically active fragment of RUP40 GPCR of SEQ ID NO:2 or 4 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, n1=2, n2=994, and c=1,349 for RUP40 GPCR of SEQ ID NO:4. In some embodiments, said biologically active fragment of RUP40 GPCR is selected from amino acids 2-1,346,22-1,346,227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, said biologically active fragment of RUP40 GPCR is selected from amino acids 2-1,349,25-1,349,224-1,349, and 994-1,349 of SEQ ID NO:4, where amino acid 25 is understood to be the approximate site of predicted signal peptide cleavage, amino acid 224 is understood to be the approximate site of predicted proteolytic cleavage within the SEA module, and amino acid 994 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2. In some embodiments, n1=25, n2=994, and c=1,349 for RUP40 GPCR of SEQ ID NO:4. In some embodiments, n1=224, n2=994, and c=1,349 for RUP40 GPCR of. SEQ ID NO:4.

Methods of making a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2, 4, or 6 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 801 of SEQ ID NO:2, or comprising a substitution of methionine for threonine at amino acid position 856 of SEQ ID NO:2 is envisioned to be within the scope of the invention. In some embodiments, an allelic variant of RUP40 GPCR of SEQ ID NO:2 is the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8.

Mammalian orthologs of human RUP40 GPCR of SEQ ID NO:2 are envisioned to be within the scope of the invention. In some embodiments, said mammalian ortholog encompasses mouse RUP40, rat RUP40, pig RUP40, and non-human primate RUP40.

Variants of said RUP40 GPCR comprising an amino acid sequence at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to any of (a) to (j) are envisioned to be within the scope of the invention.

In some embodiments, said RUP40 GPCR comprises heterologous amino acid sequence. In some embodiments, said heterologous amino acid sequence is an epitope tag. In some embodiments, said epitope tag is hemagglutinin (HA) epitope tag. In some embodiments, said epitope tag is c-myc epitope tag. In some embodiments, said epitope tag is V5 epitope tag.

In some embodiments, said receptor further comprises proteolytic cleavage of a signal peptide.

In some embodiments, said receptor further comprises proteolytic cleavage within an SEA module.

In some embodiments, said receptor further comprises proteolytic cleavage within a GPS domain.

In some embodiments, said G-protein is Gq.

In some embodiments, said G-protein elevates intracellular IP3 levels.

In some embodiments, said modulator is an inverse agonist. In some embodiments, said modulator is an antagonist.

In some embodiments, said modulator is a modulator of a heart disease. In some embodiments, said heart disease is congestive heart failure. In some embodiments, said heart disease is hypertrophic cardiomyopathy. In some embodiments, said modulator is a modulator of cardiomyocyte hypertrophy.

In some embodiments, said modulator is selective for the GPCR.

In some embodiments, said modulator is an inverse agonist or an antagonist of RUP40 GPCR having the amino acid sequence of SEQ ID NO:2 with an IC50 of less than 100 µM, of less than 10 µM, or of less than 1 µM. In some embodiments, said modulator is an inverse agonist or an antagonist with an IC50 of less than a value selected from the interval of 1 µM to 100 µM. In some embodiments, said modulator is an inverse agonist or an antagonist with an IC50 of less than a value selected from the interval of 1 µM to 10 µM. In some embodiments, said modulator is an inverse agonist or an antagonist with an IC50 of less than 100 µM, of less than 10 µM, or of less than 1 µM in GTPγS binding assay carried out with membrane from transiently or stably transfected CHO cells, in pigment dispersion assay carried out in transiently transfected melanophores, or by IP3 assay in adenovirus infected cardiomyocytes expressing recombinant RUP40 GPCR polypeptide having the amino acid sequence of SEQ ID NO:2. In some embodiments, said modulator is an inverse agonist or antagonist with an IC50 of less than 100 µM in said assay. In some embodiments, said modulator is an inverse agonist or an antagonist with an IC50 of less than 90 µM in said assay. In some embodiments, said modulator is an inverse agonist or an antagonist with an IC50 of less than 80 µM in said assay. In some embodiments, said modulator is an inverse agonist or an antagonist with an IC50 of less than 70 µM in said assay. In some embodiments, said modulator is an inverse agonist or an antagonist with an IC50 of less than 60 µM in said assay. In some embodiments, said modulator is an inverse agonist or an antagonist with an IC50 of less than 50 µM in said assay. In some embodiments, said modulator is an inverse agonist or an antagonist with an IC50 of less than 40 µM in said assay. In some embodiments, said modulator is an inverse agonist or an antagonist with an IC50 of less than 30 µM in said assay. In some embodiments, said modulator is an inverse agonist or an antagonist with an IC50 of less than 20 µM in said assay. In some embodiments, said modulator is an inverse agonist or an antagonist with an IC50 of less than 10 µM in said assay. In some embodiments, said modulator is an inverse agonist or an antagonist with an IC50 of less than 9 µM in said assay. In some embodiments, said modulator is an inverse agonist or an antagonist with an IC50 of less than 8 µM in said assay. In some embodiments, said modulator is an inverse agonist or an antagonist with an IC50 of less than 7 AM in said assay. In some embodiments, said modulator is an inverse agonist or an antagonist with an IC50 of less than 6 µM in said assay. In some embodiments, said modulator is an inverse agonist or an antagonist with an IC50 of less than 5 µM in said assay. In some embodiments, said modulator is an inverse agonist or an antagonist with an IC50 of less than 4 µM in said assay. In some embodiments, said modulator is an inverse agonist or an antagonist with an IC50 of less than 3 µM in said assay. In some embodiments, said modulator is an inverse agonist or an antagonist with an IC50 of less than 2 µM in said assay. In some embodiments, said modulator is an inverse agonist or an antagonist with an IC50 of less than 1 µM in said assay. In some embodiments, said modulator is an inverse agonist or an antagonist with an IC50 in said assay of less than a value selected from the interval of 1 µM to 100 µM. In some embodiments, said modulator is an inverse agonist or an antagonist with an IC50 in said assay of less than a value selected from the interval of 1 µM to 10 µM. In some embodiments, said inverse agonist or antagonist is an inverse agonist. In some embodiments, said inverse agonist or antagonist is an antagonist.

In other some embodiments, said contacting comprises administration of the modulator to a membrane comprising the receptor.

In other some embodiments, said contacting comprises administration of the modulator to a cell comprising the receptor.

In other some embodiments, said contacting comprises administration of the modulator to a tissue comprising the receptor.

In other some embodiments, said contacting comprises administration of the modulator to an individual comprising the receptor. In more some embodiments, said individual is a mammal. In other more some embodiments, said mammal is a horse, cow, sheep, pig, cat, dog, rabbit, mouse, rat, non-human primate or human. Yet more preferred is mouse, rat, non-human primate or human. Most preferred is human.

In some embodiments, said modulator is orally bioavailable. In some embodiments, said oral bioavailability can be shown to be at least 1%, at least 5%, at least 10%, at least 15%, at least 20%, at least 25%, at least 30%, at least 35%, at least 40%, or at least 45% relative to intraperitoneal administration. In some embodiments, said oral bioavailablity can be shown to be at least 1%, at least 5%, at least 10%, or at least 15% relative to intraperitoneal administration. In some embodiments, said oral bioavailability can be shown to be at least 1%, at least 5%, at least 10%, at least 15%, at least 20%, at least 25%, at least 30%, at least 35%, at least 40%, or at least 45% relative to intravenous administration. In some embodiments, said oral bioavailablity can be shown to be at least 1%, at least 5%, at least 10%, or at least 15% relative to intravenous administration.

In some embodiments, said administration is oral.

In some embodiments, said individual is in need of prevention of or treatment for a cardiovascular disorder.

In some embodiments, said cardiovascular disorder is heart disease. Heart disease includes but is not limited to congestive heart failure, congestive cardiomyopathy, heart hypertrophy, left ventricular hypertrophy, right ventricular hypertrophy, post-infarction heart rupture, ventricular septal rupture, endocarditis (including bacterial), heart aneurysm, pulmonary heart disease, rheumatic heart disease, and ventricular dysfunction. Heart disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Heart disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy. In some embodiments, said modulator is an inverse agonist or an antagonist.

In some embodiments, said cardiovascular disorder is hypertrophic cardiomyopathy. In some embodiments, said hypertrophic cardiomyopathy results from a hemodynamic disorder. In some embodiments, said hypertrophic cardiomyopathy results from a genetic disorder. In some embodiments, said modulator is an inverse agonist or an antagonist.

In some embodiments, said individual is in need of prevention of or treatment for a hypertrophic cardiomyopathy resulting from a disorder selected from the group consisting of:
  (a) post-myocardial infarction remodeling,
  (b) cardiac valve disease;
  (c) sustained cardiac afterload;
  (d) myocarditis; and
  (e) familial hypertrophic cardiomyopathy.
In some embodiments, said modulator is an inverse agonist or an antagonist.

In some embodiments, said cardiovascular disorder is a congenital heart defect. Congenital heart defect includes but is not limited to aortic coarctation, aortopulmonary septal defect, trilogy of Fallot, ventricular heart septal defect, and familial hypertrophic cardiomyopathy. In some embodiments, said modulator is an inverse agonist or an antagonist.

In some embodiments, said individual is in need of prevention of or treatment for a disorder presenting with enlarged heart. In some embodiments, said modulator is an inverse agonist or an antagonist.

In a fourth aspect, the invention features a method of prevention of or treatment for a cardiovascular disorder in an individual in need of said prevention or treatment, comprising contacting a therapeutically effective amount of a modulator of the second aspect with a RUP40 GPCR, said receptor comprising an amino acid sequence selected from the group consisting of:
  (a) amino acids 1-1,346 of SEQ ID NO:2;
  (b) amino acids 1-990 of SEQ ID NO:2;
  (c) amino acids 991-1,346 of SEQ ID NO:2;
  (d) amino acids 954-997 of SEQ ID NO:2;
  (e) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
  (f) amino acids 1-1,349 of SEQ ID NO:4;
  (g) amino acids 1-993 of SEQ ID NO:4;
  (h) amino acids 994-1,349 of SEQ ID NO:4;
  (i) amino acids 954-1000 of SEQ ID NO:4; and
  (j) amino acids 1-141 of SEQ ID NO:6;
or a biologically active fragment of the amino acid sequence of SEQ ID NO:2 or 4; or a constitutively activated mutant of the amino acid sequence of SEQ ID NO:2 or 4 or said biologically active fragment thereof.

In some embodiments, said biologically active fragment of RUP40 GPCR of SEQ ID NO:2 or 4 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, n1=2, n2=994, and c=1,349 for RUP40 GPCR of SEQ ID NO:4. In some embodiments, said biologically active fragment of RUP40 GPCR is selected from amino acids 2-1,346,22-1,346,227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, said biologically active fragment of RUP40 GPCR is selected from amino acids 2-1,349,25-1,349,224-1,349, and 994-1,349 of SEQ ID NO:4, where amino acid 25 is understood to be the approximate site of predicted signal peptide cleavage, amino acid 224 is understood to be the approximate site of predicted proteolytic cleavage within the SEA module, and amino acid 994 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2. In some embodiments, n1=25, n2=994, and c=1,349 for RUP40 GPCR of SEQ ID NO:4. In some embodiments, n1=224, n2=994, and c=1,349 for RUP40 GPCR of SEQ ID NO:4.

Methods of making a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2, 4 or 6 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 801 of SEQ ID NO:2, or comprising a substitution of methionine for threonine at amino acid position 856 of SEQ ID NO:2 is envisioned to be within the scope of the invention. In some embodiments, an allelic variant of RUP40 GPCR of SEQ ID NO:2 is the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8.

Mammalian orthologs of human RUP40 GPCR of SEQ ID NO:2 are envisioned to be within the scope of the invention. In some embodiments, said mammalian ortholog encompasses mouse RUP40, rat RUP40, pig RUP40, and non-human primate RUP40.

Variants of said RUP40 GPCR comprising an amino acid sequence at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to any of (a) to (j) are envisioned to be within the scope of the invention.

In some embodiments, said modulator is selective for the GPCR.

In some embodiments, said modulator is orally bioavailable. In some embodiments, said oral bioavailability can be shown to be at least 1%, at least 5%, at least 10%, at least 15%, at least 20%, at least 25%, at least 30%, at least 35%, at least 40%, or at least 45% relative to intraperitoneal administration. In some embodiments, said oral bioavailablity can be shown to be at least 1%, at least 5%, at least 10%, or at least 15% relative to intraperitoneal administration. In some embodiments, said oral bioavailability can be shown to be at least 1%, at least 5%, at least 10%, at least 15%, at least 20%, at least 25%, at least 30%, at least 35%, at least 40%, or at least 45% relative to intravenous administration. In some embodiments, said oral bioavailablity can be shown to be at least 1%, at least 5%, at least 10%, or at least 15% relative to intravenous administration.

In some embodiments, said modulator is a modulator of a heart disease. In some embodiments, said heart disease is congestive heart failure. In some embodiments, said heart disease is hypertrophic cardiomyopathy. In some embodiments, said modulator is a modulator of cardiomyocyte hypertrophy.

In some embodiments, said modulator is an inverse agonist or an antagonist.

In some embodiments, said modulator is an inverse agonist or an antagonist of RUP40 GPCR having the amino acid sequence of SEQ ID NO:2 with an IC50 of less than 100 µM, of less than 10 µM, or of less than 1 µM. In some embodiments, said modulator is an inverse agonist or an antagonist with an IC50 of less than a value selected from the interval of 1 µM to 100 µM. In some embodiments, said modulator is an inverse agonist or an antagonist with an IC50 of less than a value selected from the interval of 1 µM to 10 µM. In some embodiments, said modulator is an inverse agonist or an antagonist with an IC50 of less than 100 µM, of less than 10 µM, or of less than 1 µM in GTPγS binding assay carried out with membrane from transiently or stably transfected CHO cells, in pigment dispersion assay carried out in transiently transfected melanophores, or by IP3 assay in adenovirus infected cardiomyocytes expressing recombinant RUP40 GPCR polypeptide having the amino acid sequence of SEQ ID NO:2. In some embodiments, said modulator is an inverse agonist or antagonist with an IC50 of less than 100 µM in said assay. In some embodiments, said modulator is an inverse agonist or an antagonist with an IC50 of less than 90 µM in said assay. In some embodiments, said modulator is an inverse agonist or an antagonist with an IC50 of less than 80 µM in said assay. In some embodiments, said modulator is an inverse agonist or an antagonist with an IC50 of less than 70 µM in said assay. In some embodiments, said modulator is an inverse agonist or an antagonist with an IC50 of less than 60 µM in said assay. In some embodiments, said modulator is an inverse agonist or an antagonist with an IC50 of less than 50 µM in said assay. In some embodiments, said modulator is an inverse agonist or an antagonist with an IC50 of less than 40 µM in said assay. In some embodiments, said modulator is an inverse agonist or an antagonist with an IC50 of less than 30 µM in said assay. In some embodiments, said modulator is an inverse agonist or an antagonist with an IC50 of less than 20 µM in said assay. In some embodiments, said modulator is an inverse agonist or an antagonist with an IC50 of less than 10 µM in said assay. In some embodiments, said modulator is an inverse agonist or an antagonist with an IC50 of less than 9 µM in said assay. In some embodiments, said modulator is an inverse agonist or an antagonist with an IC50 of less than 8 µM in said assay. In some embodiments, said modulator is an inverse agonist or an antagonist with an IC50 of less than 7 µM in said assay. In some embodiments, said modulator is an inverse agonist or an antagonist with an IC50 of less than 6 µM in said assay. In some embodiments, said modulator is an inverse agonist or an antagonist with an IC50 of less than 5 µM in said assay. In some embodiments, said modulator is an inverse agonist or an antagonist with an IC50 of less than 4 µM in said assay. In some embodiments, said modulator is an inverse agonist or an antagonist with an IC50 of less than 3 µM in said assay. In some embodiments, said modulator is an inverse agonist or an antagonist with an IC50 of less than 2 µM in said assay. In some embodiments, said modulator is an inverse agonist or an antagonist with an IC50 of less than 1 µM in said assay. In some embodiments, said modulator is an inverse agonist or an antagonist with an IC50 in said assay of less than a value selected from the interval of 1 µM to 100 µM. In some embodiments, said modulator is an inverse agonist or an antagonist with an IC50 in said assay of less than a value selected from the interval of 1 µM to 10 µM. In some embodiments, said inverse agonist or antagonist is an inverse agonist. In some embodiments, said inverse agonist or antagonist is an antagonist.

In some embodiments, said contacting comprises oral administration of said modulator to said individual.

In some embodiments, said individual is in need of prevention of or treatment for a cardiovascular disorder.

In some embodiments, said cardiovascular disorder is heart disease. Heart disease includes but is not limited to congestive heart failure, congestive cardiomyopathy, heart hypertrophy, left ventricular hypertrophy, right ventricular hypertrophy, post-infarction heart rupture, ventricular septal rupture, endocarditis (including bacterial), heart aneurysm, pulmonary heart disease, rheumatic heart disease, and ventricular dysfunction. Heart disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Heart disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy. In some embodiments, said modulator is an inverse agonist or an antagonist.

In some embodiments, said cardiovascular disorder is hypertrophic cardiomyopathy. In some embodiments, said hypertrophic cardiomyopathy results from a hemodynamic disorder. In some embodiments, said hypertrophic cardiomyopathy results from a genetic disorder. In some embodiments, said modulator is an inverse agonist or an antagonist.

In some embodiments, said individual is in need of prevention of or treatment for a hypertrophic cardiomyopathy resulting from a disorder selected from the group consisting of:
 (a) post-myocardial infarction remodeling;
 (b) cardiac valve disease;
 (c) sustained cardiac afterload;
 (d) myocarditis; and
 (e) familial hypertrophic cardiomyopathy.

In some embodiments, said modulator is an inverse agonist or an antagonist.

In some embodiments, said cardiovascular disorder is congenital heart defect. Congenital heart defect includes but is not limited to aortic coarctation, aortopulmonary septal defect, trilogy of Fallot, ventricular heart septal defect, and familial hypertrophic cardiomyopathy. In some embodiments, said modulator is an inverse agonist or an antagonist.

In some embodiments, said individual is in need of prevention of or treatment for a disorder presenting with enlarged heart. In some embodiments, said modulator is an inverse agonist or an antagonist.

In some embodiments, said individual is a mammal. In more some embodiments, said mammal is a horse, cow, sheep, pig, cat, dog, rabbit, mouse, rat, non-human primate or human. Yet more preferred is mouse, rat, non-human primate or human. Most preferred is human.

In a fifth aspect, the invention features a method of preparing a composition which comprises identifying a modulator of a RUP40 GPCR and then admixing a carrier and the modulator, wherein the modulator is identifiable by a method of the first aspect.

In some embodiments, said modulator is selected from the group consisting of agonist, partial agonist, inverse agonist and antagonist. In some embodiments, said modulator is an inverse agonist or an antagonist.

In some embodiments, said modulator is an inverse agonist or an antagonist of RUP40 GPCR having the amino acid sequence of SEQ ID NO:2 with an IC50 of less than 100 µM, of less than 10 µM, or of less than 1 µM. In some embodiments, said modulator is an inverse agonist or an antagonist with an IC50 of less than a value selected from the interval of 1 µM to 100 µM. In some embodiments, said modulator is an inverse agonist or an antagonist with an IC50 of less than a value selected from the interval of 1 µM to 10 µM. In some embodiments, said modulator is an inverse agonist or an antagonist with an IC50 of less than 100 µM, of less than 10 µM, or of less than 1 µM in GTPγS binding assay carried out with membrane from transiently or stably transfected CHO cells, in pigment dispersion assay carried out in transiently transfected melanophores, or by IP3 assay in adenovirus infected cardiomyocytes expressing recombinant RUP40 GPCR polypeptide having the amino acid sequence of SEQ ID NO:2. In some embodiments, said modulator is an inverse agonist or antagonist with an IC50 of less than 100 µM in said assay. In some embodiments, said modulator is an inverse agonist or an antagonist with an IC50 of less than 90 µM in said assay. In some embodiments, said modulator is an inverse agonist or an antagonist with an IC50 of less than 80 µM in said assay. In some embodiments, said modulator is an inverse agonist or an antagonist with an IC50 of less than 70 µM in said assay. In some embodiments, said modulator is an inverse agonist or an antagonist with an IC50 of less than 60 µM in said assay. In some embodiments, said modulator is an inverse agonist or an antagonist with an IC50 of less than 50 µM in said assay. In some embodiments, said modulator is an inverse agonist or an antagonist with an IC50 of less than 40 µM in said assay. In some embodiments, said modulator is an inverse agonist or an antagonist with an IC50 of less than 30 µM in said assay. In some embodiments, said modulator is an inverse agonist or an antagonist with an IC50 of less than 20 µM in said assay. In some embodiments, said modulator is an inverse agonist or an antagonist with an IC50 of less than 10 µM in said assay. In some embodiments, said modulator is an inverse agonist or an antagonist with an IC50 of less than 9 µM in said assay. In some embodiments, said modulator is an inverse agonist or an antagonist with an IC50 of less than 8 µM in said assay. In some embodiments, said modulator is an inverse agonist or an antagonist with an IC50 of less than 7 µM in said assay. In some embodiments, said modulator is an inverse agonist or an antagonist with an IC50 of less than 6 µM in said assay. In some embodiments, said modulator is an inverse agonist or an antagonist with an IC50 of less than 5 µM in said assay. In some embodiments, said modulator is an inverse agonist or an antagonist with an IC50 of less than 4 µM in said assay. In some embodiments, said modulator is an inverse agonist or an antagonist with an IC50 of less than 3 µM in said assay. In some embodiments, said modulator is an inverse agonist or an antagonist with an IC50 of less than 2 µM in said assay. In some embodiments, said modulator is an inverse agonist or an antagonist with an IC50 of less than 1 µM in said assay. In some embodiments, said modulator is an inverse agonist or an antagonist with an IC50 in said assay of less than a value selected from the interval of 1 µM to 100 µM. In some embodiments, said modulator is an inverse agonist or an antagonist with an IC50 in said assay of less than a value selected from the interval of 1 µM to 10 µM. In some embodiments, said inverse agonist or antagonist is an inverse agonist. In some embodiments, said inverse agonist or antagonist is an antagonist.

In some embodiments, said modulator is selective for the GPCR.

In some embodiments, said modulator is a modulator of a heart disease. In some embodiments, said heart disease is congestive heart failure. In some embodiments, said heart disease is hypertrophic cardiomyopathy. In some embodiments, said modulator is a modulator of cardiomyocyte hypertrophy.

In some embodiments, said modulator is orally bioavailable. In some embodiments, said oral bioavailability can be shown to be at least 1%, at least 5%, at least 10%, at least 15%, at least 20%, at least 25%, at least 30%, at least 35%, at least 40%, or at least 45% relative to intraperitoneal administration. In some embodiments, said oral bioavailablity can be shown to be at least 1%, at least 5%, at least 10%, or at least 15% relative to intraperitoneal administration. In some embodiments, said oral bioavailability can be shown to be at least 1%, at least 5%, at least 10%, at least 15%, at least 20%, at least 25%, at least 30%, at least 35%, at least 40%, or at least 45% relative to intravenous administration. In some embodiments, said oral bioavailablity can be shown to be at least 1%, at least 5%, at least 10%, or at least 15% relative to intravenous administration.

In some embodiments, said modulator identifiable by the method of the first aspect is identified by a method of the first aspect.

In a sixth aspect, the invention features a pharmaceutical or physiologically acceptable composition comprising, consisting essentially of, or consisting of the modulator of the second aspect. In some embodiments, said modulator is an inverse agonist or an antagonist. In some embodiments, the pharmaceutical or physiologically acceptable composition is a pharmaceutical composition. In some embodiments, the pharmaceutical or physiologically acceptable composition is a physiologically acceptable composition. In some embodiments, the pharmaceutical or physiologically acceptable composition comprises a modulator according to the second aspect. In some embodiments, the pharmaceutical or physiologically acceptable composition consists essentially of a modulator according to the second aspect. In some embodiments, the pharmaceutical or physiologically acceptable composition consists of a modulator according to the second aspect. In some embodiments, said modulator is an inverse agonist. In some embodiments, said modulator is an antagonist.

In some embodiments, said modulator is selective for the GPCR.

In some embodiments, said modulator is orally bioavailable. In some embodiments, said oral bioavailability can be shown to be at least 1%, at least 5%, at least 10%, at least 15%, at least 20%, at least 25%, at least 30%, at least 35%, at least 40%, or at least 45% relative to intraperitoneal administration. In some embodiments, said oral bioavailablity can be shown to be at least 1%, at least 5%, at least 10%, or at, least 15% relative to intraperitoneal administration. In some embodiments, said oral bioavailability can be shown to be at least 1%, at least 5%, at least 10%, at least 15%, at least 20%, at least 25%, at least 30%, at least 35%, at least 40%, or at least 45% relative to intravenous administration. In some embodiments, said oral bioavailablity can be shown to be at least 1%, at least 5%, at least 10%, or at least 15% relative to intravenous administration.

In some embodiments, said modulator is a modulator of a heart disease. In some embodiments, said heart disease is congestive heart failure. In some embodiments, said heart disease is hypertrophic cardiomyopathy. In some embodiments, said modulator is a modulator of cardiomyocyte hypertrophy.

In some embodiments, said modulator is an inverse agonist or an antagonist.

In some embodiments, said modulator is an inverse agonist or an antagonist of RUP40 GPCR having the amino acid sequence of SEQ ID NO:2 with an IC50 of less than 100 µM, of less than 10 µM, or of less than 1 µM. In some embodiments, said modulator is an inverse agonist or an antagonist with an IC50 of less than a value selected from the interval of 1 µM to 100M. In some embodiments, said modulator is an inverse agonist or an antagonist with an IC50 of less than a value selected from the interval of 1 µM to 10 µM. In some embodiments, said modulator is an inverse agonist or an antagonist with an IC50 of less than 100 µM, of less than 10 µM, or of less than 1 µM in GTPγS binding assay carried out with membrane from transiently or stably transfected CHO cells, in pigment dispersion assay carried out in transiently transfected melanophores, or by IP3 assay in adenovirus infected cardiomyocytes expressing recombinant RUP40 GPCR polypeptide having the amino acid sequence of SEQ ID NO:2. In some embodiments, said modulator is an inverse agonist or antagonist with an IC50 of less than 100 µM in said assay. In some embodiments, said modulator is an inverse agonist or antagonist with an IC50 of less than 90 µM in said assay. In some embodiments, said modulator is an inverse agonist or antagonist with an IC50 of less than 80 µM in said assay. In some embodiments, said modulator is an inverse agonist or an antagonist with an IC50 of less than 70 µM in said assay. In some embodiments, said modulator is an inverse agonist or an antagonist with an IC50 of less than 60 µM in said assay. In some embodiments, said modulator is an inverse agonist or an antagonist with an IC50 of less than 50 µM in said assay. In some embodiments, said modulator is an inverse agonist or an antagonist with an IC50 of less than 40 µM in said assay. In some embodiments, said modulator is an inverse agonist or an antagonist with an IC50 of less than 30 µM in said assay. In some embodiments, said modulator is an inverse agonist or an antagonist with an IC50 of less than 20 µM in said assay. In some embodiments, said modulator is an inverse agonist or an antagonist with an IC50 of less than 10 µM in said assay. In some embodiments, said modulator is an inverse agonist or an antagonist with an IC50 of less than 9 µM in said assay. In some embodiments, said modulator is an inverse agonist or an antagonist with an IC50 of less than 8 µM in said assay. In some embodiments, said modulator is an inverse agonist or an antagonist with an IC50 of less than 7 µM in said assay. In some embodiments, said modulator is an inverse agonist or an antagonist with an IC50 of less than 6 µM in said assay. In some embodiments, said modulator is an inverse agonist or an antagonist with an IC50 of less than 5 µM in said assay. In some embodiments, said modulator is an inverse agonist or an antagonist with an IC50 of less than 4 µM in said assay. In some embodiments, said modulator is an inverse agonist or an antagonist with an IC50 of less than 3 µM in said assay. In some embodiments, said modulator is an inverse agonist or an antagonist with an IC50 of less than 2 µM in said assay. In some embodiments, said modulator is an inverse agonist or an antagonist with an IC50 of less than 1 µM in said assay. In some embodiments, said modulator is an inverse agonist or an antagonist with an IC50 in said assay of less than a value selected from the interval of 1 µM to 100 µM. In some embodiments, said modulator is an inverse agonist or an antagonist with an IC50 in said assay of less than a value selected from the interval of 1 µM to 10 µM. In some embodiments, said inverse agonist or antagonist is an inverse agonist. In some embodiments, said inverse agonist or antagonist is an antagonist.

In a seventh aspect, the invention features a method of prevention of or treatment for a cardiovascular disorder, comprising providing or administering to an individual in need of said prevention or treatment said pharmaceutical or physiologically acceptable composition of the sixth aspect.

In some embodiments, said cardiovascular disorder is heart disease. Heart disease includes but is not limited to congestive heart failure, congestive cardiomyopathy, heart hypertrophy, left ventricular hypertrophy, right ventricular hypertrophy, post-infarction heart rupture, ventricular septal rupture, endocarditis (including bacterial), heart aneurysm, pulmonary heart disease, rheumatic heart disease, and ventricular dysfunction. Heart disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Heart disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy. In some embodiments, said modulator is an inverse agonist or an antagonist.

In some embodiments, said cardiovascular disorder is hypertrophic cardiomyopathy. In some embodiments, said hypertrophic cardiomyopathy results from a hemodynanaic disorder. In some embodiments, said hypertrophic cardiomyopathy results from a genetic disorder. In some embodiments, said modulator is an inverse agonist or an antagonist.

The invention also relates to a method of prevention of or treatment for a hypertrophic cardiomyopathy comprising providing or administering to an individual in need of said prevention or treatment said pharmaceutical or physiologically acceptable composition of the sixth aspect, said hypertrophic cardiomyopathy resulting from a disorder selected from the group consisting of:
  (a) post-myocardial infarction remodeling,
  (b) cardiac valve disease;
  (c) sustained cardiac afterload;
  (d) myocarditis; and
  (e) familial hypertrophic cardiomyopathy.
In some embodiments, said modulator is an inverse agonist or an antagonist.

In some embodiments, said cardiovascular disorder is congenital heart defect, comprising providing or administering to an individual in need of said prevention or treatment said pharmaceutical or physiologically acceptable composition of the sixth aspect. Congenital heart defect includes but is not limited to aortic coarctation, aortopulmonary septal defect, trilogy of Fallot, ventricular heart septal defect, and familial hypertrophic cardiomyopathy. In some embodiments, said modulator is an inverse agonist or an antagonist.

The invention also relates to a method of prevention of or treatment for a disorder comprising providing or administering to an individual in need of said prevention or treatment said pharmaceutical or physiologically acceptable composition of the sixth aspect, wherein said disorder presents with enlarged heart. In some embodiments, said modulator is an agonist or an inverse agonist.

In some embodiments, a therapeutically effective amount of said pharmaceutical or physiologically acceptable composition is provided or administered to said individual.

In some embodiments, said providing or administering of said pharmaceutical or physiologically acceptable composition is oral.

In some embodiments, said individual is a mammal. In more some embodiments, said mammal is a horse, cow, sheep, pig, cat, dog, rabbit, mouse, rat, non-human primate or human. Yet more preferred is mouse, rat, non-human primate or human. Most preferred is human.

In an eighth aspect, the invention features a method of using the modulator of the second aspect for the preparation of a medicament for the prevention of or treatment for a cardiovascular disorder.

In some embodiments, said modulator is selective for the GPCR.

In some embodiments, said modulator is orally bioavailable. In some embodiments, said oral bioavailability can be shown to be at least 1%, at least 5%, at least 10%, at least 15%, at least 20%, at least 25%, at least 30%, at least 35%, at least 40%, or at least 45% relative to intraperitoneal administration. In some embodiments, said oral bioavailablity can be shown to be at least 1%, at least 5%, at least 10%, or at least 15% relative to intraperitoneal administration. In some embodiments, said oral bioavailability can be shown to be at least 1%, at least 5%, at least 10%, at least 15%, at least 20%, at least 25%, at least 30%, at least 35%, at least 40%, or at least 45% relative to intravenous administration. In some embodiments, said oral bioavailablity can be shown to be at least 1%, at least 5%, at least 10%, or at least 15% relative to intravenous administration.

In some embodiments, said modulator is a modulator of a heart disease. In some embodiments, said heart disease is congestive heart failure. In some embodiments, said heart disease is hypertrophic cardiomyopathy. In some embodiments, said modulator is a modulator of cardiomyocyte hypertrophy. In some embodiments, said modulator is an inverse agonist or an antagonist.

In some embodiments, said modulator is an inverse agonist or an antagonist of RUP40 GPCR having the amino acid sequence of SEQ ID NO:2 with an IC50 of less than 100 μM, of less than 10 μM, or of less than 1 μM. In some embodiments, said modulator is an inverse agonist or an antagonist with an IC50 of less than a value selected from the interval of 1 μM to 100 μM. In some embodiments, said modulator is an inverse agonist or an antagonist with an IC50 of less than a value selected from the interval of 1 μM to 10 μM. In some embodiments, said modulator is an inverse agonist or an antagonist with an IC50 of less than 100 μM, of less than 10 μM, or of less than 1 μM in GTPγS binding assay carried out with membrane from transiently or stably transfected CHO cells, in pigment dispersion assay carried out in transiently transfected melanophores, or by IP3 assay in adenovirus infected cardiomyocytes expressing recombinant RUP40 GPCR polypeptide having the amino acid sequence of SEQ ID NO:2. In some embodiments, said modulator is an inverse agonist or antagonist with an IC50 of less than 100 μM in said assay. In some embodiments, said modulator is an inverse agonist or antagonist with an IC50 of less than 90 μM in said assay. In some embodiments, said modulator is an inverse agonist or antagonist with an IC50 of less than 80 μM in said assay. In some embodiments, said modulator is an inverse agonist or an antagonist with an IC50 of less than 70 μM in said assay. In some embodiments, said modulator is an inverse agonist or an antagonist with an IC50 of less than 60 μM in said assay. In some embodiments, said modulator is an inverse agonist or an antagonist with an IC50 of less than 50 μM in said assay. In some embodiments, said modulator is an inverse agonist or an antagonist with an IC50 of less than 40 μM in said assay. In some embodiments, said modulator is an inverse agonist or an antagonist with an IC50 of less than 30 μM in said assay. In some embodiments, said modulator is an inverse agonist or an antagonist with an IC50 of less than 20 μM in said assay. In some embodiments, said modulator is an inverse agonist or an antagonist with an IC50 of less than 10 μM in said assay. In some embodiments, said modulator is an inverse agonist or an antagonist with an IC50 of less than 9 μM in said assay. In some embodiments, said modulator is an inverse agonist or an antagonist with an IC50 of less than 8 μM in said assay. In some embodiments, said modulator is an inverse agonist or an antagonist with an IC50 of less than 7 μM in said assay. In some embodiments, said modulator is an inverse agonist or an antagonist with an IC50 of less than 6 μM in said assay. In some embodiments, said modulator is an inverse agonist or an antagonist with an IC50 of less than 5 μM in said assay. In some embodiments, said modulator is an inverse agonist or an antagonist with an IC50 of less than 4 μM in said assay. In some embodiments, said modulator is an inverse agonist or an antagonist with an IC50 of less than 3 μM in said assay. In some embodiments, said modulator is an inverse agonist or an antagonist with an IC50 of less than 2 μM in said assay. In some embodiments, said modulator is an inverse agonist or an antagonist with an IC50 of less than 1 μM in said assay. In some embodiments, said modulator is an inverse agonist or an antagonist with an IC50 in said assay of less than a value selected from the interval of 1 μM to 100 μM. In some embodiments, said modulator is an inverse agonist or an antagonist with an IC50 in said assay of less than a value selected from the interval of 1 μM to 10 μM. In some embodiments, said inverse agonist or antagonist is an inverse agonist. In some embodiments, said inverse agonist or antagonist is an antagonist.

In some embodiments, said treatment comprises oral administration of said medicament to said individual.

In some embodiments, said cardiovascular disorder is heart disease. Heart disease includes but is not limited to congestive heart failure, congestive cardiomyopathy, heart hypertrophy, left ventricular hypertrophy, right ventricular hypertrophy, post-infarction heart rupture, ventricular septal rupture, endocarditis (including bacterial), heart aneurysm, pulmonary heart disease, rheumatic heart disease, and ventricular dysfunction. Heart disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Heart disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy. In some embodiments, said modulator is an inverse agonist or an antagonist.

In some embodiments, said cardiovascular disorder is hypertrophic cardiomyopathy, comprising providing or administering to an individual in need of said prevention or treatment said pharmaceutical or physiologically acceptable composition of the sixth aspect. In some embodiments, said hypertrophic cardiomyopathy results from a hemodynamic disorder. In some embodiments, said hypertrophic cardiomyopathy results from a genetic disorder. In some embodiments, said modulator is an inverse agonist or an antagonist.

In some embodiments, said hypertrophic cardiomyopathy resulting from a disorder selected from the group consisting of:
   (a) post-myocardial infarction remodeling;
   (b) cardiac valve disease;
   (c) sustained cardiac afterload;
   (d) myocarditis; and
   (e) familial hypertrophic cardiomyopathy.
In some embodiments, said modulator is an inverse agonist or an antagonist.

In some embodiments, said cardiovascular disorder is congenital heart defect. Congenital heart defect includes but is not limited to aortic coarctation, aortopulmonary septal defect, trilogy of Fallot, ventricular heart septal defect, and familial hypertrophic cardiomyopathy. In some embodiments, said modulator is an inverse agonist or an antagonist.

In some embodiments, said individual is in need of prevention or treatment for a disorder presenting with an enlarged heart. In some embodiments, said modulator is an inverse agonist or an agonist.

In some embodiments, said individual is a mammal. In more some embodiments, said mammal is a horse, cow, sheep, pig, cat, dog, rabbit, mouse, rat, non-human primate or human. Yet more preferred is mouse, rat, non-human primate or human. Most preferred is human.

In a ninth aspect, the invention features a method of identifying whether a candidate compound is a ligand of a RUP40 GPCR, said receptor comprising an amino acid sequence selected from the group consisting of:
   (a) amino acids 1-1,346 of SEQ ID NO:2;
   (b) amino acids 1-990 of SEQ ID NO:2;
   (c) amino acids 991-1,346 of SEQ ID NO:2;
   (d) amino acids 954-997 of SEQ ID NO:2;
   (e) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
   (f) amino acids 1-1,349 of SEQ ID NO:4;
   (g) amino acids 1-993 of SEQ ID NO:4;
   (h) amino acids 994-1,349 of SEQ ID NO:4;
   (i) amino acids 954-1000 of SEQ ID NO:4; and
   (j) amino acids 1-141 of SEQ ID NO:6;
or a biologically active fragment of the amino acid sequence of SEQ ID NO:2 or 4; or a constitutively activated mutant of the amino acid sequence of SEQ ID NO:2 or 4 or said biologically active fragment thereof; comprising the steps of:
   (a) contacting the receptor with a labeled known ligand of the GPCR in the presence or absence of the candidate compound; and
   (b) determining whether the binding of said labeled known ligand is inhibited in the presence of the candidate compound;
wherein said inhibition is indicative of the candidate compound being a ligand of a RUP40 GPCR.

In some embodiments, the RUP40 GPCR is recombinant.

In some embodiments, said RUP40 GPCR comprises one or more epitope tag. In some embodiments, said epitope tag is hemagglutinin (HA) epitope tag. In some embodiments, said epitope tag is c-myc epitope tag. In some embodiments, said epitope tag is V5 epitope tag.

The invention also relates to a method of determining whether a candidate compound is a ligand of a RUP40 GPCR, comprising the steps of:
   (a) culturing RUP40 GPCR-expressing host cells under conditions that would allow expression of a recombinant RUP40 GPCR, said host cells being transfected with an expression vector comprising a polynucleotide encoding said recombinant RUP40 GPCR comprising an amino acid sequence selected from the group consisting of:
      (i) amino acids 1-1,346 of SEQ ID NO:2;
      (ii) amino acids 1-990 of SEQ ID NO:2;
      (iii) amino acids 991-1,346 of SEQ ID NO:2;
      (iv) amino acids 954-997 of SEQ ID NO:2;
      (v) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
      (vi) amino acids 1-1,349 of SEQ ID NO:4;
      (vii) amino acids 1-993 of SEQ ID NO:4;
      (viii) amino acids 994-1,349 of SEQ ID NO:4;
      (ix) amino acids 954-1000 of SEQ ID NO:4; and
      (x) amino acids 1-141 of SEQ BD NO:6; or a biologically active fragment of the amino acid sequence of SEQ ID NO:2 or 4; or a constitutively activated mutant of the amino acid sequence of SEQ ID NO:2 or 4 or said biologically active fragment thereof;
   (b) exposing a first population of RUP40 GPCR-expressing cells of step (a) to a labeled known ligand of said RUP40 GPCR;
   (c) exposing a second population of RUP40 GPCR-expressing cells of step (a) to the compound and the labeled blown ligand of said RUP40 GPCR of step (b);
   (d) determining the binding of the labeled known ligand of said RUP40 GPCR-expressing cells of step (b) and step (c); and
   (e) comparing the binding of the labeled known ligand to said RUP40 GPCR to the RUP40 GPCR-expressing cells of step (b) and step (c);
wherein inhibition of binding of the labeled known ligand of said RUP40 GPCR in the presence of the compound is indicative of the compound being a ligand of a RUP40 GPCR.

In some embodiments, said RUP40 GPCR comprises heterologous amino acid sequence. In some embodiments, said heterologous amino acid sequence is an epitope tag. In some embodiments, said epitope tag is hemagglutinin (HA) epitope tag. In some embodiments, said epitope tag is c-myc epitope tag. In some embodiments, said epitope tag is V5 epitope tag.

The invention also relates to a method of determining whether a candidate compound is a ligand of a RUP40 GPCR, comprising the steps of:
   (a) culturing RUP40 GPCR-expressing host cells under conditions that would allow expression of a recombinant RUP40 GPCR, said host cells being transfected with an expression vector comprising a polynucleotide encoding said recombinant RUP40 GPCR comprising an amino acid sequence selected from the group consisting of:
      (i) amino acids 1-1,346 of SEQ ID NO:2;
      (ii) amino acids 1-990 of SEQ ID NO:2;
      (iii) amino acids 991-1,346 of SEQ ID NO:2;
      (iv) amino acids 954-997 of SEQ ID NO:2;

(v) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
(vi) amino acids 1-1,349 of SEQ ID NO:4;
(vii) amino acids 1-993 of SEQ ID NO:4;
(viii) amino acids 9941,349 of SEQ ID NO:4;
(ix) amino acids 954-1000 of SEQ ID NO:4; and
(x) amino acids 1-141 of SEQ ID NO:6;
or a biologically active fragment of the amino acid sequence of SEQ ID NO:2 or 4; or a constitutively activated mutant of the amino acid sequence of SEQ ID NO:2 or 4 or said biologically active fragment thereof;
(b) preparing membrane from the RUP40 GPCR-expressing cells of step (a);
(c) exposing a first population of the membrane preparation of step (b) to a labeled known ligand of said RUP40 GPCR of step (b);
(d) exposing a second population of the membrane preparation of step (b) to the candidate compound and the labeled known ligand of said RUP40 GPCR;
(e) determining the binding of the labeled known ligand of said RUP40 GPCR to the membrane preparations of step (c) and step (d); and
(f) comparing the binding of the labeled known ligand of said RUP40 GPCR to the membrane preparations of step (c) and step (d);
wherein inhibition of binding of the labeled known ligand of said RUP40 GPCR in the presence of the compound is indicative of the compound being a ligand of a RUP40 GPCR.

In some embodiments, said membrane preparation is made by homogenization of the cells with a Brinkman Polytron™. In some embodiments, said membrane preparation is made by homogenization with 3 bursts of 10-20 sec duration each of said polytron.

In some embodiments, said biologically active fragment of RUP40 GPCR of SEQ ID NO:2 or 4 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, n1=2, n2=994, and c=1,349 for RUP40 GPCR of SEQ ID NO:4. In some embodiments, said biologically active fragment of RUP40 GPCR is selected from amino acids 2-1,346, 22-1,346, 227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, said biologically active fragment of RUP40 GPCR is selected from amino acids 2-1,349, 25-1,349, 224-1,349, and 994-1,349 of SEQ ID NO:4, where amino acid 25 is understood to be the approximate site of predicted signal peptide cleavage, amino acid 224 is understood to be the approximate site of predicted proteolytic cleavage within the SEA module, and amino acid 994 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2. In some embodiments, n1=25, n2=994, and c=1,349 for RUP40 GPCR of SEQ ID NO:4. In some embodiments, n1=224, n2=994, and c=1,349 for RUP40 GPCR of SEQ ID NO:4.

Methods of making a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2, 4 or 6 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 801 of SEQ ID NO:2, or comprising a substitution of methionine for threonine at amino acid position 856 of SEQ ID NO:2 is envisioned to be within the scope of the invention. In some embodiments, an allelic variant of RUP40 GPCR of SEQ ID NO:2 is the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8.

Mammalian orthologs of human RUP40 GPCR of SEQ ID NO:2 are envisioned to be within the scope of the invention. In some embodiments, said mammalian ortholog encompasses mouse RUP40, rat RUP40, pig RUP40, and non-human primate RUP40.

Variants of said RUP40 GPCR comprising an amino acid sequence at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to any of (i) to (x) are envisioned to be within the scope of the invention.

In some embodiments, said RUP40 GPCR comprises heterologous amino acid sequence. In some embodiments, said heterologous amino acid sequence is an epitope tag. In some embodiments, said epitope tag is hemagglutinin (HA) epitope tag. In some embodiments, said epitope tag is c-myc epitope tag. In some embodiments, said epitope tag is V5 epitope tag.

In some embodiments, said known ligand is the modulator of the second aspect.

In other embodiments, said known ligand is an antibody specific for the GPCR, or a derivative of said antibody.

In some embodiments, said label is selected from the group consisting of:
(a) radioisotope;
(b) enzyme; and
(c) fluorophore.

In some embodiments, said label is a radioisotope. In more some embodiments, said label is selected from the group consisting of $^3H$, $^{14}C$, $^{35}S$, and $^{125}I$.

In other embodiments, said method further comprises the step of comparing the level of inhibition of binding of a labeled first known ligand by the candidate compound to a second level of inhibition of binding of said labeled first known ligand by a second ligand known to bind to the GPCR.

In a tenth aspect, the invention features a transgenic non-human mammal comprising expression of a human RUP40 GPCR, said receptor comprising an amino acid sequence selected from the group consisting of:
(a) amino acids 1-1,346 of SEQ ID NO:2;
(b) amino acids 1-990 of SEQ ID NO:2;
(c) amino acids 991-1,346 of SEQ ID NO:2;
(d) amino acids 954-997 of SEQ ID NO:2; and
(e) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
or a biologically active fragment of the amino acid sequence of SEQ ID NO:2; or a constitutively activated mutant of the amino acid sequence of SEQ ID NO:2 or said biologically active fragment thereof.

In some embodiments, said biologically active fragment of RUP40 GPCR of SEQ ID NO:2 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, said biologically active fragment of RUP40 GPCR is selected from amino acids 2-1,346, 22-1,346, 227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2.

Methods of making a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 0.801 of SEQ ID NO:2, or comprising a substitution of methionine for threonine at amino acid position 856 of SEQ ID NO:2 is envisioned to be within the scope of the invention. In some embodiments, an allelic variant of RUP40 GPCR of SEQ ID NO:2 is the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8.

Variants of said RUP40 GPCR comprising an amino acid sequence at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to any of (a) to (d) are envisioned to be within the scope of the invention.

In some embodiments, said non-human mammal is mouse, rat, or pig.

In some embodiments, said expression of a human RUP40 GPCR is cardiomyocyte-selective.

In some embodiments, said cardiomyocyte-selective expression of said human RUP40 GPCR is conferred by alpha myosin heavy chain promoter [Subramaniam A et al., J Biol Chem (1991) 266:24613-20; the disclosure of which is hereby incorporated by reference in its entirety].

In some embodiments, said transgenic non-human mammal exhibits predisposition to or manifest congestive heart failure or hypertrophic cardiomyopathy relative to wild-type control mammal.

In an eleventh aspect, the invention features a method of using the transgenic non-human mammal of the tenth aspect, said transgenic non-human mammal exhibiting said predisposition to or manifest congestive heart failure or hypertrophic cardiomyopathy, to identify whether a modulator of the second aspect has efficacy for the prevention of or treatment for congestive heart failure or hypertrophic cardiomyopathy, comprising the steps of:
(a) administering or not administering the modulator to the transgenic non-human mammal;
(b) determining whether administration of the modulator has an effect selected from the group consisting of:
(i) reduction of wet or dry heart weight;
(ii) reduction of the wet or dry heart weight/body weight ratio;
(iii) reduction of the cross-sectional area of myocytes; and
(iv) reduction of the level of induction of ANF gene;
wherein said determination is indicative of the modulator having efficacy for the prevention of or treatment for congestive heart failure or hypertrophic cardiomyopathy.

In some embodiments, said modulator is an inverse agonist or antagonist.

In some embodiments, said mammal is mouse. In some embodiments, said mammal is rat. In some embodiments, said mammal is pig.

In a twelfth aspect, the invention features a transgenic non-human mammal comprising a disruption in a RUP40 gene. In some embodiments, the invention features a transgenic non-human mammal comprising a disruption in a RUP40 gene, wherein there is no native expression of endogenous RUP40 gene. In some embodiments, the invention features a transgenic non-human mammal comprising a cardiomyocyte-selective disruption of a RUP40 gene. In some embodiments, the invention features a transgenic non-human mammal comprising a cardiomyocyte-selective disruption of a RUP40 gene, wherein there is no native cardiomyocyte expression of endogenous RUP40 gene. Methods for assessing native expression of endogenous RUP40 gene are within the purview of those of ordinary skill in the art and include, but are not limited to, RT-PCR, Northern blot, in situ hybridization, and immunocytochemistry.

In some embodiments, said non-human mammal is mouse, rat, or pig.

In some embodiments, said cardiomyocyte-selective disruption is conferred by promoter for the ventricular specific isoform of myosin light chain 2 (mlc-2v) [Minamisawa S et al., J Biol Chem (1999) 274:10066-70; the disclosure of which is hereby incorporated by reference in its entirety].

In some embodiments, said mammal is mouse, and said RUP40 gene encodes a polypeptide comprising the amino acid sequence of SEQ ID NO:6 or an allelic variant of said amino acid sequence.

In some embodiments, said mammal is rat, and said RUP40 gene encodes a polypeptide comprising the amino acid sequence of SEQ ID NO:4 or an allelic variant of said amino acid sequence.

In some embodiments, said transgenic non-human mammal comprising a disruption in a RUP40 gene manifests reduced hypertrophic cardiomyopathy on transverse aortic constriction (TAC) relative to wild-type control mammal.

In a thirteenth aspect, the invention features an isolated polynucleotide comprising, consisting essentially of, or consisting of a nucleotide sequence encoding a polypeptide comprising the amino acid sequence of SEQ ID NO:2 or a biologically active fragment of said amino acid sequence or a constitutively activated mutant of said amino acid sequence or biologically active fragment thereof, wherein said biologically active fragment or constitutively active mutant comprises the methionine at position 604 of SEQ ID NO:2, comprises the threonine at amino acid position 856 of SEQ ID NO:2, or comprises the methionine at position 604 and the threonine at position 856 of SEQ ID NO:2. In some embodiments, said isolated polynucleotide comprises, consists essentially of, or consists of the polynucleotide of SEQ ID NO:1. The invention also relates to the complement of said isolated polynucleotide. In some embodiments, said isolated polynucleotide or complement thereof is purified.

An isolated polynucleotide comprising, consisting essentially of, or consisting of a nucleotide sequence encoding an allelic variant of the amino acid sequence of SEQ ID NO:2, wherein said allelic variant comprises the methionine at amino acid position 604 of SEQ ID NO:2, comprises a substitution of isoleucine for valine at amino acid position 801 of SEQ ID NO:2, or comprises the threonine at amino acid position 856 of SEQ ID NO:2 is envisioned to be within the scope of the invention.

An isolated polynucleotide comprising, consisting essentially of, or consisting of a nucleotide sequence encoding a variant of the amino acid sequence of SEQ ID NO:2, wherein said variant amino acid sequence is at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to the amino acid sequence of SEQ ID NO:2, and wherein said variant amino acid sequence comprises the methionine at amino acid position 604 of SEQ ID NO:2, comprises the threonine at amino acid position 856 of SEQ ID NO:2, or comprises the methionine at amino acid position 604 and the threonine at amino acid position 856 of SEQ ID NO:2, is envisioned to be within the scope of the invention.

In some embodiments, said biologically active fragment of RUP40 GPCR of SEQ ID NO:2 is selected from the group provided by the formula "n1-n2" to "c", which represents a set of fragments with an N-terminal amino acid selected from the amino acid interval "n1 to n2" of full-length RUP40 GPCR of SEQ ID NO:2 and a C-terminal amino acid fixed at amino acid "c" of full-length RUP40 GPCR of SEQ ID NO:2. In some embodiments, n1=2, n2=856, and c=1,346 for RUP40 GPCR of SEQ ID NO:2. In some embodiments, said biologically active fragment of RUP40 GPCR is selected from amino acids 2-1,346, 22-1,346, and 227-1,346 of SEQ ID NO:2, where amino acid 22 is understood to be the approximate site of predicted signal peptide cleavage, and amino acid 227 is understood to be the approximate site of predicted proteolytic cleavage within the SEA module. In some embodiments, n1=22, n2=856, and c=1,346 for RUP40 GPCR of SEQ ID NO:2. In some embodiments, n1=227, n2=856, and c=1,346 for RUP40 GPCR of SEQ ID NO:2.

The invention also relates to an isolated polynucleotide comprising a contiguous span of at least 18 nucleotides of SEQ ID NO:1, wherein said contiguous span comprises nucleotides 1,810-1,812 of SEQ ID NO:1, comprises nucleotides 2,566-2,568 of SEQ ID NO:1, or comprises nucleotides 1,810-1,812 and nucleotides 2,566-2,568 of SEQ ID NO:1. In some embodiments, said isolated polynucleotide is purified.

In a fourteenth aspect, the invention features a vector comprising the isolated polynucleotide of the thirteenth aspect. In some embodiments, the vector is isolated. In some embodiments, the vector is purified.

In some preferred embodiments, said vector is an expression vector. In some preferred embodiments, said expression vector is eukaryotic expression vector. In some preferred embodiments, said expression vector is pCMV. In some preferred embodiments, said expression vector is an adenoviral expression vector. Other suitable expression vectors will be readily apparent to those of ordinary skill in the art.

In a fifteenth aspect, the invention features a host cell transformed, transfected or infected with the expression vector of the fourteenth aspect.

In some embodiments, said host cell is prokaryotic. In some embodiments, said prokaryotic host cell is *E. coli*. In some preferred embodiments the host cell is eukaryotic, more preferably, mammalian, and more preferably selected from the group consisting of 293, 293T, CHO, and COS-7 cells. In other preferred embodiments, the host cell is eukaryotic, more preferably melanophore. Other suitable host cells will be readily apparent to those of ordinary skill in the art.

In some embodiments, the invention relates to a purified population of said transformed, transfected or infected host cell.

In a sixteenth aspect, the invention features a recombinant host cell that expresses recombinant polypeptide comprising the amino acid sequence of RUP40 GPCR of SEQ ID NO:2 or a biologically active fragment of the amino acid sequence of SEQ ID NO:2 or a constitutively activated mutant of the amino acid sequence of SEQ ID NO:2 or biologically active fragment thereof.

An allelic variant of the amino acid sequence of SEQ ED NO:2, wherein said allelic variant comprises the methionine at amino acid position 604 of SEQ ID NO:2, comprises a substitution of isoleucine for valine at amino acid position 801 of SEQ ID NO:2, or comprises the threonine at amino acid position 856 of SEQ ID NO:2 is envisioned to be within the scope of the invention.

A variant of the amino acid sequence of SEQ ID NO:2, wherein said variant amino acid sequence is at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to the amino acid sequence of SEQ ID NO:2, and wherein said variant amino acid sequence comprises the methionine at amino acid position 604 of SEQ ID NO:2, comprises a substitution of isoleucine for valine at amino acid position 801 of SEQ ID NO:2, or comprises the threonine at amino acid position 856 of SEQ ID NO:2 is envisioned to be within the scope of the invention.

In some embodiments, said biologically active fragment of RUP40 GPCR of SEQ ID NO:2 is selected from the group provided by the formula "n1-n2" to "c", which represents a set of fragments with an N-terminal amino acid selected from the amino acid interval "n1 to n2" of full-length RUP40 GPCR of SEQ ID NO:2 and a C-terminal amino acid fixed at amino acid "c" of full-length RUP40 GPCR of SEQ ID NO:2. In some embodiments, n1=2, n2=856, and c=1,346 for RUP40 GPCR of SEQ ID NO:2. In some embodiments, said biologically active fragment of RUP40 GPCR is selected from amino acids 2-1,346, 22-1,346, and 227-1,346 of SEQ ID NO:2, where amino acid 22 is understood to be the approximate site of predicted signal peptide cleavage, and amino acid 227 is understood to be the approximate site of predicted proteolytic cleavage within the SEA module. In some embodiments, n1=22, n2=856, and c=1,346 for RUP40 GPCR of SEQ ID NO:2. In some embodiments, n1=227, n2=856, and c=1,346 for RUP40 GPCR of SEQ ID NO:2.

In some embodiments, the invention relates to a purified population of said recombinant host cell expressing said recombinant polypeptide.

In a seventeenth aspect, the invention features a membrane of the recombinant host cell of the sixteenth aspect In an eighteenth aspect, the invention features an isolated polypeptide comprising the amino acid sequence of RUP40 GPCR of SEQ ID NO:2 or a biologically active fragment of the amino acid sequence of SEQ ID NO:2 or a constitutively activated mutant of the amino acid sequence of SEQ ID NO:2 or biologically active fragment thereof. In some embodiments, said isolated polypeptide is purified.

An allelic variant of the amino acid sequence of SEQ ID NO:2, wherein said allelic variant comprises the methionine at amino acid position 604 of SEQ ID NO:2, comprises a substitution of isoleucine for valine at amino acid position 801 of SEQ ID NO:2, or comprises the threonine at amino acid position 856 of SEQ ID NO:2 is envisioned to be within the scope of the invention.

A variant of the amino acid sequence of SEQ ID NO:2, wherein said variant amino acid sequence is at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to the amino acid sequence of SEQ ID NO:2, and wherein said variant amino acid sequence comprises the methionine at amino acid position 604 of SEQ ID NO:2, comprises a substitution of isoleucine for valine at amino acid position 801 of SEQ ID NO:2, or comprises the threonine at amino acid position 856 of SEQ ID NO:2 is envisioned to be within the scope of the invention.

In some embodiments, said biologically active fragment of RUP40 GPCR of SEQ ID NO:2 is selected from the group provided by the formula "n1-n2" to "c", which represents a set of fragments with an N-terminal amino acid selected from the amino acid interval "n1 to n2" of full-length RUP40 GPCR of SEQ ID NO:2 and a C-terminal amino acid fixed at amino acid "c" of full-length RUP40 GPCR of SEQ ID NO:2. In some embodiments, n1=2, n2=856, and c=1,346 for RUP40 GPCR of SEQ ID NO:2. In some embodiments, said biologically active fragment of RUP40 GPCR is selected from amino acids 2-1,346, 22-1,346, and 227-1,346 of SEQ ID NO:2, where amino acid 22 is understood to be the approximate site of predicted signal peptide cleavage, and amino acid 227 is understood to be the approximate site of predicted proteolytic cleavage within the SEA module. In some embodiments, n1=22, n2=856, and c=1,346 for RUP40 GPCR of SEQ ID NO:2. In some embodiments, n1=227, n2=856, and c=1,346 for RUP40 GPCR of SEQ ID NO:2.

The invention also relates to an isolated polypeptide comprising a contiguous span of at least 6 amino acids of SEQ ID NO:2, wherein said contiguous span comprises the methionine at amino acid position 604 of SEQ ID NO:2, comprises the threonine at amino acid position 856 of SEQ ID NO:2, or comprises the methionine at amino acid position 604 and the threonine at amino acid position 856 of SEQ ID NO:2.

In an nineteenth aspect, the invention features a method for producing a recombinant host cell comprising transforming, transfecting or infecting a cell with the expression vector of the fourteenth aspect such that the host cell, under appropriate conditions, produces a polypeptide comprising the amino acid sequence of SEQ ID NO:2 or a biologically active fragment of said amino acid sequence or a constitutively activated mutant of said amino acid sequence or biologically active fragment thereof, wherein said biologically active fragment or constitutively active mutant comprises the methionine at position 604 of SEQ ID NO:2, comprises the threonine at amino acid position 856 of SEQ ID NO:2, or comprises the methionine at position 604 and the threonine at position 856 of SEQ ID NO:2.

An allelic variant of the amino acid sequence of SEQ ID NO:2, wherein said allelic variant comprises the methionine at amino acid position 604 of SEQ ID NO:2, comprises a substitution of isoleucine for valine at amino acid position 801 of SEQ ID NO:2, or comprises the threonine at amino acid position 856 of SEQ PD NO:2 is envisioned to be within the scope of the invention.

A variant of the amino acid sequence of SEQ ID NO:2, wherein said variant amino acid sequence is at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to the amino acid sequence of SEQ ID NO:2, and wherein said variant amino acid sequence comprises the methionine at amino acid position 604 of SEQ II) NO:2, comprises a substitution of isoleucine for valine at amino acid position 801 of SEQ ID NO:2, or comprises the threonine at amino acid position 856 of SEQ ID NO:2 is envisioned to be within the scope of the invention.

In some embodiments, said biologically active fragment of RUP40 GPCR of SEQ ID NO:2 is selected from the group provided by the formula "n1-n2" to "c", which represents a set of fragments with an N-terminal amino acid selected from the amino acid interval "n1 to n2" of full-length RUP40 GPCR of SEQ ID NO:2 and a C-terminal amino acid fixed at amino acid "c" of full-length RUP40 GPCR of SEQ ID NO:2. In some embodiments, n1=2, n2=856, and c=1,346 for RUP40 GPCR of SEQ ID NO:2. In some embodiments, said biologically active fragment of RUP40 GPCR is selected from amino acids 2-1,346, 22-1,346, and 227-1,346 of SEQ ID NO:2, where amino acid 22 is understood to be the approximate site of predicted signal peptide cleavage, and amino acid 227 is understood to be the approximate site of predicted proteolytic cleavage within the SEA module. In some embodiments, n1=22, n2=856, and c=1,346 for RUP40 GPCR of SEQ ID NO:2. In some embodiments, n1=227, n2=856, and c=1,346 for RUP40 GPCR of SEQ ID NO:2.

In a twentieth aspect, the invention features an antibody that specifically binds to a polypeptide comprising, consisting essentially of, or consisting of the amino acid sequence of SEQ ID NO:2 and not to a variant of said polypeptide consisting of an amino acid substitution other than methionine at amino acid position 604 of SEQ ID NO:2, consisting of an amino acid substitution other than threonine at amino acid position 856 of SEQ ID NO:2, or consisting of an amino acid substitution other than methionine at amino acid position 604 and an amino acid substitution other than threonine at amino acid position 856 of SEQ ID NO:2, or an antigen-binding fragment of said antibody. In some embodiments, the antibody is monoclonal. In some embodiments, said monoclonal antibody is purified. Methods for making antibodies are within the purview of the skilled artisan (see, e.g., PCT Application Number PCT/IB02/01461 published as WO 02/066505 on 29 Aug. 2002; the disclosure of which is hereby incorporated by reference in its entirety).

In a twenty-first aspect, the invention features a method of binding a polypeptide comprising, consisting essentially of, or consisting of the amino acid sequence of SEQ ID NO:2 to the antibody of the twentieth aspect, comprising contacting said antibody with said polypeptide under conditions in which said antibody can specifically bind to said polypeptide.

In a twenty-second aspect, the invention features a process for making a modulator of a RUP40 GPCR, comprising the steps of:
 (a) identifying said modulator according to the method of claim 1; and
 (b) synthesizing the modulator identified in (a).

In some embodiments, said modulator is selected from the group consisting of agonist, partial agonist, inverse agonist and antagonist. In some embodiments, said modulator is an inverse agonist or an antagonist.

In some embodiments, said modulator is an inverse agonist or an antagonist of RUP40 GPCR having the amino acid sequence of SEQ ID NO:2 with an IC50 of less than 100 µM, of less than 10 µM, or of less than 1 µM. In some embodiments, said modulator is an inverse agonist or an antagonist with an IC50 of less than a value selected from the interval of 1 µM to 100 µM. In some embodiments, said modulator is an inverse agonist or an antagonist with an IC50 of less than a value selected from the interval of 1 µM to 10 W. In some embodiments, said modulator is an inverse agonist or an antagonist with an IC50 of less than 100 µM, of less than 10 µM, or of less than 1 µM in GTPγS binding assay carried out with membrane from transiently or stably transfected CHO cells, in pigment dispersion assay carried out in transiently transfected melanophores, or by IP3 assay in adenovirus infected cardiomyocytes expressing recombinant RUP40 GPCR polypeptide having the amino acid sequence of SEQ ID NO:2. In some embodiments, said modulator is an inverse agonist or antagonist with an IC50 of less than 100 µM in said assay. In some embodiments, said modulator is an inverse agonist or antagonist with an IC50 of less than 90 µM in said assay. In some embodiments, said modulator is an inverse agonist or antagonist with an IC50 of less than 80 µM in said assay. In some embodiments, said modulator is an inverse agonist or an antagonist with an IC50 of less than 70 µM in said assay. In some embodiments, said modulator is an inverse agonist or an antagonist with an IC50 of less than 60 µM in said assay. In some embodiments, said modulator is an inverse agonist or an antagonist with an IC50 of less than 50 µM in said assay. In some embodiments, said modulator is an inverse agonist or an antagonist with an IC50 of less than 40 µM in said assay. In some embodiments, said modulator is an inverse agonist or an antagonist with an IC50 of less than 30 µM in said assay. In some embodiments, said modulator is an inverse agonist or an antagonist with an IC50 of less than 20 µM in said assay. In some embodiments, said modulator is an inverse agonist or an antagonist with an IC50 of less than 10 µM in said assay. In some embodiments, said modulator is an inverse agonist or an antagonist with an IC50 of less than 9 µM in said assay. In some embodiments, said modulator is an inverse agonist or an antagonist with an IC50 of less than 8 µM in said assay. In some embodiments, said modulator is an inverse agonist or an antagonist with an IC50 of less than 7 µM in said assay. In some embodiments, said modulator is an inverse agonist or an antagonist with an IC50 of less than 6 µM in said assay. In some embodiments, said modulator is an inverse agonist or an antagonist with an IC50 of less than 5 µM in said assay. In some embodiments, said modulator is an inverse agonist or an antagonist with an IC50 of less than 4 µM in said assay. In some embodiments, said modulator is an inverse agonist or an antagonist with an IC50 of less than 3 µM in said assay. In some embodiments, said modulator is an inverse agonist or an antagonist with an IC50 of less than 2 µM in said assay. In some embodiments, said modulator is an inverse agonist or an antagonist with an IC50 of less than 1 µM in said assay. In some embodiments, said modulator is an inverse agonist or an antagonist with an IC50 in said assay of less than a value selected from the interval of 1 µM to 100 µM. In some embodiments, said modulator is an inverse agonist or an antagonist with an IC50 in said assay of less than a value selected from the interval of 1 µM to 10 µM. In some embodiments, said inverse agonist or antagonist is an inverse agonist. In some embodiments, said inverse agonist or antagonist is an antagonist.

In some embodiments, said modulator is selective for the GPCR.

In some embodiments, said modulator is a modulator of a heart disease. In some embodiments, said heart disease is congestive heart failure. In some embodiments, said heart disease is hypertrophic cardiomyopathy. In some embodiments, said modulator is a modulator of cardiomyocyte hypertrophy.

In some embodiments, said modulator is orally bioavailable. In some embodiments, said oral bioavailability can be shown to be at least 1%, at least 5%, at least 10%, at least 15%, at least 20%, at least 25%, at least 30%, at least 35%, at least 40%, or at least 45% relative to intraperitoneal administration. In some embodiments, said oral bioavailablity can be shown to be at least 1%, at least 5%, at least 10%, or at least 15% relative to intraperitoneal administration. In some embodiments, said oral bioavailability can be shown to be at least 1%, at least 5%, at least 10%, at least 15%, at least 20%, at least 25%, at least 30%, at least 35%, at least 40%, or at least 45% relative to intravenous administration. In some embodiments, said oral bioavailablity can be shown to be at least 1%, at least 5%, at least 10%, or at least 15% relative to intravenous administration.

In a twenty-third aspect, the invention features a use of a RUP40 GPCR to screen candidate compounds as pharmaceutical agents for a cardiovascular disorder, wherein the RUP40 GPCR is a receptor comprising an amino acid sequence selected from the group consisting of:
 (a) amino acids 1-1,346 of SEQ ID NO:2;
 (b) amino acids 1-990 of SEQ ID NO:2;
 (c) amino acids 991-1,346 of SEQ ID NO:2;
 (d) amino acids 954-997 of SEQ ID NO:2;
 (e) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
 (f) amino acids 1-1,349 of SEQ ID NO:4;
 (g) amino acids 1-993 of SEQ ID NO:4;
 (h) amino acids 994-1,349 of SEQ ID NO:4;
 (i) amino acids 954-1000 of SEQ ID NO:4; and
 (j) amino acids 1-141 of SEQ ID NO:6;
or a biologically active fragment of the amino acid sequence of SEQ ID NO:2 or 4; or a constitutively activated mutant of the amino acid sequence of SEQ ID NO:2 or 4 or said biologically active fragment thereof.

In some embodiments, said biologically active fragment of RUP40 GPCR of SEQ ID NO:2 or 4 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, n1=2, n2=994, and c=1,349 for RUP40 GPCR of SEQ ID NO:4. In some embodiments, said biologically active fragment of RUP40 GPCR is selected from amino acids 2-1,346, 22-1,346, 227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, said biologically active fragment of RUP40 GPCR is selected from amino acids 2-1,349, 25-1,349, 224-1,349, and 994-1,349 of SEQ ID NO:4, where amino acid 25 is understood to be the approximate site of predicted signal peptide cleavage, amino acid 224 is understood to be the approximate site of predicted proteolytic cleavage within the SEA module, and amino acid 994 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2. In some embodiments, n1=25, n2=994, and c=1,349 for RUP40 GPCR of SEQ ID NO:4. In some embodiments, n1=224, n2=994, and c=1,349 for RUP40 GPCR of SEQ ID NO:4.

Methods of mating a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2, 4 or 6 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 801 of SEQ ID NO:2, or comprising a substitution of methionine for threonine at amino acid position 856 of SEQ ID NO:2 is envisioned to be within the scope of the invention. In some embodiments, an allelic variant of RUP40 GPCR of SEQ ID NO:2 is the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8.

Mammalian orthologs of human RUP40 GPCR of SEQ ID NO:2 are envisioned to be within the scope of the invention. In some embodiments, said mammalian ortholog encompasses mouse RUP40, rat RUP40, pig RUP40, and non-human primate RUP40.

Variants of said RUP40 GPCR comprising an amino acid sequence at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to any of (a) to (j) are envisioned to be within the scope of the invention. Percent identity can be determined conventionally using known computer programs. Such algorithms and programs include, but are by no means limited to, TBLASTN, BLASTP, FASTA, TFASTA, and CLUSTALW [Pearson and Lipman (1988) Proc Natl Acad Sci USA 85:2444-8; Altschul et al. (1990) J Mol Biol 215:403-10; Thompson et al. (1994) Nucleic Acids Res 22:4673-80; Higgins et al. (1996) Meth Enzymol 266:383-402; Altschul et al. (1997) Nucleic Acids Res 25:3389-3402; Altschul et al. (1993) Nature Genetics 3:266-272; the disclosures of which are hereby incorporated by reference in their entireties].

In some embodiments, protein sequence homologies are evaluated using the Basic Local Alignment Search Tool ("BLAST"), which is well known in the art [See, e.g., Karlin and Altschul (1990) Proc Natl Acad Sci USA 87:2264-8; Altschul et al., 1990, 1993, 1997, all supra].

In some embodiments, the method for determining percent identity between two amino acid sequences is a method for determining the best overall match between a query sequence (e.g., the amino acid sequence of SEQ ID NO:2) and a sequence to be interrogated, also referred to as a global sequence alignment, using the FASTDB computer program based on the algorithm of Brutlag et al. [Comp App Biosci (1990) 6:237-245; the disclosure of which is hereby incorporated by reference in its entirety]. In a sequence alignment the query and interrogated sequences are both amino acid sequences. The results of said global sequence alignment is in percent identity. Preferred parameters used in a FASTDB amino acid alignment are: Matrix=PAM 0, k-tuple=2, Mismatch Penalty=1, Joining Penalty=-20, Randomization Group=25, Length=0, Cutoff Score=1, Window Size=sequence length, Gap Penalty=5, Gap Size Penalty=0.05, Window Size=247 or the length of the interrogated amino acid sequence, whichever is shorter.

If the interrogated sequence is shorter than the query sequence due to N- or C-terminal deletions, not because of internal deletions, the results, in percent identity, must be manually corrected because the FASTDB program does not account for N- and C-terminal truncations of the interrogated sequence when calculating global percent identity. For interrogated sequences truncated at the N- and C-termini, relative to the query sequence, the percent identity is corrected by calculating the number of residues of the query sequence that are N- and C-terminal of the interrogated sequence, that are not matched/aligned with a corresponding interrogated sequence residue, as a percent of the total bses of the query sequence. Whether a residue is matched/aligned is determined by results of the FASTDB sequence alignment. This percentage is then subtracted from the perecent identity, calculated by the above FASTDB program using the specified parameters, to arrive at a final percent identity score. This final percent identity score is what is used for the purposes of the present invention. Only residues to the N- and C-termini of the interrogated sequence, which are not matched/aligned with the query sequence, are considered for the purposes of manually adjusting the percent identity score. That is, only query amino acid residues outside the farthest N- and C-terminal residues of the interrogated sequence.

For example, a 90 amino acid residue interrogated sequence is aligned with a 100-residue query sequence to determine percent identity. The deletion occurs at the N-terminus of the interrogated sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched, the final percent identity would be 90%.

In another example, a 90-residue interrogated sequence is compared with a 100-residue query sequence. This time the deletions are internal so there are no residues at the N- or C-termini of the interrogated sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other corrections are made for the purposes of the present invention.

In some embodiments, said RUP40 GPCR is recombinant.

In some embodiments, said RUP40 GPCR comprises heterologous amino acid sequence. In some embodiments, said heterologous amino acid sequence is an epitope tag. In some embodiments, said epitope tag is hemagglutinin (HA) epitope tag. In some embodiments, said epitope tag is c-myc epitope tag. In some embodiments, said epitope tag is V5 epitope tag. Procedures for providing said HA, c-myc or V5 tag are well known to those of ordinary skill in the art (Clontech, Palo Alto, Calif. and Invitrogen, Carlsbad, Calif., for example).

In some embodiments, said receptor further comprises proteolytic cleavage of a signal peptide.

In some embodiments, said receptor further comprises proteolytic cleavage within an SEA module.

In some embodiments, said receptor further comprises proteolytic cleavage within a GPS domain.

In some embodiments, the cardiovascular disorder is heart disease. Heart disease includes but is not limited to congestive heart failure, congestive cardiomyopathy, heart hypertrophy, left ventricular hypertrophy, right ventricular hypertrophy, post-infarction heart rupture, ventricular septal rupture, endocarditis (including bacterial), heart aneurysm, pulmonary heart disease, rheumatic heart disease, and ventricular dysfunction. Heart disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Heart disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy.

In some embodiments, the cardiovascular disorder is hypertrophic cardiomyopathy. In some embodiments, the hypertrophic cardiomyopathy results from a hemodynamic disorder. In some embodiments, the hypertrophic cardiomyopathy results from a genetic disorder. In some embodiments, the hypertrophic cardiomyopathy results from post-myocardial infarction remodeling, cardiac valve disease, sustained cardiac afterload, myocarditis, or familial hypertrophic cardiomyopathy.

In some embodiments, said cardiovascular disorder is congenital heart defect. Congenital heart defect includes but is not limited to aortic coarctation, aortopulmonary septal defect, trilogy of Fallot, ventricular heart septal defect, and familial hypertrophic cardiomyopathy.

In some embodiments, the cardiovascular disorder is a cardiovascular disorder presenting with enlarged heart.

In some embodiments, the cardiovascular disorder is heart disease. In some embodiments, the heart disease is hypertrophic cardiomyopathy or congestive heart failure. In some embodiments, the hypertrophic cardiomyopathy results from post-myocardial infarction remodeling, cardiac valve disease, sustained cardiac afterload, myocarditis, or familial hypertrophic cardiomyopathy.

In some embodiments, the pharmaceutical agent is not an antibody or an antigen-binding fragment thereof.

In some embodiments, the pharmaceutical agent is a small molecule, with the proviso that the small molecule is not an antibody or an antigen-binding fragment thereof.

In some embodiments, the pharmaceutical agent is a polypeptide, with the proviso that the polypeptide is not an antibody or an antigen-binding fragment thereof.

In some embodiments, the pharmaceutical agent is a lipid.

In some embodiments, the pharmaceutical agent is an antibody or an antigen-binding fragment thereof.

In some embodiments, the pharmaceutical agent is a ligand of the receptor.

In some embodiments, the pharmaceutical agent is a modulator of the receptor. In some embodiments, the pharmaceutical agent is an agonist, partial agonist, inverse agonist, or antagonist of the receptor. In some embodiments, the pharmaceutical agent is an inverse agonist or an antagonist of the receptor. In some embodiments, the pharmaceutical agent is an inverse agonist of the receptor. In some embodiments, the pharmaceutical agent is an antagonist of the receptor.

In some embodiments, said use further comprises synthesis of said screened pharmaceutical agent.

In some embodiments, said use further comprises:
(a) optionally, determining the structure of the compound; and
(b) providing the compound or pharmaceutical agent or the name or structure of the compound.

In some embodiments, said use further comprises:
(a) optionally, determining the structure of the compound;
(b) optionally, providing the name or structure of the compound; and
(c) producing or synthesizing the compound.

Applicant reserves the right to exclude any one or more candidate compound from any of the embodiments of the invention. Applicant also reserves the right to exclude any one or more modulator from any of the embodiments of the invention. Applicant further reserves the right to exclude any one or more polynucleotide or polypeptide, or any one or more fragment of said polynucleotide or said polypeptide, from any of the embodiments of the invention. Applicant additionally reserves the right to exclude any one or more cardiovascular disorder from any of the embodiments of the invention.

Throughout this application, various publications, patents and published patent applications are cited. The disclosures of these publications, patents and published patent applications referenced in this application are hereby incorporated by reference in their entirety into the present disclosure. Citation herein by Applicant of a publication, patent, or published patent application is not an admission by Applicant of said publication, patent, or published patent application as prior art.

Modifications and extension of the disclosed inventions that are within the purview of the skilled artisan are encompassed within the above disclosure and the claims that follow.

BRIEF DESCRIPTION OF THE DRAWINGS

FIG. 1 depicts results from a primary screen of candidate compounds against a "target receptor" which is a Gsα Fusion Protein construct of an endogenous, constitutively active Gs-coupled GPCR. Results for "Compound A" are provided in well A2. Results for "Compound "B" are provided in well G9.

Figure 1:
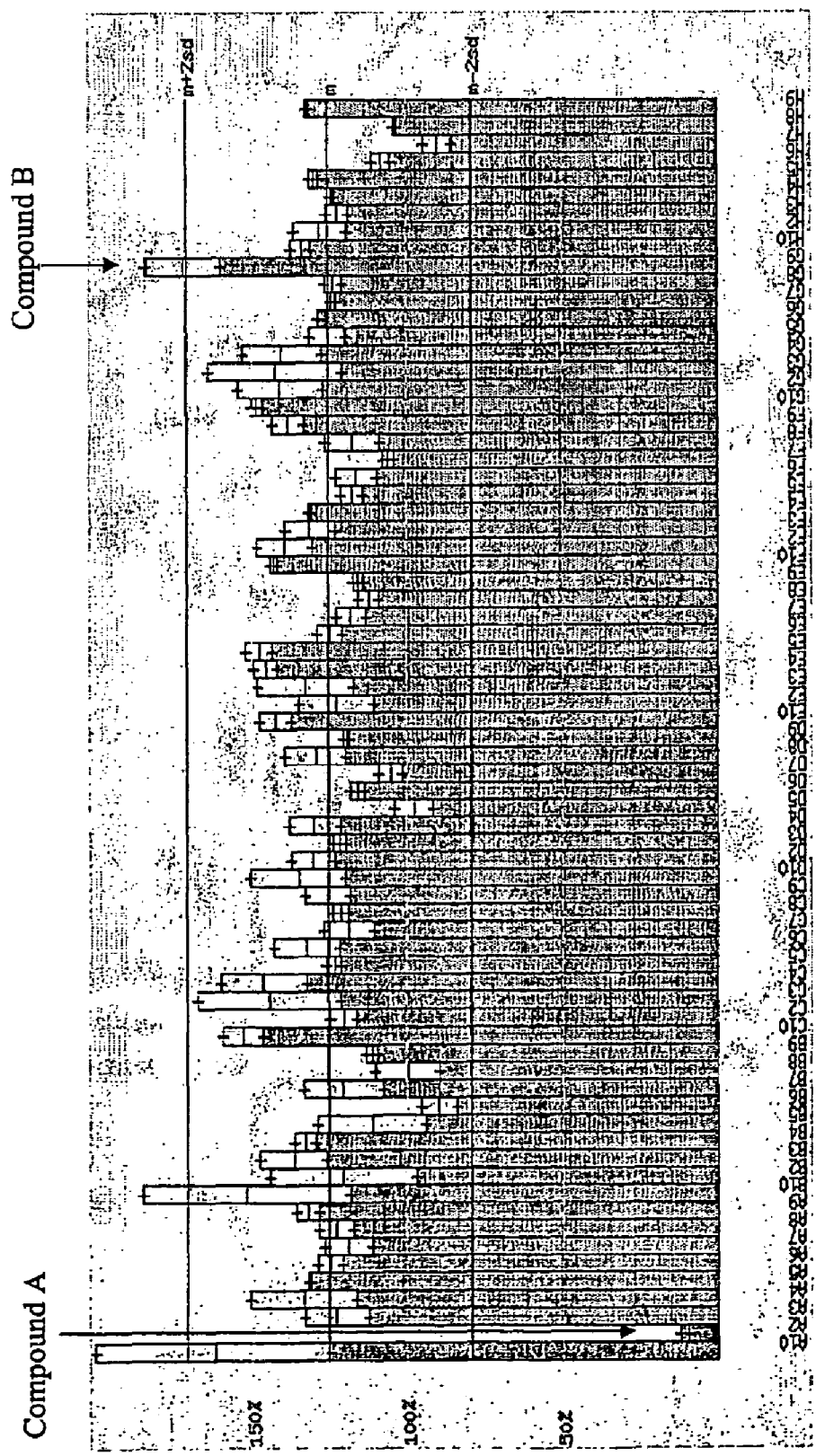
FIG. 1. By way of example and not limitation.

Inspection of the plot indicates that expression of human RUP40 is highly expressed in heart, lung, aorta and adipose. Human RUP40 is expressed at lower level in spleen. Within heart, RUP40 is highly expressed by left ventricle. In the mouse, RUP40 is selectively expressed in heart, lung and adipose (not shown).

FIG. 3. RUP40 expression in heart was determined by immunohistochemistry. Adult rat heart sections were stained with rabbit anti-RUP40 antibody or with immunoglobulin from non-immunized rabbits (Negative Control). Cardiac myocytes showed diffuse staining throughout the cytosol with more intense staining at the plasma cell membrane.

FIG. 4. RUP40 is expressed in cardiomyocytes (RT-PCR analysis). RT-PCR demonstrates expression of RUP40 transcript in neonatal rat ventricular myocytes (NRVMs) maintained under serum-free (SFM) conditions for 24 hours. RUP40 transcript levels in the myocytes drop dramatically 24 hours following addition of phorbol 12-myristate 13-acetate (PMA) but remain elevated following addition of phenylephrine (PE) or prostaglandin F2alpha (PG) to media. Note nearly undetectable levels of RUP40 expression in primary cardiac fibroblasts (Fibro). G3PDH PCR product demonstrates equal levels of template used for the PCR reaction and consistency of gel loading. Amplification was template-dependent, as indicated by the "-" lane of the gel corresponding to amplification in the absence of template.

FIG. 5. Overexpression of RUP40 in cardiomyocytes stimulates increased IP3 accumulation. Neonatal rat ventricular myocytes (NRVMs) were infected with recombinant adenovirus encoding human RUP40 polypeptide of SEQ ID NO:2 (AdRUP40), infected with recombinant adenovirus encoding Green Fluorescent Protein (AdGFP), or were mock infected (Control).

FIG. 6A. Overexpression of RUP40 stimulates hypertrophy of cardiomyocytes. Neonatal rat ventricular myocytes (NRVMs) were infected with recombinant adenovirus encoding human RUP40 polypeptide of SEQ ID NO:2 (AdRUP40) or with recombinant adenovirus encoding Green Fluorescent Protein (AdGFP). NRVMs infected with AdRUP40 for 48 hours demonstrate increased cell size compared to control cells infected with AdGFP control virus or control mock-infected cells (Control).

FIG. 6B. Overexpression of RUP40 stimulates increased atrial natruiretic factor (ANF) expression in cardiomyocytes. Neonatal rat ventricular myocytes (NRVMs) were infected with recombinant adenovirus encoding human RUP40 polypeptide of SEQ ID NO:2 (AdRUP40) or recombinant adenovirus encoding Green Fluorescent Protein (AdGFP). 24 hours after adenovirus infection, total RNA was isolated and Northern blot analysis was carried out to determine levels of virally expressed RUP40. The same membrane was probed for atrial natruiretic factor (ANF) expression.

FIG. 7. Under conditions of pressure overload induced cardiac hypertrophy resulting from transverse aortic constriction (TAC), levels of RUP40 mRNA are maintained or increased slightly. Mice undergoing surgery were subjected (TAC) or not subjected (SHAM) to transverse aortic constriction. Myocardial expression of RUP40 mRNA in TAC and SHAM mice was determined 7 days after surgery by in situ hybridization using antisense riboprobe. Sense riboprobe was used as a negative control.

DETAILED DESCRIPTION

Definitions

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

AGONISTS shall mean materials (e.g., ligands, candidate compounds) that activate an intracellular response when they bind to the receptor. In some embodiments, agonists are those materials not previously known to activate the intracellular response when they bind to the receptor (e.g. to enhance GTPγS binding to membranes or to elevate intracellular IP3 level).

AMINO ACID ABBREVIATIONS used herein are set out in Table A:

TABLE A

| | | |
|---|---|---|
| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |

TABLE A-continued

| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

ANTAGONISTS shall mean materials (e.g., ligands, candidate compounds) that competitively bind to the receptor at the same site as the agonists but which do not activate an intracellular response, and can thereby inhibit the intracellular responses elicited by agonists. Antagonists do not diminish the baseline intracellular response in the absence of an agonist. In some embodiments, antagonists are those materials not previously known to compete with an agonist to inhibit the cellular response when they bind to the receptor, e.g. wherein the cellular response is GTPγS binding to membranes or the elevation of intracellular IP3 level.

ANTIBODIES are intended herein to encompass monoclonal antibodies and polyclonal antibodies. ANTIBODIES are further intended to encompass IgG, IgA, IgD, IgE, and IgM. ANTIBODIES include whole antibodies, including single-chain whole antibodies, and antigen binding fragments thereof, including Fab, Fab', F(ab)$_2$ and F(ab')2. ANTIBODIES may be from any animal origin. Preferably, ANTIBODIES are human, murine, rabbit, goat, guinea pig, hamster, camel, donkey, sheep, horse or chicken. Preferably ANTIBODIES have binding affinities with a dissociation constant or Kd value less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{9}$M, $5 \times 10^{-10}$M $10^{-10}$M, $5 \times 10^{-11}$M, $10^{-11}$M, $5 \times 10^{-13}$M, $10^{-13}$M, $5 \times 10^{-13}$M, $10^{-13}$M, $5 \times 10^{-14}$M $10^{-14}$M, $5 \times 10^{-15}$M and $10^{-15}$M. ANTIBODIES of the present invention may be prepared by any suitable method known in the art.

BIOLOGICALLY ACTIVE FRAGMENT shall mean a fragment of a full-length polypeptide or amino acid sequence retaining part or all of the functionality of the full-length polypeptide or amino acid sequence. In particular embodiment, an active fragment of a full-length GPCR polypeptide or amino acid sequence retains part or all of the functionality of the full-length GPCR polypeptide or amino acid sequence. Said GPCR functionality is understood to encompass but not be limited to ligand binding, G-protein coupling, and ligand-facilitated coupling to G-protein. In some embodiments, said GPCR functionality is G protein coupling. In some embodiments, said GPCR functionality is ligand-facilitated coupling to G-protein. By way of illustration and not limitation, biologically active fragment is intended herein to encompass full-length GPCR polypeptide absent an N-terminal methionine.

CANDIDATE COMPOUND shall mean a molecule (for example, and not limitation, a chemical compound) that is amenable to a screening technique. A CANDIDATE COMPOUND may be, for example, a polypeptide, a lipid, a small molecule, an antibody, a polynucleotide.

CARDIAC EJECTION FRACTION shall be taken to refer to the fraction of blood ejected from the left ventricle with a single contraction. For example, if 100 ml of blood is in the left ventricle and 90 ml is ejected upon contraction, then the cardiac ejection fraction is 90%.

CARDIAC HYPERTROPHY shall be taken to refer to enlargement of the heart muscle (myocardium). Cardiac hypertrophy is usually, but not always, an adaptive response to increased hemodynamic load imposed upon the myocardium.

CARDIAC VALVE DISEASE shall be taken to refer to abnormal structure or function of one or more of the valves in the heart resulting in pathogenic cardiac hemodynamics.

CODON shall mean a grouping of three nucleotides (or equivalents to nucleotides) which generally comprise a nucleoside [adenosine (A), guanosine (G), cytidine (C), uridine (U) and thymidine (I)] coupled to a phosphate group and which, when translated, encodes an amino acid.

COMPOSITION means a material comprising at least one component. A "pharmaceutical composition" is an example of a composition.

COMPOUND EFFICACY shall mean a measurement of the ability of a compound to inhibit or stimulate receptor functionality; i.e. the ability to activate/inhibit a signal transduction pathway, in contrast to receptor binding affinity. Exemplary means of detecting compound efficacy are disclosed in the Example section of this patent document.

COMPRISING, CONSISTING ESSENTIALLY OF, and CONSISTING OF are defined herein according to their standard meaning. A defined meaning set forth in the M.P.E.P. controls over a defined meaning in the art and a defined meaning set forth in controlling Federal Circuit case law controls over a meaning set forth in the M.P.E.P.

CONGENITAL HEART DEFECT shall refer to an abnormality in cardiocirculatory structure or function that is present at birth, even if is it discovered much later.

CONGESTIVE HEART FAILURE shall refer to a disorder in which the heart loses its ability to pump blood efficiently. Congestive heart failure becomes more prevalent with advancing age. Ischemic heart disease is the most common cause of congestive heart failure, accounting for 60-70% of all cases. An increased venous pressure greater than 12 mmHg is one of the major Framingham criteria for congestive heart failure, as is a reduction in cardiac output equivalent to a circulation time greater than 25 seconds.

CONSTITUTIVELY ACTIVE RECEPTOR shall mean a receptor stabilized in an active state by means other than through binding of the receptor to its ligand or a chemical equivalent thereof. A constitutively active receptor may be endogenous or non-endogenous.

CONSTITUTIVELY ACTIVATED RECEPTOR shall mean an endogenous receptor that has been modified so as to be constitutively active.

CONSTITUTIVE RECEPTOR ACTIVATION shall mean activation/of a receptor in the absence of binding to its ligand or a chemical equivalent thereof.

CONTACT or CONTACTING shall mean bringing at least two moieties together, whether in an in vitro system or an in vivo system.

DECREASE is used to refer to a reduction in a measurable quantity and is used synonymously with the terms "reduce", "diminish", "lower", and "lessen".

ECHOCARDIOGRAPHY shall be taken to refer to a method of using sound waves to measure cardiac structure and function in living animals. By way of illustration and not limitation, echocardiography may be used in the determination of an enlarged heart.

ENDOGENOUS shall mean a material that a mammal naturally produces. Endogenous in reference to, for example and not limitation, the term "receptor," shall mean that which is naturally produced by a mammal (for example, and not limitation, a human). Endogenous shall be understood to encompass allelic variants of a gene as well as the allelic polypeptide variants so encoded. By contrast, the term NON-ENDOGENOUS in this context shall mean that which is not naturally produced by a mammal (for example, and not limitation, a human). For example, and not limitation, a receptor which is not constitutively active in its endogenous form, but when manipulated becomes constitutively active, is most preferably referred to herein as a "non-endogenous, constitutively activated receptor."

ENLARGED HEART shall be taken to refer to an increase (beyond normal range based on body size) in the thickness of the ventricular chamber walls.

EXPRESSION VECTOR is defined herein as a DNA sequence that is required for the transcription of cloned DNA and the translation of the transcribed mRNAs in an appropriate host cell recombinant for said expression vector. An appropriately constructed expression vector should contain an origin of replication for autonomous replication in host cells, selectable markers, a limited number of useful restriction enzyme sites, a potential for high copy number, and active promoters. Said cloned DNA to be transcribed is operably linked to a constitutively or conditionally active promoter within said expression vector. By way of illustration and not limitation, pCMV is an expression vector.

G PROTEIN COUPLED RECEPTOR FUSION PROTEIN and GPCR FUSION PROTEIN, in the context of the invention disclosed herein, each mean a non-endogenous protein comprising an endogenous, constitutively active GPCR or a non-endogenous, constitutively activated GPCR fused to at least one G protein, most preferably the alpha (α) subunit of such G protein (this being the subunit that binds GTP), with the G protein preferably being of the same type as the G protein that naturally couples with endogenous GPCR. For example, and not limitation, in an endogenous state, if the G protein "Gsα" is the predominate G protein that couples with the GPCR, a GPCR Fusion Protein based upon the specific GPCR would be a non-endogenous protein comprising the GPCR fused to Gsα; in some circumstances, as will be set forth below, a non-predominant G protein can be fused to the GPCR. The G protein can be fused directly to the C-terminus of the constitutively active GPCR or there may be spacers between the two.

HEMODYNAMIC shall be taken to pertain to the movement of the blood and the forces concerned therein throughout the circulatory system. By way of illustration and not limitation, sustained hemodynamic perturbations resulting in elevated demand imposed upon the myocardium result in cardiac hypertrophy. Alternatively, GENETIC abnormalities within the cells of the myocardium can result in cardiac hypertrophy independent of hemodynamics. By way of illustration and not limitation, genetic disorders such as mutations in sarcomeric proteins result in familial hypertrophic cardiomyopathy [see, e.g., Bashyam et al., J Hum Genet (2003) 48:55-64].

HOST CELL shall mean a cell capable of having an expression vector incorporated therein. Said incorporation may occur through, by way of illustration and not limitation, transformation, transfection or infection. In some embodiments the host cell is eukaryotic, more preferably, mammalian, and more preferably selected from the group consisting of 293, 293T, CHO, and COS-7 cells. In some embodiments, the host cell is cardiomyocyte. In other embodiments, the host cell is eukaryotic, more preferably melanophore.

HYPERTROPHIC CARDIOMYOPATHY shall be taken to refer to the enlargement of the heart due to an increase in size of the cells making up the myocardium.

IN NEED OF PREVENTION OR TREATMENT as used herein refers to a judgement made by a caregiver (e.g. physician, nurse, nurse practitioner, etc. in the case of humans; veterinarian in the case of animals, including non-human mammals) that an individual or animal requires or will benefit from treatment. This judgement is made based on a variety of factors that are in the realm of a caregiver's expertise, but that include the knowledge that the individual or animal is ill, or will be ill, as the result of a condition that is treatable by the compounds of the invention.

INCREASED VENOUS PRESSURE shall be taken to refer to the elevated blood pressure that develops in the venous system (veins) due to pooling of blood there caused by a weakening of the circulatory system.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound.

INVERSE AGONISTS shall mean materials (e.g., ligand, candidate compound) that bind either to the endogenous form or to the constitutively activated form of the receptor so as to reduce the baseline intracellular response of the receptor observed in the absence of agonists.

ISCHEMIC HEART DISEASE shall refer to a disorder caused by lack of oxygen to the tissues of the heart, in which muscles of the heart are affected and the heart cannot pump properly. Ischemic heart disease is the most common cardiomyopathy in the United States.

ISOLATED shall mean that the material is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such a polynucleotide could be part of a vector and/or such a polynucleotide or polypeptide could be part of a composition, and still be isolated in that the Vector or composition is not part of its natural environment.

LIGAND shall mean a molecule that specifically binds to a GPCR. A ligand may be, for example, a polypeptide, a lipid, a small molecule, an antibody. An endogenous ligand is a ligand that is an endogenous, natural ligand for a native GPCR. A ligand may be a GPCR "antagonist", "agonist", "partial agonist", or "inverse agonist", or the like.

As used herein, the terms MODULATE or MODIFY are meant to refer to an increase or decrease in the amount, quality, or effect of a particular activity, function or molecule.

MYOCARDIAL INFARCTION shall refer to the damage or death of an area of heart muscle because of an inadequate supply of oxygen to that area. Myocardial infarctions are often caused by a clot that blocks one of the coronary arteries (the blood vessels that bring blood and oxygen to heart muscle). The clot prevents blood and oxygen from reaching that area of the heart, leading to the death of heart cells in that area MYOCARDITIS shall be taken to refer to an inflammation of the myocardium of bacterial, viral or unknown etiology.

ORPHAN RECEPTOR shall mean an endogenous receptor for which an endogenous ligand specific for that receptor has not been identified or is not known.

PARTIAL AGONISTS shall mean materials (e.g., ligands, candidate compounds) that activate the intracellular response when they bind to the receptor to a lesser degree/extent than do full agonists.

PHARMACEUTICAL AGENT shall mean a compound that may be used as an active ingredient in a pharmaceutical composition.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

POLYNUCLEOTIDES shall mean RNA, DNA, or RNA/DNA hybrid sequences of more than one nucleotide in either single chain or duplex form. The polynucleotides of the invention may be prepared by any known method, including synthetic, recombinant, ex vivo generation, or a combination thereof, as well as utilizing any purification methods known in the art.

POLYPEPTIDE shall refer to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide.

POST-MYOCARDIAL INFARCTION REMODELING. The loss of myocardial tissue due to myocardial infarction results in a sustained excessive hemodynamic burden placed on the ventricle. Ventricular hypertrophy constitutes one of the principle mechanisms by which the heart compensates for an increased load. However, the capacity for this adaptation to sustain cardiac performance in the face of hemodynamic overload is finite and, when chronically maintained, becomes maladaptive. Gradually, the adaptive hypertrophic phenotype transitions to overt heart failure as the enlarged ventricles progressively dilate and contractile function weakens. The natural history of the adaptive and maladaptive response to myocardial infarction in the heart is referred to as 'remodeling'.

PRIMER is used herein to denote a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

PURIFIED is used herein to describe a polynucleotide or polynucleotide vector of the invention that has been separated from other compounds including, but not limited to, other nucleic acids, carbohydrates, lipids and proteins (such as the enzymes used in the synthesis of the polynucleotide). A polynucleotide is substantially pure when at least about 50%, at least about 60%, at least about 75%, or at least about 90% of a sample contains a single polynucleotide sequence. A substantially pure polynucleotide typically comprises about 50%, about 60%, about 70%, about 80%, about 90%, about 95%, or about 99% weight/weight of a nucleic acid sample. Polynucleotide purity or homogeneity may be indicated by a number of means well known in the art, such as agarose or polyacrylamide gel electrophoresis of a sample, followed by visualizing a single polynucleotide band upon staining the gel.

Similarly, the term purified is used herein to describe a polypeptide of the invention that has been separated from other compounds including, but not limited to, nucleic acids, lipids, carbohydrates and other proteins. In some preferred embodiments, a polypeptide is substantially pure when at least about 50%, at least about 60%, at least about 75%, at least about 85%, at least about 90%, at least about 95%, at least about 96%, at least about 97%, at least about 98%, at least about 99%, or at least about 99.5% of the polypeptide molecules of a sample have a single amino acid sequence. In some preferred embodiments, a substantially pure polypeptide typically comprises about 50%, about 60%, about 70%, about 80%, about 90%, about 95%, about 96%, about 97%, about 98%, about 99% or about 99.5% weight/weight of a protein sample. Polypeptide purity or homogeneity is indicated by a number of methods well known in the art, such as agarose or polyacrylamide gel electrophoresis of a sample, followed by visualizing a single polypeptide band upon staining the gel.

Similarly, the term purified is used herein to describe a population of host cell transformed, transfected or infected with expression vector. In some preferred embodiments, said population comprises at least about 10%, at least about 20%, at least about 30%, at least about 40%, at least about 50%, at least about 60%, at least about 70%, at least about 80%, at least about 85%, at least about 90%, at least about 91%, at least about 92%, at least about 93%, at least about 94%, at least about 95%, at least about 96%, at least about 97%, at least about 98% or at least about 99% of said transformed, transfected or infected host cell.

Similarly, the term purified is used herein to describe a population of host cell expressing recombinant polypeptide. In some preferred embodiments, said population comprises at least about 10%, at least about 20%, at least about 30%, at least about 40%, at least about 50%, at least about 60%, at least about 70%, at least about 80%, at least about 85%, at least about 90%, at least about 91%, at least about 92%, at least about 93%, at least about 94%, at least about 95%, at least about 96%, at least about 97%, at least about 98% or at least about 99% of said host cell expressing said recombinant polypeptide.

Further, as used herein, the term purified does not require absolute purity; rather, it is intended as a relative definition.

RECEPTOR FUNCTIONALITY shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins.

REDUCED CARDIAC OUTPUT shall be taken to refer to the decreased pumping capacity of the failing heart such that less blood is pumped into the circulatory system (arteries) with each contraction of the heart's ventricles.

SECOND MESSENGER shall mean an intracellular response produced as a result of receptor activation. A second messenger can include, for example, inositol triphosphate (IP3), diacylglycerol (DAG), cyclic AMP (cAMP), cyclic GMP (cGMP), MAP kinase activity, MAPKJERK kinase kinase-1 (MEKK1) activity, and Ca2+. Second messenger response can be measured for a determination of receptor activation. In addition, second messenger response can be measured for the identification of candidate compounds, including for example, inverse agonists, partial agonists, agonists, and antagonists.

SIGNAL TO NOISE RATIO shall mean the signal generated in response to activation, amplification, or stimulation wherein the signal is above the background noise or the basal level in response to non-activation, non-amplification, or non-stimulation.

SMALL MOLECULE shall be taken to mean a compound having a molecular weight of less than about 10,000 grams per mole, including a peptide, peptidomimetic, amino acid, amino acid analogue, polynucleotide, polynucleotide analogue, nucleotide, nucleotide analogue, organic compound or inorganic compound (i.e., including a heteroorganic compound or organometallic compound), and salts, esters and other pharmaceutically acceptable forms thereof. In certain preferred embodiments, small molecules are organic or inorganic compounds having a molecular weight of less than about 5,000 grams per mole. In certain preferred embodiments, small molecules are organic or inorganic compounds having molecular weight of less than about 1,000 grams per mole. In certain preferred embodiments, small molecules are organic or inorganic compounds having a molecular weight of less than about 500 grams per mole.

SPACER shall mean a translated number of amino acids that are located after the last codon or last amino acid of a gene, for example a GPCR of interest, but before the start codon or beginning regions of the G protein of interest, wherein the translated number amino acids are placed in-frame with the beginnings regions of the G protein of interest. The number of translated amino acids can be one, two, three, four, etc., and up to twelve.

STIMULATE or STIMULATING, in relationship to the term "response" shall mean that a response is increased in the presence of a compound as opposed to in the absence of the compound.

SUBJECT shall mean primates, including but not limited to humans and baboons, as well as pet animals such as dogs and cats, laboratory animals such as rats and mice, and farm animals such as horses, sheep, and cows.

SUSTAINED CARDIAC AFTERLOAD. Afterload is a measurement of the resistance to flow of blood out from the heart into the circulatory system. High systemic blood pressure or abnormal narrowing of the aorta (coarctation) increase the afterload imposed on the heart.

THERAPEUTICALLY EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:
  (1) Preventing the disease; for example, preventing a disease, condition or disorder in an individual that may be predisposed to the disease, condition or disorder but does not yet experience or display the pathology or symptomatology of the disease,
  (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and
  (3) Ameliorating the disease; for example, ameliorating a disease, condition or diiorder in an individual that is experiencing or displaying the pathology or symptomatology of the disease, condition or disorder (i.e., reversing the pathology and/or symptomatology).

VARIANT as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. A typical variant of a polypeptide differs in amino acid sequence from another, reference polypeptide. A variant and reference polypeptide may differ in amino acid sequence by one or more substitutions, additions, deletions in any combination. A variant of a polynucleotide or polypeptide may be a naturally occurring one such as an ALLELIC VARIANT, or it may be a variant that is not known to occur naturally. Non-naturally occurring variants of polynucleotides and polypeptides may be made by mutagenesis techniques or by direct synthesis.

VENTRICULAR CHAMBER VOLUME shall be taken to refer to a measurement of the internal dimensions of the left or right ventricular chambers of the heart. In the failing heart, there is an enlargement of the ventricular chambers.

A. Introduction

The order of the following sections is set forth for presentational efficiency and is not intended, nor should be construed, as a limitation on the disclosure or the claims to follow.

B. Receptor Expression

1. GPCR Polypeptides of Interest

A RUP40 GPCR of the invention may comprise an amino acid sequence selected from the group consisting of:
  (a) amino acids 1-1,346 of SEQ ID NO:2;
  (b) amino acids 1-990 of SEQ ID NO:2;
  (c) amino acids 991-1,346 of SEQ ID NO:2;
  (d) amino acids 954-997 of SEQ ID NO:2;
  (e) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
  (f) amino acids 1-1,349 of SEQ ID NO:4;
  (g) amino acids 1-993 of SEQ ID NO:4;
  (h) amino acids 994-1,349 of SEQ ID NO:4;
  (i) amino acids 954-1000 of SEQ ID NO:4; and
  (j) amino acids 1-141 of SEQ ID NO:6.

A RUP40 GPCR of the invention may comprise a biologically active fragment of the amino acid sequence of SEQ ID NO:2 or 4. A RUP40 GPCR of the invention may comprise a constitutively activated mutant of the amino acid sequence of SEQ ID NO:2 or 4 or of said biologically active fragment of the amino acid sequence of SEQ ID NO:2 or 4.

In some embodiments, said biologically active fragment of RUP40 GPCR of SEQ ID NO:2 or 4 is selected from the group provided by the formula "n1-n2" to "c", which represents a set of fragments with an N-terminal amino acid selected from the amino acid interval "n1 to n2" of full-length RUP40 GPCR and a C-terminal amino acid fixed at amino acid "c" of full-length RUP40 GPCR. In some embodiments, "n1" is amino acid 2 of full-length RUP40 GPCR, "n2" is the amino acid C-terminal to the approximate site of predicted proteolytic cleavage within the GPS domain, and "c" is the C-terminal amino acid of full-length RUP40 GPCR. In some embodiments, n1=2, n2=991, and c=1,346 for RUP40 GPCR of SEQ ID NO:2. In some embodiments, n1=2, n2=994, and c=1,349 for RUP40 GPCR of SEQ ID NO:4. In some embodiments, said biologically active fragment of RUP40 GPCR is selected from amino acids 2-1,346, 22-1,346, 227-1,346, and 991-1,346 of SEQ ID NO:2, where amino acid 22 is understood to be the approximate site of predicted signal peptide cleavage, amino acid 227 is understood to be the approximate site of predicted proteolytic cleavage within the SEA module, and amino acid 991 is understood to be the approximate site of predicted proteolytic cleavage within the GPS domain. In some embodiments, said biologically active fragment of RUP40 GPCR is selected from amino acids 2-1,349,25-1,349,224-1,349, and 994-1,349 of SEQ ID NO:4, where amino acid 25 is understood to be the approximate site of predicted signal peptide cleavage, amino acid 224 is understood to be the approximate site of predicted proteolytic cleavage within the SEA module, and amino acid 994 is understood to be the approximate site of predicted proteolytic cleavage within the GPS domain. In some embodiments, n1=22, n2=991, and c=1,346 for RUP40 GPCR of SEQ ID NO:2. In some embodiments, n1=227, n2=991, and c=1,346 for RUP40 GPCR of SEQ ID NO:2. In some embodiments, n1=25, n2=994, and c=1,349 for RUP40 GPCR of SEQ ID NO:4. In some embodiments, n1=224, n2=994, and c=1,349 for RUP40 GPCR of SEQ ID NO:4.

Methods of making a constitutively activated mutant of a GPCR are within the purview of those of ordinary skill in the art (see, e.g., PCT Application Number PCT/US98/07496 published as WO 98/46995 on 22 Oct. 1998; and U.S. Pat. No. 6,555,339; the disclosures of which are hereby incorporated by reference in their entireties).

Allelic variants of RUP40 GPCR of SEQ ID NO:2, 4 or 6 are envisioned to be within the scope of the invention. By way of illustration and not limitation, an allelic variant of RUP40 GPCR of SEQ ID NO:2 comprising a substitution of threonine for methionine at amino acid position 604 of SEQ ID NO:2, comprising a substitution of isoleucine for valine at amino acid position 801 of SEQ ID NO:2, or comprising a substitution of methionine for threonine at amino acid position 856 of SEQ ID NO:2 is envisioned to be within the scope of the invention. In certain embodiments, a GPCR that may be used in the subject methods may comprise an allelic variant of the amino acid sequence of SEQ ID NO:2. In certain embodiments, an allelic variant of the amino acid sequence of SEQ ID NO:2 is encoded by an endogenous RUP40 GPCR nucleotide sequence obtainable by performing polymerase chain reaction (PCR) on a human DNA sample using specific primers SEQ ID NO:7 and SEQ ID NO:8. In some embodiments, an allelic variant of the amino acid sequence of SEQ ID NO:2 is encoded by an endogenous RUP40 GPCR nucleotide sequence obtainable by performing polymerase chain reaction (PCR) on a human DNA sample using a specific primer comprising SEQ ID NO:7 and a specific primer comprising SEQ ID NO:8.

Mammalian orthologs of human RUP40 GPCR of SEQ ID NO:2 are envisioned to be within the scope of the invention. In some embodiments, said mammalian ortholog encompasses mouse RUP40, rat RUP40, pig RUP40, and non-human primate RUP40.

Variants of said RUP40 GPCR comprising an amino acid sequence at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to an amino acid sequence selected from the group consisting of:
  (a) amino acids 1-1,346 of SEQ ID NO:2;
  (b) amino acids 1-990 of SEQ ID NO:2;
  (c) amino acids 991-1,346 of SEQ ID NO:2;
  (d) amino acids 954-997 of SEQ ID NO:2;
  (e) the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8;
  (f) amino acids 1-1,349 of SEQ ID NO:4;
  (g) amino acids 1-993 of SEQ ID NO:4;
  (h) amino acids 994-1,349 of SEQ ID NO:4;
  (i) amino acids 954-1000 of SEQ ID NO:4; and
  (j) amino acids 1-141 of SEQ ID NO:6.
are envisioned to be within the scope of the invention. Percent identity can be determined conventionally using known computer programs.

In certain embodiments, a RUP40 GPCR that may be used in the subject methods may comprise an amino acid sequence at least about 95%, of: at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, or at least about 99.9% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 95% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 96% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 97% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 98% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 99% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 99.1% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 99.2% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 99.3% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 99.4% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 99.5% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 99.6% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 99.7% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 99.8% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. In certain embodiments, a GPCR that may be used in the subject methods may comprise an amino acid sequence at least about 99.9% identical to amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ ID NO:7 and a specific primer that comprises the nucleotide sequence set forth in SEQ ID NO:8. By an amino acid sequence having at least, for example, 95% "identity" to amino acids 1-1,346 of SEQ ID NO:2 is meant that the amino acid sequence is identical to amino acids 1-1,346 of SEQ ID NO:2 except that it may include up to five amino acid alterations per each 100 amino acids of amino acids 1-1,346 of SEQ ID NO:2 or to the amino acid sequence encoded by a nucleic acid encoding an endogenous RUP40 receptor, said nucleic acid sequence being obtainable by performing polymerase chain reaction (PCR) on a human cDNA sample using a specific primer that comprises the nucleotide sequence set forth in SEQ II) NO:7 and a specific primer that comprises the nucleotide sequence set forth in SEQ ID NO:8. Thus, to obtain for example an amino acid sequence having at least 95% identity to amino acids 1-1,346 of SEQ ID NO:2, up to 5% (5 of 100) of the amino acid residues in the sequence may be inserted, deleted, or substituted with another amino acid compared with amino acids 1-1,346 of SEQ ID NO:2. These alternations may occur at the amino or carboxy termini or anywhere between those terminal positions, interspersed either individually among residues in the sequence or in one or more contiguous groups within the sequence.

In certain embodiments, a RUP40 GPCR that may be used in the subject methods may comprise an amino acid sequence at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, or at least about 99.9% identical to amino acids 991-1,346 of SEQ ID NO:2. In certain embodiments, a GPCR that may be used in the subject methods may comprise an amino acid sequence at least about 95% identical to amino acids 991-1,346 of SEQ ID NO:2. In certain embodiments, a GPCR that may be used in the subject methods may comprise an amino acid sequence at least about 96% identical to amino acids 991-1,346 of SEQ ID NO:2. In certain embodiments, a GPCR that may be used in the subject methods may comprise an amino acid sequence at least about 97% identical to amino acids 991-1,346 of SEQ ID NO:2. In certain embodiments, a GPCR that may be used in the subject methods may comprise an amino acid sequence at least about 98% identical to amino acids 991-1,346 of SEQ ID NO:2. In certain embodiments, a GPCR that may be used in the subject methods may comprise an amino acid sequence at least about 99% identical to amino acids 991-1,346 of SEQ ID NO:2. In certain embodiments, a GPCR that may be used in the subject methods may comprise an amino acid sequence at least about 99.1% identical to amino acids 991-1,346 of SEQ ID NO:2. In certain embodiments, a GPCR that may be used in the subject methods may comprise an amino acid sequence at least about 99.2% identical to amino acids 991-1,346 of SEQ ID NO:2. In certain embodiments, a GPCR that may be used in the subject methods may comprise an amino acid sequence at least about 99.3% identical to amino acids 991-1,346 of SEQ ID NO:2. In certain embodiments, a GPCR that may be used in the subject methods may comprise an amino acid sequence at least about 99.4% identical to amino acids 991-1,346 of SEQ ID NO:2. In certain embodiments, a GPCR that may be used in the subject methods may comprise an amino acid sequence at least about 99.5% identical to amino acids 991-1,346 of SEQ ID NO:2. In certain embodiments, a GPCR that may be used in the subject methods may comprise an amino acid sequence at least about 99.6% identical to amino acids 991-1,346 of SEQ ID NO:2. In certain embodiments, a GPCR that may be used in the subject methods may comprise an amino acid sequence at least about 99.7% identical to amino acids 991-1,346 of SEQ ID NO:2. In certain embodiments, a GPCR that may be used in the subject methods may comprise an amino acid sequence at least about 99.8% identical to amino acids 991-1,346 of SEQ ID NO:2. In certain embodiments, a GPCR that may be used in the subject methods may comprise an amino acid sequence at least about 99.9% identical to amino acids 991-1,346 of SEQ ID NO:2. By an amino acid sequence having at least, for example, 95% "identity" to amino acids 991-1,346 of SEQ ID NO:2 is meant that the amino acid sequence is identical to amino acids 991-1,346 of SEQ ID NO:2 except that it may include up to five amino acid alterations per each 100 amino acids of amino acids 991-1,346 of SEQ ID NO:2. Thus, to obtain an amino acid sequence having at least 95% identity to amino acids 991-1,346 of SEQ ID NO:2, up to 5% (5 of 100) of the amino acid residues in the sequence may be inserted, deleted, or substituted with another amino acid compared with amino acids 991-1,346 of SEQ ID NO:2. These alternations may occur at the amino or carboxy termini or anywhere between those terminal positions, interspersed either individually among residues in the sequence or in one or more contiguous groups within the sequence.

In some embodiments, a RUP40 GPCR that may be used in the subject methods comprises the amino acid sequence of a G protein-coupled receptor encoded by a complementary sequence to the sequence of a polynucleotide that hybridizes under stringent conditions to filter-bound DNA having the sequence set forth in SEQ ID NO:1. Hybridization techniques are well known to the skilled artisan. Preferred stringent hybridization conditions include overnight incubation at 42° C. in a solution comprising: 50% formamide, SxSSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA; followed by washing the filter in 0.1-0.2×SSC at about 65° C.

a. Sequence Identity

In some embodiments, the method for determining percent identity between two amino acid sequences is a method for determining the best overall match between a query sequence (e.g., the amino acid sequence of SEQ ID NO:2) and a sequence to be interrogated, also referred to as a global sequence alignment, using the FASTDB computer program based on the algorithm of Brutlag et al. [Comp App Biosci (1990) 6:237-245; the disclosure of which is hereby incorporated by reference in its entirety]. In a sequence alignment the query and interrogated sequences are both amino acid sequences. The results of said global sequence alignment is in percent identity. Preferred parameters used in a FASTDB amino acid alignment are: Matrix=PAM 0, k-tuple=2, Mismatch Penalty=1, Joining Penalty=20, Randomization Group=25, Length=0, Cutoff Score=1, Window Size=sequence length, Gap Penalty=5, Gap Size Penalty=0.05, Window Size=247 or the lenth of the interrogated amino acid sequence, whichever is shorter.

If the interrogated sequence is shorter than the query sequence due to N- or C-terminal deletions, not because of internal deletions, the results, in percent identity, must be manually corrected because the FASTDB program does not account for N- and C-terminal truncations of the interrogated sequence when calculating global percent identity. For interrogated sequences truncated at the N- and C-termini, relative to the query sequence, the percent identity is corrected by calculating the number of residues of the query sequence that are N- and C-terminal of the interrogated sequence, that are not matched/aligned with a corresponding interrogated sequence residue, as a percent of the total bses of the query sequence. Whether a residue is matched/aligned is determined by results of the FASTDB sequence alignment. This percentage is then subtracted from the perecent identity, calculated by the above FASTDB program using the specified parameters, to arrive at a final percent identity score. This final percent identity score is what is used for the purposes of the present invention. Only residues to the N- and C-termini of the interrogated sequence, which are not matched/aligned with the query sequence, are considered for the purposes of manually adjusting the percent identity score. That is, only querey amino acid residues outside the farthest N- and C-terminal residues of the interrogated sequence.

For example, a 90 amino acid residue interrogated sequence is aligned with a 100-residue query sequence to determine percent identity. The deletion occurs at the N-terminus of the interrogated sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched, the final percent identity would be 90%.

In another example, a 90-residue interrogated sequence is compared with a 100-residue query sequence. This time the deletions are internal so there are no residues at the N- or C-termini of the interrogated sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other corrections are made for the purposes of the present invention.

b. Fusion Proteins

In certain embodiments, a polypeptide of interest is a fusion protein, and may contain, for example, an affinity tag domain or a reporter domain. Suitable affinity tags include any amino acid sequence that may be specifically bound to another moiety, usually another polypeptide, most usually an antibody. Suitable affinity tags include epitope tags, for example, the V5 tag, the FLAG tag, the HA tag (from hemagglutinin influenza virus), the myc tag, and the like, as is known in the art. Suitable affinity tags also include domains for which, binding substrates are known, e.g., HIS, GST and MBP tags, as is known in the art, and domains from other proteins for which specific binding partners, e.g., antibodies, particularly monoclonal antibodies, are available. Suitable affinity tags also include any protein-protein interaction domain, such as a IgG Fc region, which may be specifically bound and detected using a suitable binding partner, e.g. the IgG Fc receptor. It is expressly contemplated that such a fusion protein may contain a heterologous N-terminal domain (e.g., an epitope tag) fused in-frame with a GPCR that has had its N-terminal methionine residue either deleted or substituted with an alternative amino acid.

Suitable reporter domains include any domain that can report the presence of a polypeptide. While it is recognized that an affinity tag may be used to report the presence of a polypeptide using, e.g., a labeled antibody that specifically binds to the tag, light emitting reporter domains are more usually used. Suitable light emitting reporter domains include luciferase (from, e.g., firefly, *Vargula, Renilla reniformis* or *Renilla muellen*), or light emitting variants thereof. Other suitable reporter, domains include fluorescent proteins, (from e.g., jellyfish, corals and other coelenterates as such those from *Aequoria, Renilla, Ptilosarcus, Stylatula* species), or light emitting variants thereof. Light emitting variants of these reporter proteins are very well known in the art and may be brighter, dimmer, or have different excitation and/or emission spectra, as compared to a native reporter protein. For example, some variants are altered such that they no longer appear green, and may appear blue, cyan, yellow, enhanced yellow red (termed BFP, CEP, YFP eYFP and RFP, respectively) or have other emission spectra, as is known in the art. Other suitable reporter domains include domains that can report the presence of a polypeptide through a biochemical or color change, such as β-galactosidase, β-glucuronidase, chloramphenicol acetyl transferase, and secreted embryonic alkaline phosphatase.

Also as is known in the art, an affinity tags or a reporter domain may be present at any position in a polypeptide of interest. However, in most embodiments, they are present at the C- or N-terminal end of a polypeptide of interest.

2. Nucleic Acids Encoding GPCR Polypeptides of Interest

Since the genetic code and recombinant techniques for manipulating nucleic acid are known, and the amino acid sequences of GPCR polypeptides of interest described as above, the design and production of nucleic acids encoding a GPCR polypeptide of interest is well within the skill of an artisan. In certain embodiments, standard recombinant DNA technology (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.) methods are used. For example, GPCR coding sequences may be isolated from a library of GPCR coding sequence using any one or a combination of a variety of recombinant methods that do not need to be described herein. Subsequent substitution, deletion, and/or addition of nucleotides in the nucleic acid sequence encoding a protein may also be done using standard recombinant DNA techniques.

For example, site directed mutagenesis and subcloning may be used to introduce/delete/substitute nucleic acid residues in a polynucleotide encoding a polypeptide of interest. In other embodiments, PCR may be used Nucleic acids encoding a polypeptide of interest may also be made by chemical synthesis entirely from oligonucleotides (e.g., Cello et al., Science (2002) 297:1016-8).

In some embodiments, the codons of the nucleic acids encoding polypeptides of interest are optimized for expression in cells of a particular species, particularly a mammalian, e.g., mouse, rat, hamster, non-human primate, or human, species. In some embodiments, the codons of the nucleic acids encoding polypeptides of interest are optimized for expression in cells of a particular species, particularly an amphibian species.

a. Vectors

The invention further provides vectors (also referred to as "constructs") comprising a subject nucleic acid. In many embodiments of the invention, the subject nucleic acid sequences will be expressed in a host after the sequences have been operably linked to an expression control sequence, including, e.g. a promoter. The subject nucleic acids are also typically placed in an expression vector that can replicate in a host cell either as an episome or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). Vectors, including single and dual expression cassette vectors are well known in the art (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used.

A variety of expression vectors are available to those in the art for purposes of producing a polypeptide of interest in a cell. One suitable vector is pCMV, which is used in certain embodiments. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351.

The subject nucleic acids usually comprise an single open reading frame encoding a subject polypeptide of interest, however, in certain embodiments, since the host cell for expression of the polypeptide of interest may be a eukaryotic cell, e.g., a mammalian cell, such as a human cell, the open reading frame may be interrupted by introns. Subject nucleic acid are typically part of a transcriptional unit which may contain, in addition to the subject nucleic acid 3' and 5' untranslated regions (UTRs) which may direct RNA stability, translational efficiency, etc. The subject nucleic acid may also be part of an expression cassette which contains, in addition to the subject nucleic acid a promoter, which directs the transcription and expression of a polypeptide of interest, and a transcriptional terminator.

Eukaryotic promoters can be any promoter that is functional in a eukaryotic host cell, including viral promoters and promoters derived from eukaryotic genes. Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA)

79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

In certain embodiments, a subject vector may also provide for expression of a selectable marker. Suitable vectors and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thymidine kinase gene, the dihydrofolate reductase gene, the xanthine-guanine phosphoribosyl transferase gene, CAD, the adenosine deaminase gene, the asparagine synthetase gene, the antibiotic resistance genes, e.g. tetr, ampr, Cmr or cat, kanr or neor (aminoglycoside phosphotransferase genes), the hygromycin B phosphotransferase gene, and the like.

As mentioned above, polypeptides of interest may be fusion proteins that contain an affinity domain and/or a reporter domain. Methods for making fusions between a reporter or tag and a GPCR, for example, at the C- or N-terminus of the GPCR, are well within the skill of one of skill in the art (e.g. McLean et al, Mol. Pharma. Mol. Pharmacol. 1999 56:1182-91; Ramsay et al., Br. J. Pharmacology, 2001, 315-323) and will not be described any further. It is expressly contemplated that such a fusion protein may contain a heterologous N-terminal domain (eg., an epitope tag) fused in-frame with a GPCR that has had its N-terminal methionine residue either deleted or substituted with an alternative amino acid. It is appreciated that a polypeptide of interest may first be made from a native polypeptide and then operably linked to a suitable reporter/tag as described above.

The subject nucleic acids may also contain restriction sites, multiple cloning sites, primer binding sites, ligatable ends, recombination sites etc., usually in order to facilitate the construction of a nucleic acid encoding a polypeptide of interest b. Host Cells The invention further provides host cells comprising a vector comprising a subject nucleic acid. Suitable host cells include prokaryotic, e.g., bacterial cells (for example *E. coli*), as well as eukaryotic cells e.g. an animal cell (for example an insect, mammal, fish, amphibian, bird or reptile cell), a plant cell (for example a maize or *Arabidopsis* cell), or a fungal cell (for example a *S. cerevisiae* cell). In certain embodiments, any cell suitable for expression of a polypeptide of interest-encoding nucleic acid may be used as a host cell. Usually, an animal host cell line is used, examples of which are as follows: monkey kidney cells (COS cells), monkey kidney CVI cells transformed by SV40 (COS-7, ATCC CRL 165 1); human embryonic kidney cells (HEX-293 ["293"], Graham et al. J. Gen Virol. 36:59 (1977)); HEK-293T ["293T"] cells; baby hamster kidney cells (BHK, ATCC CCL 10); chinese hamster ovary-cells (CHO, Urlaub and Chasin, Proc. Natl. Acad. Sci. (USA) 77:4216, (1980); Syrian golden hamster cells MCB3901 (ATCC CRL-9595); mouse sertoli cells (TM4, Mather, Biol. Reprod. 23:243-251 (1980)); monkey kidney cells (CV1 ATCC CCL 70); african green monkey kidney cells (VERO-76, ATCC CRL-1587); human cervical carcinoma cells (BELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TR1 cells (Mather et al., Annals N.Y. Acad. Sci. 383:44-68 (1982)); NIH/3T3 cells (ATCC CRL-1658); and mouse L cells (ATCC CCL-1). In certain embodiments, melanophores are used. Melanophores are skin cells found in lower vertebrates. Relevant materials and methods will be followed according to the disclosure of U.S. Pat. No. 5,462,856 and U.S. Pat. No. 6,051,386. These patent disclosures are hereby incorporated by reference in their entirety. Additional cell lines will become apparent to those of ordinary skill in the art, and a wide variety of cell lines are available from the American Type Culture Collection, 10801 University Boulevard, Manassas, Va. 20110-2209.

B. Screening of Candidate Compounds

1. Generic GPCR Screening Assay Techniques

When a G protein receptor becomes active, it binds to a G protein (e.g., Gq, Gs, Gi, Go, Gz) and stimulates the binding of GTP to the G protein. The G protein then acts as a GTPase and slowly hydrolyzes the GTP to GDP, whereby the receptor, under normal conditions, becomes deactivated. However, activated receptors continue to exchange GDP to GTP. A non-hydrolyzable analog of GTP, [$^{35}$S]GTPγS, can be used to monitor enhanced binding to membranes which express activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. A preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists, inverse agonists or antagonists), in some embodiments further screening to confirm that the compounds have interacted at the receptor site is preferred. For example, a compound identified by the "generic" assay may not bind to the receptor, but may instead merely "uncouple" the G protein from the intracellular domain.

In alternative embodiments, candidate compounds can be identified through initial screening using a "specific" G protein-coupled receptor assay as provided infra by way of illustration and not limitation.

a. Gs, Gi, Go and Gz.

Gs stimulates the enzyme adenylyl cyclase. Gi (and Gz and Go), on the other hand, inhibit adenylyl cyclase Adenylyl cyclase catalyzes the conversion of ATP to cAMP; thus, activated GPCRs that couple the Gs protein are associated with increased cellular levels of cAMP. On the other hand, activated GPCRs that couple Gi (or Gz, Go) protein are associated with decreased cellular levels of cAMP. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; in some embodiments a preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, an activated Gs-linked receptor causes the accumulation of cAMP that then activates the gene and expression of the reporter protein. The reporter protein such as β-galactosidase or luciferase can then be detected using standard biochemical assays (Chen et al. 1995).

b. Gq.

Gq is associated with activation of the enzyme phospholipase C, which in turn hydrolyzes the phospholipid PIP2, releasing two intracellular messengers: diacyclglycerol (DAG) and inositol 1,4,5-triphosphate (IP3). Increased accumulation of IP3 is associated with activation of Gq- and Go-associated receptors. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Assays that detect 23 accumulation can be utilized to determine if a candidate compound is, e.g., an inverse agonist to a Gq-associated receptor (i.e., such a compound would decrease the levels of IP3). Gq-associated receptors can also been examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively active GPCR or a non-endogenous, constitutively activated GPCR, for use in screening of candidate compounds for the direct identification of inverse agonists or agonists provides an interesting screening challenge in that, by definition, the receptor is active even in the absence of an endogenous ligand bound thereto. Thus, in order to differentiate between, e.g., the non-endogenous receptor in the presence of a candidate compound and the non-endogenous receptor in the absence of that compound, with an aim of such a differentiation to allow for an understanding as to whether such compound may be an inverse agonist or agonist or have no affect on such a receptor, in some embodiments it is preferred that an approach be utilized that can enhance such differentiation. In some embodiments, a preferred approach is the use of a GPCR Fusion Protein.

Generally, once it is determined that a non-endogenous GPCR has been constitutively activated using the assay techniques set forth above (as well as others known to the art-skilled), it is possible to determine the predominant G protein that couples with the endogenous GPCR. Coupling of the G protein to the GPCR provides a signaling pathway that can be assessed. In some embodiments it is preferred that screening take place using a mammalian expression system, as such a system will be expected to have endogenous G protein therein. Thus, by definition, in such a system, the non-endogenous, constitutively activated GPCR will continuously signal. In some embodiments it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the non-endogenous GPCR The GPCR Fusion Protein is preferred for screening with either an endogenous, constitutively active GPCR or a non-endogenous, constitutively activated GPCR because such an approach increases the signal that is generated in such screening techniques. This is important in facilitating a significant "signal to noise" ratio; such a significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. Important criteria in the construction of such a GPCR Fusion Protein construct include but are not limited to, that the GPCR sequence and the G protein sequence both be in-frame (preferably, the sequence for the endogenous GPCR is upstream of the G protein sequence), and that the "stop" codon of the GPCR be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). Based upon convenience, it is preferred to use a spacer. In some embodiments it is preferred, that the G protein that couples to the non-endogenous GPCR will have been identified prior to the creation of the GPCR Fusion Protein construct. Because there are only a few G proteins that have been identified, it is preferred that a construct comprising the sequence of the G protein (i.e., a universal G protein construct, see Example 4(a) below) be available for insertion of an endogenous GPCR sequence therein; this provides for further efficiency in the context of large-scale screening of a variety of different endogenous GPCRs having different sequences.

As noted above, activated GPCRs that couple to Gi, Go and Gz are expected to inhibit the formation of cAMP making assays based upon these types of GPCRs challenging [i.e., the cAMP signal decreases upon activation, thus making the direct identification of, e.g., agonists (which would further decrease this signal) challenging]. As will be disclosed herein, it has been ascertained that for these types of receptors, it is possible to create a GPCR Fusion Protein that is not based upon the GPCR's endogenous G protein, in an effort to establish a viable cyclase-based assay. Thus, for example, an endogenous Gi coupled receptor can be fused to a Gs protein—such a fusion construct, upon expression, "drives" or "forces" the endogenous GPCR to couple with, e.g., Gs rather than the "natural" Gi protein, such that a cyclase-based assay can be established. Thus, for Gi, Go and Gz coupled receptors, in some embodiments it is preferred that when a GPCR Fusion Protein is used and the assay is based upon detection of adenylyl cyclase activity, that the fusion construct be established with Gs (or an equivalent G protein that stimulates the formation of the enzyme adenylyl cyclase).

TABLE B

| G protein | Effect of cAMP Production upon Activation of GPCR (i.e., constitutive activation or agonist binding) | Effect of IP3 Accumulation upon Activation of GPCR (i.e., constitutive activation or agonist binding) | Effect of cAMP Production upon contact with an Inverse Agonist | Effect on IP3 Accumulation upon contact with an Inverse Agonist |
|---|---|---|---|---|
| Gs | Increase | N/A | Decrease | N/A |
| Gi | Decrease | N/A | Increase | N/A |
| Gz | Decrease | N/A | Increase | N/A |
| Go | Decrease | N/A | Increase | N/A |
| Gq | N/A | Increase | N/A | Decrease |

Equally effective is a G Protein Fusion construct that utilizes a Gq Protein fused with a Gs, Gi, Go or Gz Protein. In some embodiments a preferred fusion construct can be accomplished with a Gq Protein wherein the first six (6) amino acids of the G-protein α-subunit ("Gαq") is deleted and the last five (5) amino acids at the C-terminal end of Gαq is replaced with the corresponding amino acids of the Gα of the G protein of interest. For example, a fusion construct can have a Gq (6 amino acid deletion) fused with a Gi Protein, resulting in a "Gq/Gi Fusion Construct". This fusion construct will forces the endogenous Gi coupled receptor to couple to its non-endogenous G protein, Gq, such that the second messenger, for example, inositol triphosphate or diacylglycerol, can be measured in lieu of cAMP production.

4. Co-transfection of a Target Gi Coupled GPCR with a Signal-Enhancer Gs Coupled GPCR (cAMP Based Assays)

A Gi coupled receptor is known to inhibit adenylyl cyclase, and, therefore, decreases the level of cAMP production, which can make the assessment of cAMP levels challenging. In some embodiments, an effective technique in measuring the decrease in production of cAMP as an indication of activation of a receptor that predominantly couples Gi upon activation can be accomplished by co-transfecting a signal enhancer, e.g., a non-endogenous, constitutively activated receptor that predominantly couples with Gs upon activation (e.g., TSHR-A623I; see infra), with the Gi linked GPCR. As is apparent, activation of a Gs coupled receptor can be determined based upon an increase in production of cAMP. Activation of a Gi coupled receptor leads to a decrease in production cAMP. Thus, the co-transfection approach is intended to advantageously exploit these "opposite" affects. For example, co-transfection of a non-endogenous, constitutively activated Gs coupled receptor (the "signal enhancer") with expression vector alone provides a baseline cAMP signal (i.e., although the Gi coupled receptor will decrease cAMP levels, this "decrease" will be relative to the substantial increase in cAMP levels established by constitutively activated Gs coupled signal enhancer). By then co-transfecting the signal enhancer with the "target receptor", an inverse agonist of the Gi coupled target receptor will increase the measured cAMP signal, while an agonist of the Gi coupled target receptor will decrease this signal.

Candidate compounds that are directly identified using this approach should be assessed independently to ensure that these do not target the signal enhancing receptor (this can be done prior to or after screening against the co-transfected receptors).

C. Medicinal Chemistry
   Candidate Compounds

Any molecule known in the art can be tested for its ability to modulate (increase or decrease) the activity of a GPCR of the present invention. For identifying a compound that modulates activity, candidate compounds can be directly provided to a cell expressing the receptor.

This embodiment of the invention is well suited to screen chemical libraries for molecules which modulate, e.g., inhibit, antagonize, or agonize, the amount of, or activity of, a receptor. The chemical libraries can be peptide libraries, peptidomimetic libraries, chemically synthesized libraries, recombinant, e.g., phage display libraries, and in vitro translation-based libraries, other non-peptide synthetic organic libraries, etc. This embodiment of the invention is also well suited to screen endogenous candidate compounds comprising biological materials, including but not limited to plasma and tissue extracts, and to screen libraries of endogenous compounds known to have biological activity.

In some embodiments direct identification of candidate compounds is conducted in conjunction with compounds generated via combinatorial chemistry techniques, whereby thousands of compounds are randomly prepared for such analysis. The candidate compound may be a member of a chemical library. This may comprise any convenient number of individual members, for example tens to hundreds to thousand to millions of suitable compounds, for example peptides, peptoids and other oligomeric compounds (cyclic or linear), and template-based smaller molecules, for example benzodiazepines, hydantoins, biaryls, carbocyclic and polycyclic compounds (e.g., naphthalenes, phenothiazines, acridines, steroids etc.), carbohydrate and amino acid derivatives, dihydropyridines, benzhydryls and heterocycles (e.g., trizines, indoles, thiazolidines etc.). The numbers quoted and the types of compounds listed are illustrative, but not limiting. Preferred chemical libraries comprise chemical compounds of low molecular weight and potential therapeutic agents.

Exemplary chemical libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708-4712) may be used.

In another embodiment of the present invention, combinatorial chemistry can be used to identify modulators of the GPCRs of the present invention. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See e.g., Matter, 1997, Journal of Medicinal Chemistry 40:1219-1229).

One method of combinatorial chemistry, affinity fingerprinting, has previously been used to test a discrete library of small molecules for binding affinities for a defined panel of proteins. The fingerprints obtained by the screen are used to predict the affinity of the individual library members for other proteins or receptors of interest (in the instant invention, the receptors of the present invention). The fingerprints are compared with fingerprints obtained from other compounds known to react with the protein of interest to predict whether the library compound might similarly react. For example, rather than testing every ligand in a large library for interaction with a complex or protein component, only those ligands having a fingerprint similar to other compounds known to have that activity could be tested. (See, e.g., Kauvar et al., 1995, Chemistry and Biology 2:107-118; Kauvar, 1995, Affinity fingerprinting, Pharmaceutical Manufacturing International. 8:25-28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

Candidate Compounds Identified as Modulators

Generally, the results of such screening will be compounds having unique core structures; thereafter, these compounds may be subjected to additional chemical modification around a preferred core structures) to further enhance the medicinal properties thereof. Such techniques are known to those in the art and will not be addressed in detail in this patent document.

In some embodiments, said identified modulator is bioavailable. A number of computational approaches available to those of ordinary skill in the art have been developed for prediction of oral bioavailability of a drug [Ooms et al., Biochim Biophys Acta (2002) 1587:118-25; Clark & Grootenhuis, Curr OpinDrug Discov Devel (2002) 5:382-90; Cheng et al., J Comput Chem (2002) 23:172-83; Norinder & Haeberlein, Adv Drug Deliv Rev (2002) 54:291-313; Matter et al., Comb Chem High Throughput Screen (2001) 4:453-75; Podlogar & Muegge, Curr Top Med Chem (2001) 1:257-75; the disclosure of each of which is hereby incorporated by reference in its entirety). Furthermore, positron emission tomography (PET) has been successfully used by a number of groups to obtain direct measurements of drug distribution, including an assessment of oral bioavailability, in the mammalian body following oral administration of the drug, including non-human primate and human body [Noda et al., J Nucl Med (2003) 44:105-8; Gulyas et al., Eur J Nucl Med Mol Imaging (2002) 29:1031-8; Kanerva et al., Psychopharmacology (1999) 145:76-81; the disclosure of each of which is hereby incorporated by reference in its entirety]. Also, see infra, including Example 18.

D. Pharmaceutical Compositions

The invention provides methods of treatment (and prevention) by administration to an individual in need of said treatment (or prevention) a therapeutically effect amount of a modulator of the invention [also see, e.g., PCT Application Number PCT/IB02/01461 published as WO 02/066505 on 29 Aug. 2002; the disclosure of which is hereby incorporated by reference in its entirety]. In a preferred aspect, the modulator is purified. The individual is preferably an animal including, but not limited to animals such as cows, pigs, horses, chickens, cats, dogs, rabbits, rats, mice, etc., and is preferably a mammal, and most preferably human.

Modulators of the invention can be administered to non-human animals [see Examples, infra] and/or humans, alone or in pharmaceutical or physiologically acceptable compositions where they are mixed with suitable carriers or excipient(s) using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.).

The pharmaceutical or physiologically acceptable composition is then provided at therapeutically effective dose. A therapeutically effective dose refers to that amount of a modulator sufficient to result in prevention or amelioration of symptoms or physiological status of a heart disease. Heart disease includes but is not limited to congestive heart failure, congestive cardiomyopathy, heart hypertrophy, left ventricular hypertrophy, right ventricular hypertrophy, post-infarction heart rupture, ventricular septal rupture, endocarditis (including bacterial), heart aneurysm, pulmonary heart disease, rheumatic heart disease, and ventricular dysfunction. Heart disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Heart disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy. In other embodiments, a therapeutically effective dose refers to that amount of a modulator sufficient to result in prevention or amelioration of symptoms or physiological status of a hypertrophic cardiomyopathy resulting from a disorder selected from the group consisting of post-myocardial infarction remodeling, cardiac valve disease, sustained cardiac afterload, myocarditis, and familial hypertrophic cardiomyopathy. In some embodiments, a therapeutically effective dose refers to that amount of a modulator sufficient to result in prevention or amelioration of symptoms or physiological status of a congenital heart defect. Congenital heart defect includes but is not limited to aortic coarctation, aortopulmonary septal defect, trilogy of FaNot, ventricular heart septal defect, and familial hypertrophic cardiomyopathy. In some embodiments, a therapeutically effective dose refers to that amount of a modulator sufficient to result in prevention or amelioration of symptoms or physiological status of a disorder presenting with enlarged heart.

It is expressly considered that the modulators of the invention may be provided alone or in combination with other pharmaceutically or physiologically acceptable compounds. Other compounds for the treatment of disorders of the invention are currently well known in the art. One aspect of the invention encompasses the use according to embodiments disclosed herein further comprising one or more agents selected from the group consisting of captopril, enalapril maleate, lininopril, ramipril, perindopril, furosemide, torasemide, chlorothiazide, hydrochlorothiazide, amiloride hydrochloride, spironolactone, atenolol, bisoprolol, carvedilol, metoprolol tartrate, and digoxin. In some embodiments said disorder of the invention is a heart disease. Heart disease includes but is not limited to congestive heart failure, congestive cardiomyopathy, heart hypertrophy, left ventricular hypertrophy, right ventricular hypertrophy, post-infarction heart rupture, ventricular septal rupture, endocarditis (including bacterial), heart aneurystn, pulmonary heart disease, rheumatic heart disease, and ventricular dysfunction. Heart disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Heart disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy. In some embodiments said disorder of the invention is hypertrophic cardiomyopathy resulting from a hemodynamic or genetic disorder. In some embodiments, said disorder of the invention is a hypertrophic cardiomyopathy resulting from a disorder selected from the group consisting of post-myocardial infarction remodeling, cardiac valve disease, sustained cardiac afterload, myocarditis, and familial hypertrophic cardiomyopathy. In some embodiments, said disorder of the invention is a congenital heart defect. Congenital heart defect includes but is not limited to aortic coarctation, aortopulmonary septal defect, trilogy of Fallot, ventricular heart septal defect, and familial hypertrophic cardiomyopathy. In some embodiments, said disorder of the invention is a disorder presenting with an enlarged heart.

Routes of Administration

Suitable routes of administration include oral, nasal, rectal, transmucosal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other particularly preferred routes of administration are aerosol and depot formulation. Sustained release formulations, particularly depot, of the invented medicaments are expressly contemplated. In some embodiments, route of administration is oral.

Composition/Formulation

Pharmaceutical or physiologically acceptable compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically or physiologically acceptable carver and at least one modulator of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed captulse made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liqid paraffin, or lliquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs for a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for ue in an inhaler or insufflator, may be forumulated containing a powder mix of the compound and a suitable powder base such as lactose or starch.

The compounds may be formulated for parenteral administration by injection, e.g., by bolus injection or continuous infusion. Formulations for injection may be presented in unit dosage for, e.g., in ampoules or in muti-dose containers, with an added preservative. The compositions may take such forms as suspension, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspension may contain substances that increase the viscosity of the suspension, such as sodium carboxymethyl cellulose, sorbitol, or dextran. Optionally, the suspension may also contain suitable stabilizers or agents that increase the solubility of the compounds to alloNk for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt In a particular embodiment, the compounds can be delivered via a controlled release system. In one embodiment, a pump may be used (Langer, supra; Sefton, 1987, CRC Crit. Ref. Biomed. Eng. 14:201-240; Buchwald et al., 1980, Surgery 88:507-516; Saudek et al., 1989, N. Engl. J. Med. 321: 574-579). In another embodiment, polymeric materials can be used (Medical Applications of Controlled Release, Langer and Wise, eds., CRC Press, Boca Raton, Fla., 1974; Controlled Drug Bioavailability, Drug Product Design and Performance, Smolen and Ball, eds., Wiley, New York, 1984; Ranger and Peppas, 1983, Macromol. Sci. Rev. Macromol. Chem. 23:61; Levy et al., 1985, Science 228:190-192; During et al., 1989, Ann. Neurol. 25:351-356; Howard et al., 1989, J. Neurosurg. 71:858-863). Other controlled release systems are discussed in the review by Langer (1990, Science 249: 1527-1533).

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for modulator stabilization may be employed.

The pharmaceutical or physiologically acceptable compositions also may comprise suitable solid or gel phase carriers or excipients. Examples of such carriers or escipients include but are not limited to calcium carbonate, calcium phosphate, various sugars, starches, cellulos derivatives, gelatin, and polymers such as polyethylene glycols.

Effective Dosage

Pharmaceutical or physiologically acceptable compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is wll within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to cell death-protective in an in vitro system. (See Examples, infra, for in vitro assays and in vivo animal models.) Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the $LD_{50}$ (the dose lethal to 50% of the test population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred.

The data obtained from these cell culture assays and animal studies can be used in formulating a range of dosage for use in humans. The dosage of such compounds lies preferably within a range of circulating concentrations that include the $ED_{50}$, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to prevent or treat a disorder of the invention, depending on the particular situation. Dosages necessary to achieve these effects will depend on individual characteristics and route of administration.

Dosage intervals can also be determined using the value for the minimum effective concentration. Compounds should be administered using a regimen that maintains plasma levels above the minimum effective concentration for 10-90% of the time, preferably between 30-99%, and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration, and the judgement of the prescribing physician.

A preferred dosage range for the amount of a modulator of the invention, which can be administered on a daily or regular basis to achieve desired results, the prevention or treatment of a disorder of the invention, is 0.1-100 mg/kg body mass. Other preferred dosage range is 0.1-30 mg/kg body mass. Other preferred dosage range is 0.1-10 mg/kg body mass. Other preferred dosage range is 0.1-3.0 mg/kg body mass. Of course, these daily dosages can be delivered or administered in small amounts periodically during the course of a day. It is noted that these dosage ranges are only preferred ranges and are not meant to be limiting to the invention. In some embodiments said disorder of the invention is a heart disease. Heart disease includes but is not limited to congestive heart failure, congestive cardiomyopathy, heart hypertrophy, left ventricular hypertrophy, right ventricular hypertrophy, post-infarction heart rupture, ventricular septal rupture, endocarditis (including bacterial), heart aneurysm, pulmonary heart disease, rheumatic heart disease, and ventricular dysfunction. Heart disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Heart disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy. In some embodiments said disorder of the invention is hypertrophic cardiomyopathy resulting from a hemodynamic or genetic disorder. In some embodiments, said disorder of the invention is a hypertrophic cardiomyopathy resulting from a disorder selected from the group consisting of post-myocardial infarction remodeling, cardiac valve disease, sustained cardiac afterload, myocarditis, and familial hypertrophic cardiomyopathy. In some embodiments, said disorder of the invention is a congenital heart defect. Congenital heart defect includes but is not limited to aortic coarctation, aortopulmonary septal defect, trilogy of Fallot, ventricular heart septal defect, and familial hypertrophic cardiomyopathy. In some embodiments, said disorder of the invention is a disorder presenting with an enlarged heart.

E. Methods of Treatment

The invention is drawn inter alia to methods of preventing or treating a disorder of the invention, comprising providing an individual in need of such treatment with a modulator of the invention. In some embodiments said disorder of the invention is a heart disease. Heart disease includes but is not limited to congestive heart failure, congestive cardiomyopathy, heart hypertrophy, left ventricular hypertrophy, right ventricular hypertrophy, post-infarction heart rupture, ventricular septal rupture, endocarditis (including bacterial), heart aneurysm, pulmonary heart disease, rheumatic heart disease, and ventricular dysfunction. Heart disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Heart disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy. In some embodiments, said modulator is an inverse agonist or an antagonist. In some embodiments said disorder of the invention is hypertrophic cardiomyopathy resulting from a hemodynamic or genetic disorder. In some embodiments, said disorder of the invention is a hypertrophic cardiomyopathy resulting from a disorder selected from the group consisting of post-myocardial infarction remodeling, cardiac valve disease, sustained cardiac afterload, myocarditis, and familial hypertrophic cardiomyopathy. In some embodiments, said disorder of the invention is a congenital heart defect. Congenital heart defect includes but is not limited to aortic coarctation, aortopulmonary septal defect, trilogy of Fallot, ventricular heart septal defect, and familial hypertrophic cardiomyopathy. In some embodiments, said disorder of the invention is a disorder presenting with an enlarged heart. In some embodiments, said modulator is an inverse agonist or an antagonist. In some embodiments, said modulator is orally bioavailable. In some embodiments, the modulator is provided to the individual in a pharmaceutical composition that is taken orally. Preferably the individual is a mammal, and most preferably a human.

F. Other Utility

Agents that modulate (i.e., increase, decrease, or block) RUP40 receptor functionality may be identified by contacting a candidate compound with RUP40 receptor and determining the effect of the candidate compound on RUP40 receptor functionality. The selectivity of a compound that modulates the functionality of a RUP40 receptor can be evaluated by comparing its effects on the RUP40 receptor to its effects on a plurality of G protein-coupled receptors other than RUP40. In some embodiments, the selectivity of a compound that modulates the functionality of an endogenous human RUP40 receptor can be evaluated by comparing its effect on the endogenous human RUP40 receptor to its effects on a plurality of endogenous human G protein-coupled receptors other than RUP40. Following identification of compounds that modulate RUP40 receptor functionality, such candidate compounds may be further tested in other assays including, but not limited to, in vivo models, in order to confirm or quantitate their activity. Modulators of RUP40 receptor functionality are therapeutically useful for the prevention or treatment of diseases and physiological conditions in which normal or aberrant RUP40 receptor functionality is involved.

Agents that are modulators (i.e., increase, decrease, or block) of a cardiovascular disorder may be identified by contacting a candidate compound with a RUP40 receptor and determining the effect of the candidate compound on RUP40 receptor functionality. The selectivity of a compound that modulates the functionality of a RUP40 receptor can be evaluated by comparing its effects on the RUP40 receptor to its effects on a plurality of G protein-coupled receptors other than RUP40. In some embodiments, the selectivity of a compound that modulates the functionality of an endogenous human RUP40 receptor can be evaluated by comparing its effect on the endogenous human RUP40 receptor to its effects on a plurality of endogenous human G protein-coupled receptors other than RUP40. Following identification of compounds that modulate RUP40 receptor functionality, such candidate compounds may be further tested in other assays including, but not limited to, in vivo models, in order to confirm or quantitate their activity. Modulators of RUP40 receptor functionality are therapeutically useful for the prevention or treatment of heart disease, including hypertrophic cardiomyopathy and congestive heart failure, in particular hypertrophic cardiomyopathy resulting from post-myocardial infarction remodeling, cardiac valve disease, sustained cardiac afterload, myocarditis; and familial hypertrophic cardiomyopathy.

In other embodiments, agents that are modulators (i.e., increase, decrease, or block) of a heart disease may be identified by contacting a candidate compound with a RUP40 receptor and determining the effect of the candidate compound on RUP40 receptor expression. In some embodiments, the agent reduces expression of RUP40 receptor in a cell. In some embodiments, the agent reduces expression of RUP40 receptor in a cardiomyocyte. In some embodiments, the agent reduces expression of RUP40 receptor in a human cardiomyocyte. In some embodiments, the RUP40 receptor is endogenously expressed by the cell or cardiomyocyte. In some embodiments, a level of RUP40 receptor expression is measured using anti-RUP40 receptor antibody. By way of example and not limitation, the anti-RUP40 receptor antibody may be that described in Example 12. Those of skill in the art are credited with the ability to produce antibody to human, rat or mouse RUP40 receptor that may be used to measure a level of RUP40 expression in a cell. In some embodiments, a level of RUP40 receptor expression is measured using radiolableled ligand specific for RUP40 receptor (see infra). In some embodiments, a level of RUP40 receptor expression is measured by Northern blot or RT-PCR.

The present invention also relates to a method of identifying whether a candidate compound is an agent that reduces expression of RUP40 receptor in a cell, said method comprising the steps of
 (a) contacting or not contacting a plurality of cells comprising RUP40 receptor with a candidate compound;
 (b) measuring the level of RUP40 receptor expression in the cells contacted with the candidate compound and the level of RUP40 receptor expression in the cells not contacted with the candidate compound; and
 (c) comparing the level of RUP40 receptor expression in the cells contacted with the candidate compound with the level of RUP40 receptor expression in the cells not contacted with the candidate compound; wherein a reduction in the level of RUP40 receptor expression in the cells contacted with the candidate compound compared with the level of RUP40 receptor expression in the cells not contacted with the candidate compound is indicative of the candidate compound being an agent that reduces expression of RUP40 receptor in a cell.

The present invention also relates to a method of identifying whether a candidate compound is an agent that decreases or blocks a heart disease, said method comprising the steps of:
 (a) contacting or not contacting a plurality of cells comprising RUP40 receptor with a candidate compound;
 (b) measuring the level of RUP40 receptor expression in the cells contacted with the candidate compound and the level of RUP40 receptor expression in the cells not contacted with the candidate compound; and
 (c) comparing the level of RUP40 receptor expression in the cells contacted with the candidate compound with the level of RUP40 receptor expression in the cells not contacted with the candidate compound; wherein a reduction in the level of RUP40 receptor expression in the cells contacted with the candidate compound compared with the level of RUP40 receptor expression in the cells not contacted with the candidate compound is indicative of the candidate compound being an agent that decreases or blocks a heart disease.

The present invention relates to said agent that reduces RUP40 expression in a cell (e.g., a cardiomyocyte), to a composition comprising said agent (e.g., a pharmaceutical composition), and to methods of using said composition (e.g., for the prevention of or treatment for a heart disease, such as for hypertrophic cardiomyopathy or congestive heart failure), wherein the compound is antisense nucleic acid (e.g., antisense RNA). The present invention relates to said agent that reduces RUP40 expression in a cell (e.g., a cardiomyocyte), to a composition comprising said agent (e.g., a pharmaceutical composition), and to methods of using said composition (e.g., for the prevention of or treatment for a heart disease, such as for hypertrophic cardiomyopathy or congestive heart failure), wherein the compound is a small interfering RNA (siRNA) or short hairpin RNA (shRNA) molecule comprising a nucleotide sequence derived from the nucleotide sequence of a RUP40 GPCR-encoding gene according to standard procedures. As will be known to the skilled artisan, siRNA, shRNA and antisense RNA are generally capable of modulating expression of a target gene [see, e.g., Holmlund J T, Ann NY Acad Sci (2003) 1002:244-251; and Devroe et al, Expert Opin Biol Ther (2004) 4:319-327; the disclosure of each of which is hereby incorporated by reference in its entirety].

The present invention also relates to radioisotope-labeled versions of compounds of the invention identified as modulators or ligands of RUP40 that would be useful not only in radio-imaging but also in assays, both in vitro and in vivo, for localizing and quantitating RUP40 in tissue samples, including human, and for identifying RUP40 ligands by inhibition binding of a radioisotope-labeled compound. It is a further object of this invention to develop novel RUP40 assays of which comprise such radioisotope-labeled compounds. By way of illustration and not limitation, it is envisioned that elevated ventricular RUP40 above the normal range visualized through radio-imaging may identify an individual at risk for or progressing toward a cardiovascular disorder of the invention, e.g., hypertrophic cardiomyopathy or congestive heart failure.

The present invention embraces radioisotope-labeled versions of compounds of the invention identified as modulators or ligands of RUP40.

In some embodiments, a radioisotope-labeled version of a compound is identical to the compound, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (deuterium), $^3$H (tritium), $^{11}$C, $^{13}$C, $^{14}$C, $^{13}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. The radionuclide that is incorporated in the instant radio-labeled compound will depend on the specific application of that radio-labeled compound. For example, for in vitro RUP40 labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, 123I, $^{124}$I, $^{131}$I, $^{75}$Br, $^{76}$Br or $^{77}$Br will generally be most useful. In some embodiments, the radionuclide is selected from the group consisting of $^3$H, $^{11}$C, $^{18}$F, $^{14}$C, $^{125}$I, $^{124}$I, $^{131}$I, $^{35}$S and $^{82}$Br.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3$H]—This procedure is rather inexpensive and requires precursors containing reducible functional groups such as aldehydes, ketones, lactones, esters, and the like.

C. Reduction with Lithium Aluminum Hydride [$^3$H]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I. A represented procedure was reported by Zhu, D.-G. and co-workers in *J. Org. Chem.* 2002, 67, 943-948.

B. Ortho $^{125}$Iodination of phenols—This procedure allows for the incorporation of $^{125}$I at the ortho position of a phenol as reported by Collier, T. L. and co-workers in *J. Labeled Compd Radiopharm.* 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labeled Compd Radiopharm.* 2001, 44, S280-S282.

In some embodiments, a radioisotope-labeled version of a compound is identical to the compound, but for the addition of one or more substituents comprising a radionuclide. In some further embodiments, the compound is a polypeptide. In some further embodiments, the compound is an antibody or an antigen-binding fragment thereof. In some further embodiments, said antibody is monoclonal. Suitable said radionuclide includes but is not limited to $^2$H (deuterium), $^3$H (tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compound will depend on the specific application of that radio-labeled compound. For example, for in vitro RUP40 labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. In some embodiments, the radionuclide is selected from the group consisting of $^3$H, $^{11}$C, $^{18}$F, $^{14}$C, $^{125}$I, $^{124}$I, $^{131}$I, $^{35}$S and $^{82}$Br.

Methods for adding one or more substituents comprising a radionuclide are within the purview of the skilled artisan and include, but are not limited to, addition of radioisotopic iodine by enzymatic method [Marchalonic J J, Biochemical Journal (1969) 113:299-305; Thorell J I and Johansson B G, Biochimica et Biophysica Acta (1969) 251:363-9; the disclosure of each of which is hereby incorporated by reference in its entirety] and or by Chloramine-T/Iodogen/Iodobead methods [Hunter W M and Greenwood F C, Nature (1962) 194:495-6; Greenwood F C et al., Biochemical Journal (1963) 89:114-23; the disclosure of each of which is hereby incorporated by reference in its entirety].

Other uses of the disclosed receptors and methods will become apparent to those in the art based upon, inter alia, a review of this patent document.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below.

The following Examples are provided for illustrative purposes and not as a means of limitation. One of ordinary skill in the art would be able to design equivalent assays and methods based on the disclosure herein, all of which form part of the present invention.

A variety of expression vectors are available to those in the art for purposes of producing a polypeptide of interest in a cell. One suitable vector is pCMV, which is used in certain embodiments. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351. In some embodiments it is preferred that the vector utilized be an adenoviral expression vector. Exemplary adenoviral expression vectors include those that are commercially available from QBiogene (Carlsbad, Calif.) or that are described in U.S. Pat. No. 5,922,576.

Recombinant DNA techniques relating to the subject matter of the present invention and well known to those of ordinary skill in the art can be found, e.g, in Maniatis T et al., *Molecular Cloning: A Laboratory Manual* (1989) Cold Spring Harbor Laboratory, U.S. Pat. No. 6,399,373; and PCT Application Number PCT/IB02/01461 published as WO 02/066505 on 29 Aug. 2002; the disclosure of each of which is hereby incorporated by reference in its entirety.

Example 1

Full-Length Cloning of Endogenous Human RUP40

Polynucleotide encoding endogenous human RUP40 was cloned from Clontech Multiple Tissue cDNA Panel, catalog #K1425-1, specifically the human fetal spleen first-strand cDNA component.

The clone was generated by polymerase chain reaction using Advantage HF-2 polymerase (Clontech catalog #K1914-y) using the following gene-specific primers:

```
                                        (SEQ ID NO: 7;)
5'-ATATGGTACCATGAAATCCCCAAGGAGAACCACTTTGTGCC-3'
antisense (SEQ ID NO: 8;)
5'-ATATGCGGCCGCTTAGTTGAGCAACGAAGAAGCACTGGATGAG-3'
sense.
```

Anti-sense primer contains underlined Kpn1 restriction site, and bold/italicized start codon. Sense primer contains underlined NotI restriction site, and bold/italicized stop codon.

Advantage HF-2 Polymerase was used for the amplification in a 500 reaction by the following cycle, with steps 2 to 3 repeated 35 times: step 1: 94.0 C for 15 seconds; step 2: 94.0 C for 15 seconds; step 3: 68.0 C for 6.0 minutes; step 4: 68.0 C for 3.0 minutes. An approximately 4.1 kb PCR fragment was isolated from a 1% agarose gel and cloned into the per4-TOPO vector (Invitrogen) and completely sequenced using the ABI Big Dye Terminator Kit (P.E. Biosystems). See, SEQ ID NO:1 for nucleic acid sequence and SEQ ID NO:2 for deduced amino acid sequence.

It is within the purview of those of ordinary skill in the art to analogously clone polynucleotide encoding endogenous rat RUP40 using as template cDNA generated from, e.g., rat heart, lung or adipose tissue.

Example 2

Receptor Expression

Although a variety of cells are available to the art for the expression of proteins, it is most preferred that mammalian cells or melanophores be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells or melanophores. Of the mammalian cells, CHO, COS-7, 293 and 293T cells are particularly preferred, although the specific mammalian cell utilized can be predicated upon the particular needs of the artisan. In some embodiments, cardiomyocytes are preferred. See infra as relates to melanophores, including Example 8.

a. Transient Transfection

On day one, $6 \times 10^6$/10 cm dish of 293 cells well are plated out. On day two, two reaction tubes are prepared (the proportions to follow for each tube are per plate): tube A was prepared by mixing 4 µg DNA (e.g., pCMV vector; pCMV vector with receptor cDNA, etc.) in 0.5 ml serum free DMEM (Gibco BRL); tube B is prepared by mixing 24 µl lipofectamine (Gibco BRL) in 0.5 ml serum free DMEM. Tubes A and B are admixed by inversions (several times), followed by incubation at room temperature for 30-45 min. The admixture is referred to as the "transfection mixture". Plated 293 cells are washed with 1×PBS, followed by addition of 5 nil serum free DMEM. 1 ml of the transfection mixture is added to the cells, followed by incubation for 4 hrs at 37° C./5% $CO_2$. The transfection mixture is removed by aspiration, followed by the addition of 10 ml of DMEM/10% Fetal Bovine Serum. Cells are incubated at 37° C./5% $CO_2$. After 48 hr incubation, cells are harvested and utilized, for analysis.

b. Stable Cell Lines

Approximately $12 \times 10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 µg of DNA (e.g., pCMV vector with receptor cDNA). The 12 µg of DNA is combined with 60 µl of lipofectamine and 2 mL of DME High Glucose Medium without serum. The medium is aspirated from the plates and the cells are washed once with medium without serum. The DNA, lipofectamine, and medium mixture are added to the plate along with 10 mL of medium without serum. Following incubation at 37 degrees Celsius for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 µg/mL. The transfected cells now undergo selection for positively transfected cells containing the G418 resistance gene. The medium is replaced every four to five days as selection occurs. During selection, cells are grown to create stable pools, or split for stable clonal selection.

Example 3

Assays for Assessment of GPCR Activation

A variety of approaches are available for assessment of activation of mammalian GPCRs. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used in the direct identification method to screen candidate compounds to endogenous GPCRs and non-endogenous, constitutively activated GPCRs. The assay is generic and has application to drug discovery at all G protein-coupled receptors.

The [$^{35}$S]GTPγS assay is incubated in 20 mM HEPES and between 1 and about 20 mM $MgCl_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred) and 12.5 to 75 μg membrane protein (e.g 293 cells expressing the Gs Fusion Protein; this amount can be adjusted for optimization) and 10 μM GDP (this amount can be changed for optimization) for 1 hour. Wheatgerm agglutinin beads (25 μl; Amersham) are then added and the mixture incubated for another 30 minutes at room temperature. The tubes are then centrifuged at 1500×g for 5 minutes at room temperature and then counted in a scintillation counter.

2. Adenylyl Cyclase

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells are harvested approximately twenty four hours after transient transfection. Media is carefully aspirated off and discarded. 10 ml of PBS is gently added to each dish of cells followed by careful aspiration. 1 ml of Sigma cell dissociation buffer and 3 ml of PBS are added to each plate. Cells are pipetted off the plate and the cell suspension is collected into a 50 ml conical centrifuge tube. Cells are then centrifuged at room temperature at 1,100 rpm for 5 min. The cell pellet is carefully re-suspended into an appropriate volume of PBS (about 3 ml/plate). The cells are then counted using a hemocytometer and additional PBS was added to give the appropriate number of cells (with a final volume of about 50 μl/well).

cAMP standards and Detection Buffer {comprising 1 μCi of tracer [$^{125}$I]cAmp (50 μl) to 11 ml Detection Buffer} are prepared and maintained in accordance with the manufacturer's instructions. Assay Buffer is prepared fresh for screening and contained 50 μl of Stimulation Buffer, 3 ul of test compound (12 μM final assay concentration) and 50 μl cells. Assay Buffer is stored on ice until utilized. The assay is initiated by addition of sow of cAMP standards to appropriate wells followed by addition of 50 ul of PBSA to wells H11 and H12. 50 μl of Stimulation Buffer is added to all wells. DMSO (or selected candidate compounds) is added to appropriate wells using a pin tool capable of dispensing 3 μl of compound solution, with a final assay concentration of 12 μM test compound and 100 μl total assay volume. The cells are then added to the wells and incubated for 60 min at room temperature. 100 μl of Detection Mix containing tracer cAMP is then added to the wells. Plates are then incubated additional 2 hours followed by counting in a Wallac MicroBeta scintillation counter. Values of cAMP/well are then extrapolated from a standard cAMP curve which is contained within each assay plate.

3. Cell-Based cAMP for Gi Coupled Target GPCRs

TSHR is a Gs coupled GPCR that causes the accumulation of cAMP upon activation. TSHR will be constitutively activated by mutating amino acid residue 623 (i.e., changing an alanine residue to an isoleucine residue). A Gi coupled receptor is expected to inhibit adenylyl cyclase, and, therefore, decrease the level of cAMP production, which can make assessment of cAMP levels challenging. An effective technique for measuring the decrease in production of cAMP as an indication of constitutive activation of a Gi coupled receptor can be accomplished by co-transfecting, most preferably, non-endogenous, constitutively activated TSHR (TSHR-A623I) (or an endogenous, constitutively active Gs coupled receptor) as a "signal enhancer" with a Gi linked target GPCR to establish a baseline level of cAMP. Upon creating a non-endogenous version of the a coupled receptor, this non-endogenous version of the target GPCR is then co-transfected with the signal enhancer, and it is this material that can be used for screening. We will utilize such approach to effectively generate a signal when a cAMP assay is used; this approach is preferably used in the direct identification of candidate compounds against Gi coupled receptors. It is noted that for a Gi coupled GPCR, when this approach of signal enhancer is used in conjuction with either an endogenous or constitutively activated Gi coupled GPCR, an inverse agonist of the target GPCR will increase the cAMP signal and an agonist will decrease the cAMP signal.

On day one, $2 \times 10^4$ 293 cells/well will be plated out. On day two, two reaction tubes will be prepared (the proportions to follow for each tube are per plate): tube A will be prepared by mixing 2 μg DNA of each receptor transfected into the mammalian cells, for a total of 4 μg DNA (e.g., pCMV vector; pCMV vector with mutated THSR (TSHR-A623I); TSBR-A623I and GPCR, etc.) in 1.2 ml serum free DMEM (Irvine Scientific, Irvine, Calif.); tube B will be prepared by mixing 120 μl lipofectamine (Gibco BRL) in 1.2 ml serum free DMEM. Tubes A and B will then be admixed by inversions (several times), followed by incubation at room temperature for 30-45 min. The admixture is referred to as the "transfection mixture". Plated 293 cells will be washed with 1×PBS, followed by addition of 10 ml serum free DMEM. 2.4 ml of the transfection mixture will then be added to the cells, followed by incubation for 4 hrs at 37° C./5% $CO_2$. The transfection mixture will then be removed by aspiration, followed by the addition of 25 ml of DMEM/10% Fetal Bovine Serum. Cells will then be incubated at 37° C./5% $CO_2$. After 24 hr incubation, cells will then be harvested and utilized for analysis.

A Flash Plate™ Adenylyl Cyclase kit (New England Nuclear; Cat. No. SMP004A) is designed for cell-based assays, however, can be modified for use with crude plasma membranes depending on the need of the skilled artisan. The Flash Plate wells will contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells will be harvested approximately twenty four hours after transient transfection. Media will be carefully aspirated off and discarded. 10 ml of PBS will be gently added to each dish of cells followed by careful aspiration. 1 ml of Sigma cell dissociation buffer and 3 ml of PBS will be added to each plate. Cells will be pipetted off the plate and the cell suspension will be collected into a 50 ml conical centrifuge tube. Cells will then be centrifuged at room temperature at 1,100 rpm for 5 min. The cell pellet will be carefully re-suspended into an appropriate volume of PBS (about 3 ml/plate). The cells will then be counted using a hemocytometer and additional PBS is added to give the appropriate number of cells (with a final volume of about 50 µl/well).

cAMP standards and Detection Buffer {comprising 1 µCi of tracer [$^{125}$I]cAMP (50 µl) to 11 ml Detection Buffer} will be prepared and maintained in accordance with the manufacturer's instructions. Assay Buffer should be prepared fresh for screening and contain 50 µl of Stimulation Buffer, 3 µl of test compound (12 µM final assay concentration) and 50 µl cells. Assay Buffer can be stored on ice until utilized. The assay can be initiated by addition of 50 µl of cAMP standards to appropriate wells followed by addition of 50 µl of PBSA to wells H-11 and H12. Fifty µl of Stimulation Buffer will be added to all wells. Selected compounds (e.g., TSH) will be added to appropriate wells using a pin tool capable of dispensing 3 µl of compound solution, with a final assay concentration of 12 µM test compound and 100 µl total assay volume. The cells will then be added to the wells and incubated for 60 min at room temperature. 100 µl of Detection Mix containing tracer cAMP will then be added to the wells. Plates were then incubated additional 2 hours followed by counting in a Wallac MicroBeta scintillation counter. Values of cAMP/well will then be extrapolated from a standard cAMP curve which is contained within each assay plate.

4. Reporter-Based Assays a. CRE-Luc Reporter Assay LGs-Associated Receptors)

293 and 293T cells are plated-out on 96 well plates at a density of $2 \times 10^4$ cells per well and are transfected using Lipofectamine Reagent (BRL) the following day according to manufacturer's instructions. A DNA/lipid mixture is prepared for each 6-well transfection as follows: 260 ng of plasmid DNA in 100 µl of DMEM is gently mixed with 2 µl of lipid in 100 µl of DMEM {the 260 ng of plasmid DNA consists of 200 ng of a 8×CRE-Luc reporter plasmid, 50 ng of pCMV comprising endogenous receptor or non-endogenous receptor or pCMV alone, and 10 ng of a GPRS expression plasmid [GPRS in pcDNA3 (Invitrogen)]}. The 8×CRE-Luc reporter plasmid was prepared as follows: vector SRIF-β-gal was obtained by cloning the rat somatostatin promoter (−71/+51) at Bg1V-HindIII site in the pβgal-Basic Vector (Clontech). Eight (8) copies of cAMP response element were obtained by PCR from an adenovirus template AdpCF126CCRE8 [see, Suzuki et al., Hum Gene Ther (1996) 7:1883-1893; the disclosure of which is hereby incorporated by reference in its entirety] and cloned into the SRIF-β-gal vector at the Kpn-Bg1V site, resulting in the 8xCRE-β-gal reporter vector. The 8xCRE-Luc reporter plasmid was generated by replacing the beta-galactosidase gene in the 8xCRE-β-gal reporter vector with the luciferase gene obtained from the pGL3-basic vector (Promega) at the HindIII-BamHI site. Following 30 min incubation at room temperature, the DNA/lipid mixture is diluted with 400 µl of DMEM and 100 µl of the diluted mixture is added to each well. 100 µl of DMEM with 10% FCS is added to each well after a 4 hr incubation in a cell culture incubator. The following day the transfected cells are changed with 200 µl/well of DMEM with 10% FCS. Eight (8) hours later, the wells were changed to 100 µl/well of DMEM without phenol red, after one wash with PBS. Luciferase activity is measured the next day using the LucLite™ reporter gene assay kit (Packard) following manufacturer's instructions and read on a 1450 MicroBeta™ scintillation and luminescence counter (Wallac).

b. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue # 219073) can be utilized following the protocol set forth above with respect to the CREB reporter assay, except that the components of the calcium phosphate precipitate are 410 ng pAP1-Luc, 80 ng pCMV-receptor expression plasmid, and 20 ng CMV-SEAP.

c. SRF-Luc Reporter Assay (Gq-Associated Receptors)

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, e.g., COS7 cells. Cells are transfected with the plasmid components of the system and the indicated expression plasmid encoding endogenous or non-endogenous GPCR using a Mammalian Transfection Kit (Stratagene, Catalogue #200285) according to the manufacturer's instructions. Briefly, 410 ng SRF-Luc, 80 ng pCMV-receptor expression plasmid and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the manufacturer's instructions. Half of the precipitate is equally distributed over 3 wells in a 96-well plate, kept on the cells in a serum free media for 24 hours. The last 5 hours the cells are incubated with test compound or suitable control, where indicated. Cells are then lysed and assayed for luciferase activity using a Luclite™ Kit (Packard, Cat: # 6016911) and "Trilux 1450 Microbeta" liquid scintillation and luminescence counter (Wallac) as per the manufacturer's instructions. The data can be analyzed using GraphPad Prism™ 2.0a (GraphPad Software Inc.)

5. Intracellular IP3 Accumulation Assay (Gq-Associated Receptors)

On day 1, cells comprising the receptors (endogenous and/or non-endogenous) can be plated onto 24 well plates, usually $1 \times 10^5$ cells/well (although this number can be optimized. On day 2 cells can be transfected by firstly mixing 0.25 µg DNA in 50 µl serum free DMEM/well and 2 µl lipofectatnine in 50 µl serumfree DMEM/well. The solutions are gently mixed and incubated for 15-30 min at room temperature. Cells are washed with 0.5 ml PBS and 400 μl of serum free media is mixed with the transfection media and added to the cells. The cells are then incubated for 3-4 hrs at 37° C./5% $CO_2$ and then the transfection media is removed and replaced with 1 ml/well of regular growth media. On day 3 the cells are labeled with $^3$H-myo-inositol. Briefly, the media is removed and the cells are washed with 0.5 ml PBS. Then 0.5 ml inositol-free/serum free media (GIBCO BRL) is added/well with 0.25 μCi of $^3$H-myo-inositol/well and the cells are incubated for 16-18 hrs o/n at 37° C./5% $CO_2$. On Day 4 the cells are washed with 0.5 ml PBS and 0.45 ml of assay medium is added containing inositol-free/serum free media 10 μM pargyline 10 mM lithium chloride or 0.4 ml of assay medium and 50 μl of 10× ketanserin (ket) to final concentration of 10 μM. The cells are then incubated for 30 min at 37° C. The cells are then washed with 0.5 ml PBS and 200 μl of fresh/ice cold stop solution (1M KOH; 18 mM Na-borate; 3.8 mM EDTA) is added/well. The solution is kept on ice for 5-10 min or until cells are lysed and then neutralized by 200 μl of fresh/ice cold neutralization sol. (7.5 HCL). The lysate is then transferred into 1.5 ml eppendorf tubes and 1 ml of chloroform/methanol (1:2) is added/tube. The solution is vortexed for 15 sec and the upper phase is applied to a Biorad AG1-X8™ anion exchange resin (100-200 mesh). Firstly, the resin is washed with water at 1:1.25 W/V and 0.9 ml of upper phase is loaded onto the column. The column is washed with 10 mLs of 5 mM myo-inositol and 10 ml of 5 mM Na-borate/60 mM Na-formate. The inositol tris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd $H_2O$ and stored at 4° C. in water.

Example 4

Fusion Protein Preparation a. GPCR:Gs Fusion Constuct

The design of the constitutively activated GPCR-G protein fusion construct was accomplished as follows: both the 5' and 3' ends of the rat G protein Gsα (long form; Itoh, H. et al., 83 PNAS 3776 (1986)) were engineered to include a HindIII (5'-AAGCTT-3') sequence thereon. Following confirmation of the correct sequence (including the flanking sequences), the entire sequence was shuttled into pcDNA3.1(−) (Invitrogen, cat. no. V795-20) by subcloning using the HindIII restriction site of that vector. The correct orientation for the Gsα sequence was determined after subcloning into pcDNA3.1(−). The modified pcDNA3.1(−) containing the rat Gsα gene at HindIII sequence was then verified; this vector was now available as a "universal" Gsα protein vector. The pcDNA3.1(−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

b. Gq(6 Amino Acid Deletion)/Gi Fusion Construct

The design of a Gq(del)/Gi fusion construct can be accomplished as follows: the N-terminal six (6) amino acids (amino acids 2 through 7, having the sequence of TLESIM Gqα-subunit will be deleted and the C-terminal five (5) amino acids, having the sequence EYNLV will be replaced with the corresponding amino acids of the Giα Protein, having the sequence DCGLF. This fusion construct will be obtained by PCR using the following primers:

```
                                          (SEQ ID NO: 9)
5'-gatcAAGCTTCCATGGCGTGCTGCCTGAGCGAGGAG-3'  and (SEQ ID NO: 10)
5'-gatcGGATCCTTAGAACAGGCCGCAGTCCTTCAGGTTCAGCTGCAGG
ATGGTG-3'
``` and Plasmid 63313 which contains the mouse Gqα-wild type version with a hemagglutinin tag as template. Nucleotides in lower caps are included as spacers.

TaqPlus Precision DNA polymerase (Stratagene) will be utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product will be cloned into a pCRII-TOPO vector (Invitrogen) and sequenced using the ABI Big Dye Terminator kit (P.E. Biosystems). Inserts from a TOPO clone containing the sequence of the fusion construct will be shuttled into the expression vector pcDNA3.1(+) at the HindIII/BamHI site by a 2 step cloning process. Also see, PCT Application Number PCT/US02/05625 published as WO02068600 on 6 Sep. 2002, the disclosure of which is hereby incorporated by reference in its entirety.

Example 5

[$^{35}$S]GTPγS ASSAY

Membrane Preparation

In some embodiments membranes comprising the Target GPCR of interest and for use in the direct identification of candidate compounds as, e.g., inverse agonists, agonists, or antagonists, are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM $MgCl_2$, pH 7.4.

b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifuge at 20,000 rpm for 17 minutes at 4° C. The supernatant will then be aspirated and the pellet resuspended in Binding Buffer. This will then be homogenized using a Brinkman Polytron™ homogenizer (15-20 second bursts until the all material is in suspension). This is referred to herein as "Membrane Protein".

Bradford Protein Assay

Following the homogenization, protein concentration of the membranes will be determined using the Bradford Protein Assay (protein can be diluted to about 1.5 mg/nil, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5-10 seconds; it is noted that for multiple preparations, the homogenizer should be thoroughly cleaned between homogenization of different preparations).

a. Materials

Binding Buffer (as per above); Bradford Dye Reagent; Bradford Protein Standard will be utilized, following manufacturer instructions (Biorad, cat no. 500-0006).

b. Procedure

Duplicate tubes will be prepared, one including the membrane, and one as a control "blank". Each contained 800 μl Binding Buffer. Thereafter, 10 μl of Bradford Protein Standard (1 mg/ml) will be added to each tube, and 10 μl of membrane Protein will then be added to just one tube (not the blank). Thereafter, 200 μl of Bradford Dye Reagent will be added to each tube, followed by vortex of each. After five (5) minutes, the tubes will be re-vortexed and the material therein will be transferred to cuvettes. The cuvettes will then be read using a CECIL 3041 spectrophotometer, at wavelength 595.

Direct Identification Assay a. Materials

GDP Buffer consisted of 37.5 ml Binding Buffer and 2 mg GDP (Sigma, cat. no. G-7127), followed by a series of dilutions in Binding Buffer to obtain 0.2 μM GDP (final concentration of GDP in each well was 0.1 μM GDP); each well comprising a candidate compound, has a final volume of 2000 consisting of 100 μl GDP Buffer (final concentration, 0.1 μM GDP), 50 μl Membrane Protein in Binding Buffer, and 50 μl [$^{35}$S]GTPγS (0.6 nM) in Binding Buffer (2.5 [$^{35}$S]GTPγS per 10 ml Binding Buffer).

b. Procedure

Candidate compounds will be preferably screened using a 96-well plate format (these can be frozen at −80° C.). Membrane Protein (or membranes with expression vector excluding the Target GPCR, as control); will be homogenized briefly until in suspension. Protein concentration will then be determined using the Bradford Protein Assay set forth above. Membrane Protein (and control) will then be diluted to 0.25 mg/ml in Binding Buffer (final assay concentration, 12.5 μg/well). Thereafter, 100 μl GDP Buffer was added to each well of a Wallac Scintistrip™ (Wallac). A 5 ul pin-tool will then be used to transfer 5 μl of a candidate compound into such well (i.e., 5 μl in total assay volume of 200 μl is a 1:40 ratio such that the final screening concentration of the candidate compound is 10 μM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 μl of Membrane Protein will be added to each well (a control well comprising membranes without the Target GPCR was also utilized), and pre-incubated for 5-10 minutes at room temperature. Thereafter, 50 μl of [$^{35}$S]GTPγS (0.6 nM) in Binding Buffer will be added to each well, followed by incubation on a shaker for 60 minutes at room temperature (again, in this example, plates were covered with foil). The assay will then be stopped by spinning of the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer instructions).

Example 6

Cyclic AMP Assay

Another assay approach for directly identifying candidate compounds as, e.g., inverse agonists, agonists, or antagonists, is accomplished by utilizing a cyclase-based assay. In addition to direct identification, this assay approach can be utilized as an independent approach to provide confirmation of the results from the [$^{35}$S]GTPγS approach as set forth in Example 5, supra.

A modified Flash Plate™ Adenylyl Cyclase kit (New England Nuclear; Cat. No. SMP004A) is preferably utilized for direct identification of candidate compounds as inverse agonists and agonists to endogenous or non-endogenous, constitutively actived GPCRs in accordance with the following protocol.

Transfected cells are harvested approximately three days after transfection. Membranes were prepared by homogenization of suspended cells in buffer containing 20 mM HEPES, pH 7.4 and 10 mM MgCl$_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 10 mM MgCl$_2$, to yield a final protein concentration of 0.60 mg/ml (the resuspended membranes are placed on ice until use).

cAMP standards and Detection Buffer (comprising 2 μCi of tracer {[$^{125}$I]cAMP (100 μl) to 11 ml Detection Buffer] are prepared and maintained in accordance with the manufacturer's instructions. Assay Buffer is prepared fresh for screening and contained 20 mM HEPES, pH 7.4, 10 mM MgCl$_2$, 20 mM phosphocreatine (Sigma), 0.1 units/ml creatine phosphokinase (Sigma), 50 μM GTP (Sigma), and 0.2 mM ATP (Sigma); Assay Buffer was then stored on ice until utilized.

Candidate compounds are added, preferably, to 96-well plate wells (3 μl/well; 12 μM final assay concentration), together with 40 μl Membrane Protein (30 μg/well) and 50 μl of Assay Buffer. This admixture was then incubated for 30 minutes at room temperature, with gentle shaking.

Following the incubation, 100 μl of Detection Buffer is added to each well, followed by incubation for 2-24 hours. Plates are then counted in a Wallac MicroBeta™ plate reader using "Prot. #31" (as per manufacturer's instructions).

By way of example and not limitation, a representative screening assay plate (96 well format) result obtained is presented in FIG. 1. Each bar represents the result for a compound that differs in each well, the "Target GPCR" being a Gsα Fusion Protein construct of an endogenous, constitutively active Gs-coupled GPCR. The representative results presented in FIG. 1 also provide standard deviations based upon the mean results of each plate ("m") and the mean plus two arbitrary preference for selection of inverse agonists as "leads" from the primary screen involves selection of candidate compounds that that reduce the percent response by at least the mean plate response, minus two standard deviations. Conversely, an arbitrary preference for selection of agonists as "leads" from the primary screen involves selection of candidate compounds that increase the percent response by at least the mean plate response, plus the two standard deviations. Based upon these selection processes, the candidate compounds in the following wells were directly identified as putative inverse agonist (Compound A) and agonist (Compound B) to said endogenous GPCR in wells A2 and G9, respectively. See, FIG. 1. It is noted for clarity: these compounds have been directly identified without any knowledge of the endogenous ligand for this GPCR. By focusing on assay techniques that are based upon receptor function, and not compound binding affinity, we are able to ascertain compounds that are able to reduce the functional activity of this receptor (Compound A) as well as increase the functional activity of the receptor (Compound B).

Example 7

Fluorometric Imaging Plate Reader (FLIPR) Assay for the Measurement of Intracellular calcium concentration (Gq-Associated receptors)

Target GPCR (experimental) and pCMV (negative control) stably transfected cells from respective clonal lines are seeded into poly-D-lysine pretreated 96-well plates (Becton-Dickinson, #356640) at $5.5 \times 10^4$ cells/well with complete culture medium (DMEM with 10% FBS, 2 mM L-glutamine, 1 mM sodium pyruvate) for assay the next day. To prepare Fluo4-AM (Molecular Probe, #F14202) incubation buffer stock, 1 mg Fluo4-AM is dissolved in 467 µl DMSO and 467 µl Pluoronic acid (Molecular Probe, #P3000) to give a 1 mM stock solution that can be stored at $-20°$ C. for a month. Fluo4-AM is a fluorescent calcium indicator dye.

Candidate compounds are prepared in wash buffer (1×HBSS/2.5 mM Probenicid/20 mM HEPES at pH 7.4).

At the time of assay, culture medium is removed from the wells and the cells are loaded with 100 µl of 4 µM Fluo4-AM/2.5 mM Probenicid (Sigma, #P8761)/20 mM HEPES/complete medium at pH 7.4. Incubation at 37° C./5% $CO_2$ is allowed to proceed for 60 min.

After the 1 hr incubation, the Fluo4-AM incubation buffer is removed and the cells are washed 2× with 100 µl wash buffer. In each well is left 100 µl wash buffer. The plate is returned to the incubator at 37° C./5% $CO_2$ for 60 min.

FLIPR (Fluorometric Imaging Plate Reader; Molecular Device) is programmed to add 50 µl candidate compound on the $30^{th}$ second and to record transient changes in intracellular calcium concentration ([Ca2+]) evoked by the candidate compound for another 150 seconds. Total fluorescence change counts are used to determine agonist activity using the FLIPR software. The instrument software normalizes the fluorescent reading to give equivalent initial readings at zero.

In some embodiments, the cells comprising Target GPCR further comprise promiscuous G alpha 15/16 or the chimeric Gq/Gi alpha unit.

Although the foregoing provides a FLIPR assay for agonist activity using stably transfected cells, a person of ordinary skill in the art would readily be able to modify the assay in order to characterize antagonist activity. Said person of ordinary skill in the art would also readily appreciate that, alternatively, transiently transfected cells could be used.

Example 8

Melanophore Technology

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, against GPCRs. This method can be conducted by introducing test cells of a pigment cell line capable of dispersing or aggregating their pigment in response to a specific stimulus and expressing an exogenous clone coding for the CCPR. A stimulant, e.g., melatonin, sets an initial state of pigment disposition wherein the pigment is aggregated within the test cells if activation of the GPCR induces pigment dispersion. However, stimulating the cell with a stimulant to set an initial state of pigment disposition wherein the pigment is dispersed if activation of the GPCR induces pigment aggregation. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and methods will be followed according to the disclosure of U.S. Pat. No. 5,462,856 and U.S. Pat. No. 6,051,386. These patent disclosures are hereby incorporated by reference in their entirety.

The cells are plated in 96-well plates (one receptor per plate). 48 hours post-transfection, half of the cells on each plate are treated with 10 nM melatonin. Melatonin activates an endogenous Gi-coupled receptor in the melanophores and causes them to aggregate their pigment. The remaining half of the cells are transferred to serum-free medium 0.7×L-15 (Gibco). After one hour, the cells in serum-free media remain in a pigment-dispersed state while the melatonin-treated cells are in a pigment-aggregated state. At this point, the cells are treated with a dose response of a test compound. If the plated GPCRs bound to the test compound, the melanophores would be expected to undergo a color change in response to the compound. If the receptor were either a Gs or Gq coupled receptor, then the melatonin-aggregated melanophores would undergo pigment dispersion. In contrast, if the receptor was a Gi-coupled receptor, then the pigment-dispersed cells would be expected to undergo a dose-dependent pigment aggregation.

Example 9

MAP Kinase Assay

MAP kinase (mitogen activated kinase) may be monitored to evaluate receptor activation. MAP kinase can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilin. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman. P81 chromatography paper, which retains the phosphorylated protein. The chromatography paper is washed and counted for $^{32}$P is a liquid scintillation counter. Alternatively, the cell extract is incubated with gamma-$^{32}$P-ATP, an ATP regenerating system, and biotinylated myelin basic proein bound by streptavidin to a filter support. The myelin basic protein is a substrate for activated MAP kinase. The phosphorylation reaction is carried out for 10 min at 30° C. The extract can then be aspirated through the filter, which retains, the phosphorylated myelin basic protein. The filter is washed and counted for $^{32}$P by liquid scintillation counting.

Example 10

MAPK/ERK Kinase Kinase-1 (MEKK1) Assay

In vitro kinase activity of MEKK1 is measured as described by Minamino et al. [Proc Natl Acad Sci USA (2002) 99:3866-3871; the disclosure of which is hereby incorporated by reference in its entirety]. Briefly, cell lysates (400 µg) are immunoprecipated with primary antibody to MEKK1 (2 µg) (Catalog #sc-252, Santa Cruz Biotechnology, Santa Cruz, Calif.) for 4 h, followed by incubation with Protein G-Sepharose (50% wt/vol, Amersham Pharmacia) for 2 h at 4° C. GST-SEK1 (Upstate Biotechnology, Lake Placid, N.Y.) is used as substrate. Samples are resolved by SDS/PAGE, and phosphorylated substrates are detected and quantified by using a PhosphorImager (Molecular Probes).

Example 11

Tissue Distribution of Human RUP40

A. Affymetrix GeneChip® Technology

Nucleotide sequences were submitted to Affymetrix for the designing and manufacturing of microarray containing oligonucleotides to monitor the expression levels of G protein-coupled receptors (GPCRs) using their GeneChip® Technology. Also present on the microarray were probes for characterized human brain tissues from Harvard Brain Bank or obtained from commercially available sources. RNA samples were amplified, labeled, hybridized to the microarray, and data analyzed according to manufacturer's instructions.

Figure 2:
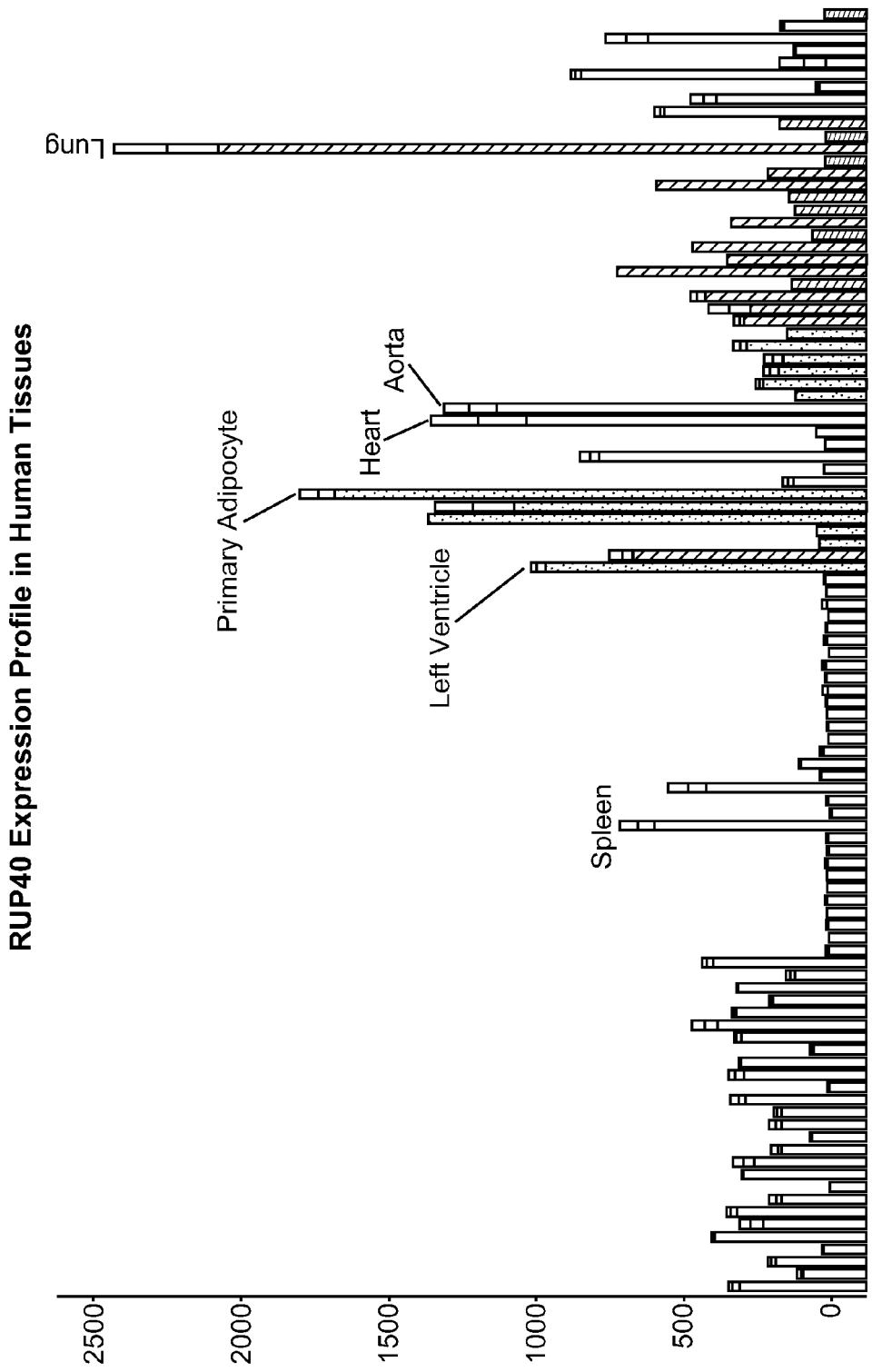
FIG. 2. Microarray analysis was performed on human tissue samples using a custom high-density oligonucleotide microarray, which contains probes that monitor the expression of RUP40. The histogram plot provides the relative expression levels (Average Difference) and standard errors of duplicate measurements of RUP40 for each of the tissues profiled. Relative expression level is indicated on the vertical axis. Tissue identity is displayed on the horizontal axis and is (from left to right): Sciatic Nerve; Dorsal Root Ganglion; Corpus Callosum; Neural progenitor, Globus pallidus; Cingulate gyrus; Hypothalamus, anterior; Pituitary gland, female; Astrocytes, activated; Pituitary gland, male; Caudate Putamen; Ventral Tegmental Area (VTA); Fetal Brain; Cerebellum; Olfactory bulb; Amygdala; Astrocytes, resting, Hippocampus; Whole brain; Medulla Oblongata; Anterior Hippocampus; Substantia Nigra; Frontal Cortex, Superior BM9; Spinal Cord; Thalamus; Pons, lower; Pons, upper; HL-60+DMSO; THP-1 activated; HL-60; Jurkat; U87; MCF7; SHSH5Y; monocytes, adherent; THP-1; SHSH5Y+BDNF; Spleen; Natural Killer Cells; myeloid progenitors, bone marrow; Lymph Node; Neutrophils; Thymus; CD34+progenitor cells; T-cells, CD8+ resting; T-cells, CD4+ resting; T-cells, CD8+ activated; AC133+; B-cells, CD19+; Bone Marrow; myeloid progenitors, mobilized peripheral blood; T-cells, CD4+ activated; erythroid progenitors; monocytes, CD14$^+$; CD34+, mobilized peripheral blood; CD34+, cord blood; eosinophils; dendritic precursors; Ventricle, Left; cartilage; Preadipocyte, cultured; Adipocyte, cultured; Adipocyte, primary; Adipose; visceral fat; HUVEC; Aortic Smooth Muscle Cells, proliferative; Pericardium; Aortic Smooth Muscle Cells, contractile; Aortic Endothelial Cells; Heart; Aorta; Stomach; Rectum; Colon; Small Intestine; Liver; Fetal Liver; Esophagus; Skeletal Muscle; Skin; Pancreas; Kidney; Bladder; Adrenal Gland; Salivary Gland; gall bladder; smooth muscle; Trachea; Bone; pancreatic islets; Mesenchymal stem cell; Lung; melanocytes; duodenum; Placenta; Ovary; Testis; Breast; Prostate epithelial; Cervix; Uterus; Prostate.

Using the GeneChip, the expression profile of human RUP40 was interrogated. See FIG. 2. FIG. 2 is a plot representing the expression level of human RUP40 in various tissues. It is evident that human RUP40 is highly expressed in heart, lung, aorta, and adipose. Human RUP40 is expressed at lower level in spleen. Within heart, RUP40 is highly expressed by left ventricle. Selective expression of RUP40 is also seen in heart, lung and adipose in the mouse (not shown).

Example 12

Immunostaining of RUP40 In Rat Heart

Affinity-purified polyclonal rabbit antibody directed against rat RUP40 was prepared using the peptide NTGG-WDSSGCTVEDDGRDNRDR, corresponding to amino acids 964-985 of SEQ ID NO:4 (SynPep, Dublin, Calif.). Isolated heart tissue from an anesthetized adult female Sprague-Dawley rat was embedded in paraffin for sectioning. Serial 6 micron transverse sections through the left ventricle were prepared and peroxidase-based immunohistochemistry carried out using standard techniques. Immunoglobulin from non-immunized rabbits (Catalog #N1699, DakoCytomation, Carpinteria, Calif.) was used as the negative control. Cardiac myocytes showed diffuse staining throughout the cytosol with more intense staining at the plasma cell membrane (FIG. 3).

Example 13

Expression of RUP40 by Neonatal Rat Ventricular Myocytes (NRVMs)

Primary Cell Culture

Neonatal rat ventricular myocytes (NRVMs) were isolated and cultured as described previously [Adams, J W et al., J Biol Chem (1996) 271:1179-86]. Briefly, hearts were obtained from 1- to 2-day old Sprague-Dawley rat pups and digested with collagenase, and myocytes were purified by passage through a Percoll gradient. Cells were plated onto tissue culture dishes precoated with 1% gelatin and maintained overnight in 4:1 DMEM/medium-199 supplemented with 10% horse serum, 5% fetal calf serum, and antibiotics (100 units/ml penicillin and 100 µg/ml streptomycin. After 18 hours in plating medium, myocytes were washed with maintenance medium (DMEM/medium 199 plus antibiotics) to remove dead cells and debris and refreshed with maintenance medium for the duration of the experiment.

RT-PCR

Total RNA isolated from NRVMs and fibroblasts as described above was used as a template for generation of reverse transcribed DNA (RT-DNA) using the RT for PCR kit (Becton Dickinson, Franldin, N.J.) according to manufacturer's instructions. RUP40 expression was detected in RT-DNA samples by PCR. PCR conditions were: 96° C. or 2 min; 30 cycles of 96° C. for 30 sec, 55° C. for 30 sec, 72° C. for 2 min; 72° C. for 10 min.

The rat RUP40 forward primer used has the sequence:
5'-GCCTGTCTAGTTGTGGAAGC-3' (SEQ ID NO:11).
The rat RUP40 reverse primer used has the sequence:
5'-GGTGTCCTCCCAGTTGAGCCAACA-3' (SEQ ID NO:12).
The amplified rat RUP40 DNA product is of size 403 base pairs. G3PDH amplifiers (Becton Dickinson, Franldin, N.J.) were added to each PCR reaction as an internal control.

Results

RUP40 was found to be expressed in cardiomyocytes. Results are presented in FIG. 4. RT-PCR demonstrates expression of RUP40 transcript in neonatal ventricular myocytes (NRVMs) maintained under serum-free (SFM) conditions for 24 hours. RUP40 transcript levels in the myocytes drop dramatically 24 hours following addition of phorbol 12-myristate 13-acetate (PMA) but remain elevated following addition of phenylephrine (PE) or prostaglandin F2 alpha (PG) to media. Note nearly undetectable levels of RUP40 expression in primary ventricular fibroblasts (Fibro). G3PDH PCR product demonstrates equal levels of template used for the PCR reaction and consistency of gel loading. Amplification was template-dependent, as indicated by the "-" lane of the gel corresponding to amplification in the absence of template. Expression of RUP40 by rat ventricular myocytes is consistent with the expression profile of human and mouse (not shown) RUP40 determined in Example 11 and displayed in FIG. 2.

Example 14

Overexpression of RUP40 in Cardiomyocytes Results in Increased IP3 Accumulation

Primary Cell Culture

Neonatal rat ventricular myocytes (NRVMs) were isolated and cultured as described previously [Adams, J W et al., J Biol Chem (1996) 271:1179-86; the disclosure of which is hereby incorporated by reference in its entirety]. Briefly, hearts were obtained from 1- to 2-day old Sprague-Dawley rat pups and digested with collagenase, and myocytes were purified by passage through a Percoll gradient. Cells were plated onto 24 well gelatin coated plates at $0.2 \times 10^6$ cells/well and maintained overnight in 4:1 DMEM/medium-199 supplemented with 10% horse serum, 5% fetal calf serum, and antibiotics (100 units/ml penicillin and 100 µg/ml streptomycin. After 18 hours in plating medium, myocytes were washed with maintenance medium (DMEM/medium 199 plus antibiotics) to remove dead cells and debris and refreshed with maintenance medium for the duration of the experiment.

RUP40 Adenovirus Vector Contruction

For adenovirus experiments, polynucleotide of SEQ ID NO:1 encoding human RUP40 polypeptide of SEQ ID NO:2 was subcloned into pShuttleCMV (Qbiogene, Carlsbad, Calif.) prior to generation of recombinant adenoviral RUP40 (AdRUP40) by homologous recombination in HEK 293 cells.

Adenovirus Infections

After the plating period, myocytes were switched to maintenance medium as described above and immediately infected with the recombinant adenorvirus or mock infected. Infection of NRVMs with adenovirus vectors was carried out as previously described [Adams, J W et al., Circ Res (2000) 87:1180-7]. Optimal multiplicity of infection (M01) was determined to be 20-50 plaque forming units (PFU) per cell over a dose range of 0.1-500 PFU/cell. A MOI of 20 PFU/cell resulted in greater than 95% infection efficiency [as determined by Green Fluoiescent Protein (GFP) expression in NRVMs infected with this control virus] without any cytotoxicity during the first 48 h following infection with the control adenovirus encoding GPF (AdGFP).

IP3 Assay

Adenovirus infected myocytes were incubated in maintenance medium containing 2 µCi/ml [$^3$H]myoinositol for 18-24 hours prior to addition of assay medium containing 10 mM LiCl in 20 mM HEPES-buffered medium. After 30 minutes in assay buffer, cells were cold acid fixed (0.1 M formic acid) and lysates were transferred to columns containing Dowex 100-200 mesh (formate form) resin beads. Inositol phosphates were eluted with 1M ammonium formate and 0.1 M formic acid and quantified by liquid scintillation counting.

Results

Overexpression of RUP40 in cardiomyocytes stimulated increased IP3 accumulation, as determined by Anova/Bonferroni ad hoc statistical analysis. The overexpressed RUP40 therefore manifested a level of constitutive Gq coupling activity under the conditions of the assay. Results are presented in FIG. 5.

Example 15

Overexpression of RUP40 Stimulates Hypertrophy and Atrial Natriuretic Factor (ANF) Expression in Cardiomyocytes Primary Cell Culture Neonatal rat ventricular myocytes (NRVMs) were prepared as described previously [Adams, J W et al., J Biol Chem (1996) 271:1179-86] and as described in Example 14.

RUP40 Adenovirus Vector Contruction

Adenovirus Infections

RUP40 adenovirus vector contraction and adenovirus infections were carried out as described in Example 11.

Results: Hypertrophy

Overexpression of RUP40 stimulated hypertrophy in cardiomyocytes. Results are presented in FIG. 6A. NRMVs infected with AdRUP40 at 20 plaque forming units (PFU) per cell for 48 hours demonstrated increased cell size compared to control cells infected with AdGFP control virus.

Results: Atrial Natriuretic Factor (ANF) Expression

Overexpression of RUP40 stimulated expression of atrial natriuretic factor (ANF) in cardiomyocytes. Results are presented in FIG. 6B, which shows the level of expression of endogenous ANF transcript and the level of expression of recombinant human RUP40 transcript. NRVMs were treated with recombinant adenovirus encoding human RUP40 or a control adenovirus (AdGFP) at a multiplicity of infection of 20 PFU/cell. 24 hours following adenovirus infection, total RNA was isolated and Northern blot analysis carried out to determine levels of virally expressed RUP40. Rat RUP40 cDNA fragment consisting of nucleotides 2,858-3,606 was used as probe. The same membrane was probed for atrial natriuretic factor (ANF) expression, a genetic marker of cardiomyocyte hypertrophy [Rodman et al., Proc Natl Acad Sci USA (1991) 88:8277-81]. Probes were labeled with [$^{32}$P] by random priming. In addition, the membrane was stained with methylene blue to confirm equal loading and transfer of RNA.

Example 16

Myocardial Expression of RUP40 Under Conditions of Pressure Overload Resulting from Transverse Aortic Constriction (TAC)

Transverse Aortic Constriction (TAC)

Surgical constriction of the transverse aorta in mice was performed as previously described [Rockman, H A et al., Proc Natl Acad Sci USA (1991) 88:8277-81]. Briefly, 8 week old mice (C57/BL6) were anesthetized with a mixture of ketamine and xylazine. Under a dissecting microscope a midline cervical incision was made to expose the trachea and carotid arteries by microsurgical techniques. After successful endotracheal intubation, the cannula was connected to a volume cycled rodent ventilator (Harvard Apparatus) on supplemental oxygen with a tidal volume of 0.2 ml and respiratory rate of 110 per min. The chest cavity was entered in the second intercostal space at the left upper sternal border through a small incision, and aortic constriction was performed by tying a 7-0 nylon suture ligature against a 27-gauge needle to yield a narrowing 0.4 mm in diameter when the needle was removed and a reproducible transverse aortic constriction (TAC) of 65-70%. Following aortic banding the pneumothorax was evacuated and the animals were extubated and allowed to recover. Control sham-operated mice undergo surgery but are not subjected to transverse aortic constriction (TAC). Seven days following surgery, surviving animals were euthanized and hearts were fixed with formalin by retrograde perfusion.

The fixed heart tissue was embedded in a 50:50 mixture of OCT:Aqua Mount (VWR, #41799-008, West Chester, Pa.) and frozen in dry ice/ethanol. The blocks were kept at −80° C. until cryosectioning was. After cryosectioning, the tissue sections were stored at −20° C. in sealed slide boxes.

In Situ Hybridization

Mouse RUP40 polynucleotide of SEQ ID NO:5 was subcloned into PCR11—TOPO vector (Invitrogen, Carlsbad, Calif.) at a site flanked by SP6 and T7 promoters. [$^{35}$S]-radiolabeled antisense mouse RUP40 mRNA probe complementary to the polynucleotide of SEQ ID NO:5 was prepared using SP6 RNA polymerase from Promega RiboProbe Transcription Kit (#P1460; Madison, Wis.), essentially as per the manufacturer's instructions. Control radiolabeled sense probe was prepared analogously using T7 RNA polymerase.

Fixed tissue sections were thawed and immediately subjected to a series of post-fix incubations at room temperature: PBS for 3 min; 10% formalin for 10 min; PBS for 10 min; and PBS for 10 min.

The tissue sections were then subjected to permeabilization and acetylation. To this end, the tissue sections were incubated with Proteinase K (0.001% Proteinase K in 0.5M Tris, 0.25M EDTA, pH 8.0) for 10 min at 37° C., followed by a wash with water for 5 min at room temperature. The tissue sections were then incubated for 5 min at room temperature with triethanolamine buffer (0.1M TEA, pH 8.0), followed by incubation for 5 min at room temperature with 2.5% acetic anhydride in 0.1M TEA pH 8.0. The tissue sections were then incubated at room temperature for 2 min each with: 2×SSC; 50% ethanol; 95% ethanol; and 100% ethanol. The tissue sections were then air dried and kept under desiccation until hybridization the following day.

Hybridization of the tissue sections was carried out for 20 hours at 60° C. in 0.47M NaCl, 54% formamide in a volume of 80-100 µl per section. Radiolabled probe was used at 1×10$^{7}$ cpm/ml. The tissue sections were then washed four times with 4×SSC at room temperature for 10 min each time. Unhybridized probe was digested on incubation with RNase A (20 µg/ml in 0.5M NaCl, 10 mM Tris, 1 mM EDTA, pH 8.0) for 30 min at 37° C. The tissue sections were then washed two times with 2×SSC at room temperature for 5 min each time, followed by a wash with 1x SSC at room temperature for 10 min, followed by a wash with 0.5×SSC at room temperature for 10 min. The tissue sections were then washed with 0.1× SSC at 65° C. for 30 min, followed by a wash with 0.1×SSC at room temperature for 5 min, followed by dehydration in alcohol.

Tissue sections which had undergone hybridization were then exposed to X-ray film and the RUP40 hybridization signal visualized by autoradiography. To this end, the tissue sections were exposed to Biomax MR film for 1 day, 4 days, and then 1 week After autoradiography, the tissue sections were emulsion dipped using NTB-2 liquid emulsion (VWR, #IB1654433, West Chester, Pa.). The emulsion dipped tissue sections were exposed to the emulsion for 1 week and then developed. After development, the tissue sections were counterstained with bisbenzimide (0.001% in PBS) and coverslipped. The tissue sections were photographed using a darkfield condenser (silver grains appear white) and DAPI filter cube (to observe fluorescent bisbenzimide counterstain).

Results

Under conditions of pressure overload resulting from transverse aortic constriction (TAC), hypertrophy levels of RUP40 mRNA were maintained or increased slightly. Results are presented in FIG. 7. In situ hybridization demonstrated broad myocardial expression in adult mouse heart. Antisense RUP40 radiolabeled riboprobe detected RUP40 expression in all chambers of the heart. Sense control riboprobe was used on additional sections from the control sham-operated mice as a negative control to demonstrate signal to noise ratio of probe labeling of heart sections.

Example 17

In Vivo Animal Model of Hypertrophic Cardiomyopathy

A compound of the present invention can be shown to have efficacy for the prevention of or treatment for a hypertrophic cardiomyopathy using the in vivo animal model of Rockman et al. [Proc Natl Acad Sci USA (1991) 88:8277-81; the disclosure of which is hereby incorporated by reference in its entirety], intended to be illustrative and not limiting, wherein mice are subjected to conditions of pressure overload resulting from transverse aortic constriction (TAC). In some embodiments, said compound is an inverse agonist or antagonist Said compound is administered by intraperitoneal injection. Preferred dose is 0.1-100 mg/kg. Other preferred dose is selected from the group consisting of: 0.1 mg/kg, 0.3 mg/kg; 1.0 mg/kg; 3.0 mg/kg; 10 mg/kg; 30 mg/kg and 100 mg/kg. The placebo group is administered vehicle alone.

Surgical constriction of the transverse aorta in mice is performed as previously described [Rockman, HA et al., Proc Natl Acad Sci USA (1991) 88:8277-81]. Briefly, 8 week old mice (C57/BL6) are anesthetized with a mixture of ketamine and xylazine. Under a dissecting microscope a midline cervical incision is made to expose the trachea and carotid arteries by microsurgical techniques. After successful endotracheal intubation, the cannula is connected to a volume cycled rodent ventilator (Harvard Apparatus) on supplemental oxygen with a tidal volume of 0.2 ml and respiratory rate of 110 per min. The chest cavity is entered in the second intercostal space at the left upper sternal border through a small incision, and aortic constriction is performed by tying a 7-0 nylon suture ligature against a 27-gauge needle to yield a narrowing 0.4 mm in diameter when the needle is removed and a reproducible transverse aortic constriction (TAC) of 65-70%. Following aortic banding the pneumothorax is evacuated and the animals are extubated and allowed to recover. Control sham-operated mice undergo surgery but are not subjected to transverse aortic constriction (TAC). A dose of the test compound or vehicle alone is administered daily by intraperitoneal injection. Seven days following surgery, surviving animals are euthanized and several parameters of hypertrophic cardiomyopathy assessed [Rockman, H A et al., Proc Natl Acad Sci USA (1991) 88:8277-81].

Wet and dry heart weight are assessed. Wet and dry heart weight/body weight ratio are assessed. The cross-sectional area of myocytes (mean cell area at the nucleus) is assessed. The induction of the atrial natriuretic factor (ANF) gene at the level of mRNA is assessed. Reduction of wet or dry heart weight, reduction of the wet or dry heart weight/body weight ratio, reduction of the cross-sectional area of myocytes, or reduction of the level of induction of ANF gene on administration of the compound is taken as indicative of the compound having utility for the prevention of or treatment for hypertrophic cardiomyopathy.

Example 18

Oral Bioavailability

Physicochemico analytical approaches for directly assessing oral bioavailability are well known to those of ordinary skill in the art and may be used [see, e.g., without limitation: Wong P C et al., Cardiovasc Drug Rev (2002) 20:137-52; and Buchan P et al., Headache (2002) Suppl 2:S54-62; the disclosure of each of which is hereby incorporated by reference in its entirety]. By way of further illustration and not limitation, said alternative analytical approaches may comprise liquid chromatography-tandem mass spectrometry [Chavez-Eng C M et al., J Chromatogr B Analyt Technol Biomed Life Sci (2002) 767:117-29; Jetter A et al., Clin Pharmacol Ther (2002) 71:21-9; Zimmerman J J et al., J Clin Pharmacol (1999) 39:1155-61; and Barrish A et al., Rapid Commun Mass Spectrom (1996) 10:1033-7; the disclosure of each of which is hereby incorporated by reference in its entirety].

Positron emission tomography (PET) has been successfully used to obtain direct measurements of drug distribution, including oral bioavailability, in the mammalian body following oral administration of the drug [Gulyas et al., Eur J Nucl Med Mol Imaging (2002) 29:1031-8; the disclosure of which is hereby incorporated by reference in its entirety].

Alternatively, oral bioavailability of a modulator of the invention may be determined on the basis of in vivo data developed, as for example by way of illustration and not limitation through the mouse model of Example 17. The modulator is administered by oral gavage at doses ranging from 0.1 mg le to 100 mg kg$^{-1}$. Oral administration of the modulator is shown to have utility for the prevention of or treatment for hypertrophic cardiomyopathy. The effect of the modulator is shown to be dose-dependent and comparable to the effect after intraperitoneal administration. The dose of modulator required to achieve half-maximal reduction of wet or dry heart weight, the wet or dry heart weight/body weight ratio, the cross-sectional area of myocytes, or the level of induction of ANF gene through oral administration is compared to the dose of modulator required to achieve half-maximal reduction of wet or dry heart weight, the wet or dry heart weight/body weight ratio, the cross-sectional area of myocytes, or the level of induction of ANF gene through intraperitoneal administration. By way of illustration, if said oral dose is twice said intraperitoneal dose, then the oral bioavailabilty of the modulator is taken to be 50%. More generally, if said oral dose is 8 mg kg$^{-1}$ and said intraperitoneal dose is p mg kg', then the oral bioavailability of the modulator as a percentage is taken to be [(ρ/θ)×100]. In some embodiments, the modulator is an inverse agonist or antagonist.

It would be readily apparent to anyone of ordinary skill in the art that a determination of oral bioavailability of a modulator of the invention can be carried out using an in vivo animal model other than the one presented here for purposes of illustration and not limitation. It is readily envisioned that the reference route of administration may be other than intraperitoneal. In some embodiments, said reference route of administration may be intravenous.

Example 19

Transgenic Mouse/Rat/Pig Comprising Expression of a Human RUP40 GPCR

The present invention also provides methods and compositions relating to a transgenic non-human mammal comprising expression of a human RUP40 GPCR, said receptor comprising an amino acid sequence selected from the group consisting of:
(a) amino acids 1-1,346 of SEQ ID NO:2;
(b) amino acids 1-990 of SEQ ID NO:2;
(c) amino acids 991-1,346 of SEQ ID NO:2; and
(d) amino acids 954-997 of SEQ ID NO:2;
or a biologically active fragment of the amino acid sequence of SEQ ID NO:2; or a constitutively activated mutant of the amino acid sequence of SEQ ID NO:2 or said biologically active fragment thereof. In some embodiments, said non-human mammal is a mouse, rat, or pig.

Methods of making transgenic animals such as mice, rats, and pigs are well known to those of ordinary skill in the art, and any such method can be used in the present invention. Briefly, transgenic mammals can be produced, e.g., by transfecting a pluripotential stem cell such as an ES cell with a polynucleotide ("transgene") encoding a human RUP40 GPCR. Successfully transformed ES cells can then be introduced into an early stage embryo that is then implanted into the uterus of a mammal of the same species. In certain cases, the transformed ("transgenic") cells will comprise part of the germ line of the resulting animal and adult animals comprising the transgenic cells in the germ line can then be mated to other animals, thereby eventually producing a population of transgenic animals that have the transgene in each of their cells and that can stably transmit the transgene to each of their offspring. Other methods of introducing the polynucleotide can be used, for example introducing the polynucleotide encoding a human RUP40 GPCR into a fertilized egg or early stage embryo via microinjection. Alternatively, the transgene may be introduced into an animal by infection of zygotes with a retrovirus containing the transgene [Jaenisch, R, Proc Natl Acad Sci USA (1976) 73:1260-4]. Methods of making transgenic mammals are described, e.g., in Wall et al., J Cell Biochem (1992) 49:113-20; Hogan et al., in Manipulating the Mouse Embryo. A Laboratory Manual. (1986) Cold Spring Harbor Laboratory Press, Cold Spring Harbor, N.Y.; in Costa et al., FASEB J (1999) 13:1762-73; in WO 91/08216; in U.S. Pat. No. 4,736,866; and in U.S. Pat. No. 6,504,080; the disclosure of each of which is hereby incorporated by reference in its entirety.

In some embodiments, said expression of a human RUP40 GPCR is cardiomyocyte-selective. In some embodiments, said cardiomyocyte-selective expression of said human RUP40 GPCR is conferred by alpha myosin heavy chain promoter [Subramaniam A et al., J Biol Chem (1991) 266: 24613-20; the disclosure of which is hereby incorporated by reference in its entirety].

Example 20

Transgenic In Vivo Animal Model of Hypertrophic Cardiomyopathy

A compound of the present invention can be shown to have efficacy for the prevention of or treatment for a cardiovascular disorder using a transgenic in vivo animal model described in Example 19, wherein said transgenic animal exhibits predisposition to or manifest hypertrophic cardiomyopathy relative to wild-type control animal. Said cardiovascular disorder encompasses heart disease, more particularly hypertrophic cardiomyopathy and congestive heart failure. Said transgenic animal exhibits said predisposition to or manifest hypertrophic cardiomyopathy if at any age said animal displays increased wet or dry heart weight, increased wet or dry heart weight/body weight ratio, increased cross-sectional area of myocytes, or increased level of induction of ANF gene relative to age-matched wild-type control animal. In some embodiments, said animal is mouse.

Said compound can be assessed for efficacy for the prevention of said cardiovascular disorder by administering said compound to said transgenic animal prior to onset of the hypertrophic cardiomyopathy phenotype and determining if said administration prevents said hypertrophic cardiomyopathy phenotype exhibited by said transgenic animal administered vehicle alone. Said compound can be shown to have efficacy for the prevention of said cardiovascular disorder if administration of said compound prevents the increased wet or dry heart weight, increased wet or dry heart weight/body weight ratio, increased cross-sectional area of myocytes, or increased level of induction of ANF gene exhibited by said transgenic animal administered vehicle alone.

Said compound can be assessed for efficacy for the treatment for said cardiovascular disorder by administering said compound to said transgenic animal after the onset of the hypertrophic cardiomyopathy phenotype and determining if said administration inhibits or ameliorates the hypertrophic cardiomyopathy. Said compound can be shown to have efficacy for the inhibition or amelioration of said cardiovascular disorder if administration of said compound inhibits or ameliorates the increased wet or dry heart weight, increased wet or dry heart weight/body weight ratio, increased cross-sectional area of myocytes, or increased level of induction of ANF gene exhibited by said transgenic animal administered vehicle alone.

In some embodiments, said compound is an inverse agonist or antagonist. In some embodiments, said compound is administered by intraperitoneal injection. Preferred dose is 0.1-100 mg/kg. Other preferred dose is selected from the group consisting of: 0.1 mg/kg, 0.3 mg/kg; 1.0 mg/kg; 3.0 mg/kg; 10 mg/kg; 30 mg/kg and 100 mg/kg. The placebo group is administered vehicle alone. In some embodiments, said dose is administered daily. In some embodiments, said dose is administered for a period selected from the group of one week, two weeks, three weeks, and four weeks. It is noted that this route of administration, these dosage ranges, this frequence of dose administiation, and this duration of dose administration are intended to be illustrative and not limiting to the invention.

Example 21

Transgenic Mouse/Rat/Pig Comprising a Disruption in a RUP40 Gene

Mouse

A preferred DNA construct will comprise, from 5'-end to 3'-end: (a) a first nucleotide sequence that is comprised in the mouse RUP40 genomic sequence; (b) a nucleotide sequence comprising a positive selection marker, such as the marker for neomycin resistance (neo); and (c) a second nucleotide sequence that is comprised in the mouse RUP40 genomic sequence and is located on the genome downstream of the first mouse RUP40 nucleotide sequence (a). Mouse RUP40 genomic sequence will be isolated using methods well known to those of ordinary skill in the art (Maniatis T et al., *Molecular Cloning: A Laboratory Manual* (1989) Cold Spring Harbor Laboratory; the disclosure of which is hereby incorporated by reference in its entirety). Probes for said isolation of mouse RUP40 genomic sequence will be derived from cDNA encoding a mouse RUP40 polypeptide, wherein said cDNA may be obtained using as template mRNA from mouse heart, lung, or adipose tissue.

In preferred embodiments, this DNA construct also comprises a negative selection marker located upstream the nucleotide sequence (a) or downstream the nucleotide sequence (c). Preferably, the negative selection marker comprises the thymidine kinase (tk) gene [Thomas et al., Cell (1986) 44:419-28], the hygromycin beta gene [Te Riele et al., Nature (1990) 348:649-51], the hprt gene [Van der Lugt et al., Gene (1991) 105:263-7; Reid et al., Proc Natl Acad Sci USA (1990) 87:4299-4303] or the Diptheria toxin A fragment (Dt-A) gene [Nada et al., Cell (1993) 73:1125-35; Yagi et al., Proc Natl Acad Sci USA (1990) 87:9918-9922], which disclosures are hereby incorporated by reference in their entireties. Preferably, the positive selection marker is located within a mouse RUP40 exon sequence so as to interrupt the sequence encoding a mouse RUP40 polypeptide. These replacement vectors are described, for example, by Thomas et al., Cell (1986) 44:419-28; Thomas et al., Cell (1987) 51:503-12; Mansour et al., Nature (1988) 336:348-52; Koller et al., Annu Rev Immunol (1992) 10:705-30; and U.S. Pat. No. 5,631,153; which disclosures are hereby incorporated by reference in their entireties.

The first and second nucleotide sequences (a) and (c) may be indifferently located within a mouse RUP40 regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb, and most preferably from 2 to 4 kb.

Methods of making a transgenic mouse comprising disruption in a selected gene are well known to those of ordinary skill in the art and have been used to successfully inactivate a wide range of genes.

Rat

Analogous or alternative [see, e.g., Zan et al, Nature Biotechnology (2003) 21:645-51; the disclosure of which is hereby incorporated by reference in its entirety] methods may be used to make a transgenic rat comprising a disruption in a RUP40 gene.

Pig

Analogous or alternative methods may be used to make a transgenic pig comprising a disruption in a RUP40 gene [see, e.g., Lai et al., Science (2002) 295:1089-1092; the disclosure of which is hereby incorporated by reference in its entirety].

Cre-LoxP System:

Transgenic Mouse/Rat/Pig Comprising a Cardiomyocyte-Selective Disruption in a RUP40 Gene Mouse These new DNA constructs make use of the site specific recombination system of the P1 phage. The P1 phage possesses a recombinase called Cre that interacts with a 34 base pair loxP site. The loxP site is composed of two palindromic sequences of 13 bp separated by an 8 bp conserved sequence [Hoess R H et al, Nucleic Acids Res (1986) 14:2287-300; which disclosure is hereby incorporated by reference in its entirety]. The recombination by the Cre enzyme between two loxP sites having an identical orientation leads to the deletion of the DNA fragment The Cre-loxP system used in combination with a homologous recombination technique has been first described by Gu et al. [Gu H et al., Cell (1993) 73:1155-64; Gu H et al., Science (1994) 265:103-6; which disclosures are hereby incorporated by reference in their entirety]. Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre)

enzyme within the nucleus of the recombinant cell host. The recombinase enzyme may be brought at the desired time either by (a) incubating the recombinant cell hosts M a culture medium containing this enzyme, by injecting the Cre enzyme directly into the desired cell, such as by lipofection of the enzyme into the cells, such as described by Baubonis et al. [Baubonis W and Sauer B, Nucleic Acids Res (1993) 21:2025-9; which disclosure is hereby incorporated by reference in its entirety]; (b) transfecting the cell host with a vector comprising the Cre coding sequence operably linked to a promoter functional in the recombinant cell host, which promoter being optionally inducible, said vector being introduced in the recombinant cell host, such as described by Gu et al. [Gu H et al., Cell (1993) 73:1155-64; which disclosure is hereby incorporated by reference in its entirety] and Sauer et al. [Sauer B and Henderson N, Proc Natl Acad Sci USA (1988) 85:5166-70; which disclosure is hereby incorporated by reference in its entirety]; (c) introducing into the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. [Gu H et al., Science (1994) 265:103-6; the disclosure of which is hereby incorporated by reference in its entirety].

Vectors and methods using the Cre-loxP system are described, e.g., by Zou et al. (1994); Minamisawa S et al., J Biol Chem (1999) 274:10066-70; Chen et al., J Biol Chem (1998) 273:1252-6; Chen et al., Development (1998) 125: 1943-9; the disclosure of each of which is hereby incorporated by reference in its entirety.

In preferred embodiments of the invention, Cre is introduced into the genome of the cell host by strategy (c) above, wherein said promoter is cardiomyocyte selective and leads to cardiomyocyte-selective disruption of (loxP-flanked; "floxed") mouse RUP40 genomic sequence. In some embodiments, said cardiomyocyte-selective promoter is that for the ventricular specific isoform of myosin light chain 2 (mlc-2v) [Minamisawa S et al., J Biol Chem (1999) 274:10066-70; Chen et al., J Biol Chem (1998) 273:1252-6; the disclosure of each of which is hereby incorporated by reference in its entirety]. Transgenic mice comprising insertion of Cre recombinase coding sequence into the endogenous mlc-2v locus ("mk-2v cre knock-in mice") have been described [Chen et al., Development (1998) 125:1943-9; the disclosure of which is hereby incorporated by reference in its entirety]. Methods for foxing a selected gene are within the purview of those of ordinary skill in the art [see, e.g., Chen et al., Development (1998) 125:1943-9].

In some embodiments, the invention features a method of making a transgenic mouse comprising a cardiomyocyte-selective disruption of a RUP40 gene, comprising crossing the mlc-2 cre allele, supra, with a foxed RUP40 gene.

Other methods of making a transgenic mouse comprising a cardiomyocyte-selective disruption in a RUP40 gene are well known to persons of ordinary skill in the art; see, e.g, Kuhn R and Torres R M, Methods Mol Biol (2002) 180:175-204; Sauer B, Methods (1998) 14:381-92; Gutstein D E et al., Circulation Research (2001) 88:333; Minamino T et al., Circulation Research (2001) 88:587; and Bex A et al, J Urol (2002) 168:2641-2644; the disclosure of each of which is hereby incorporated by reference in its entirety.

Rat

Analogous or alternative [see, e.g., Zan et al, Nature Biotechnology (2003) 21:645-51; the disclosure of which is hereby incorporated by reference in its entirety] methods may be used to make a transgenic rat comprising a cardiomyocyte disruption in a RUP40 gene.

Pig

Analogous or alternative methods may be used to make a transgenic pig comprising a cardiomyocyte-selective disruption in a RUP40 gene [see, e.g., Lai et al., Science (2002) 295:1089-1092; the disclosure of which is hereby incorporated by reference in its entirety].

What is claimed is:

1. A method of identifying a compound capable of inhibiting cardiomyocyte hypertrophy, comprising:
   (a) contacting a candidate compound with a host cell or an isolated membrane thereof comprising a recombinant G protein-coupled receptor comprising an amino acid sequence having at least 95% identity to amino acids 991 to 1,346 of SEQ ID NO:2, wherein said G protein-coupled receptor has constitutive activity;
   (b) determining that the compound inhibits signaling by said G protein-coupled receptor, and
   (c) determining if the compound inhibits hypertrophy of a myocardial cell.

2. The method of claim 1, wherein element (c) comprises:
   (i) contacting the compound with a cardiomyocyte cell in vitro; and
   (ii) determining whether the compound inhibits hypertrophy of the cardiomyocyte cell.

3. The method of claim 1, wherein the method comprises measuring the size of the cardiomyocyte cell or the expression of atrial natriuretic factor (ANF) by the cardiomyocyte cell.

4. The method of claim 1, wherein element (c) comprises:
   (i) administering the compound to a mammal; and
   (ii) determining whether the compound inhibits hypertrophy of the heart of the mammal.

5. The method of claim 4, wherein the mammal is a rat, a mouse or a pig.

6. The method of claim 4, wherein element (ii) comprises evaluating congestive heart failure, congestive cardiomyopathy, heart hypertrophy, left ventricular hypertrophy, right ventricular hypertrophy or hypertrophic cardiomyopathy.

7. The method of claim 1, wherein the method comprises identifying an inverse agonist of the receptor.

8. The method of claim 1, wherein the method comprises identifying an antagonist of the receptor.

9. The method of claim 4, wherein element (ii) comprises evaluating hypertrophy of the heart in congestive heart failure or congestive cardiomyopathy.

10. The method of claim 4, wherein element (ii) comprises evaluating hypertrophy of the heart in post-myocardial infarction re-modeling.

11. The method of claim 1, wherein the signaling is production of a reporter protein by a cell.

12. The method of claim 1, wherein said signaling is production of IP3 in a cell.

* * * * *

SEQUENCE LISTING

```
<160> NUMBER OF SEQ ID NOS: 12

<210> SEQ ID NO 1
<211> LENGTH: 4041
<212> TYPE: DNA
<213> ORGANISM: Homo sapien

<400> SEQUENCE: 1
atgaaatccc caaggagaac cactttgtgc ctcatgttta ttgtgattta ttcttccaaa      60
gctgcactga actggaatta cgagtctact attcatcctt tgagtcttca tgaacatgaa     120
ccagctggtg aagaggcact gaggcaaaaa cgagccgttg ccacaaaaag tcctacggct     180
gaagaataca ctgttaatat tgagatcagt tttgaaaatg catccttcct ggatcctatc     240
aaagcctact tgaacagcct cagttttcca attcatggga ataacactga ccaaattact     300
gacattttga gcataaatgt gacaacagtc tgcagacctg ctggaaatga aatctggtgc     360
tcctgcgaga caggttatgg gtggcctcgg gaaaggtgtc ttcacaatct catttgtcaa     420
gagcgtgacg tcttcctccc agggcaccat tgcagttgcc ttaaagaact gcctcccaat     480
ggaccttttt gcctgcttca ggaagatgtt accctgaaca tgagagtcag actaaatgta     540
ggctttcaag aagacctcat gaacacttcc tccgccctct ataggtccta caagaccgac     600
```

```
ttggaaacag cgttccggaa gggttacgga attttaccag gcttcaaggg cgtgactgtg    660
acagggttca agtctggaag tgtggttgtg acatatgaag tcaagactac accaccatca    720
cttgagttaa tacataaagc caatgaacaa gttgtacaga gcctcaatca gacctacaaa    780
atggactaca actcctttca agcagttact atcaatgaaa gcaatttctt tgtcacacca    840
gaaatcatct ttgaagggga cacagtcagt ctggtgtgtg aaaaggaagt tttgtcctcc    900
aatgtgtctt ggcgctatga agaacagcag ttggaaatcc agaacagcag cagattctcg    960
atttacaccg cacttttcaa caacatgact tcggtgtcca agctcaccat ccacaacatc   1020
actccaggtg atgcaggtga atatgtttgc aaactgatat tagacatttt tgaatatgag   1080
tgcaagaaga aaatagatgt tatgcccatc caaattttgg caaatgaaga aatgaaggtg   1140
atgtgcgaca caatcctgt atctttgaac tgctgcagtc agggtaatgt taattggagc   1200
aaagtagaat ggaagcagga aggaaaaata atatattccag gaacccctga cagacataa   1260 gattctagct gcagcagata cacccctcaag gctgatggaa cccagtgccc aagcgggtcg   1320
tctggaacaa cagtcatcta cacttgtgag ttcatcagtg cctatggagc cagaggcagt   1380
gcaaacataa aagtgacatt catctctgtg gccaatctaa caataacccc ggacccaatt   1440
tctgtttctg agggacaaaa cttttctata aaatgcatca gtgatgtgag taactatgat   1500
gaggtttatt ggaacacttc tgctggaatt aaaatatacc aaagatttta taccacgagg   1560
aggtatcttg atggagcaga atcagtactg acagtcaaga cctcgaccag ggagtggaat   1620
ggaacctatc actgcatatt tagatataag aattcataca gtattgcaac caaagacgtc   1680
attgttcacc cgctgcctct aaagctgaac atcatggttg atccttttgga agctactgtt   1740 tcatgcagtg gttcccatca catcaagtgc tgcatagagg aggatggaga ctacaaagtt   1800
actttccata tgggttcctc atcccttcct gctgcaaaag aagttaacaa aaaacaagtg   1860
tgctacaaac acaatttcaa tgcaagctca gtttcctggt gttcaaaaac tgttgatgtg   1920
tgttgtcact ttaccaatgc tgctaataat tcagtttgga gcccatctat gaagctgaat   1980
ctggttcctg ggaaaaacat cacatgccag gatcccgtaa taggtgtcgg agagccgggg   2040
aaagtcatcc agaagctatg ccggttctca aacgttccca gcagccctga gagtccatt   2100 ggcgggacca tcacttacaa atgtgtaggc tcccagtggg aggagaagag aaatgactgc   2160
atctctgccc caataaacag tctgctccag atggctaagg ctttgatcaa gagcccctct   2220
caggatgaga tgctccctac atacctgaag gatcttttcta ttagcataga caaagcggaa   2280
catgaaatca gctcttctcc tgggagtctg ggagccatta ttaacatcct tgatctgctc   2340
tcaacagttc caacccaagt aaattcagaa atgatgacgc acgtgctctc tacggttaat   2400
gtcatccttg gcaagcccgt cttgaacacc tggaaggttt tacaacagca atggaccaat   2460
cagagttcac agctactaca ttcagtggaa agattttccc aagcattaca gtcaggagat   2520
agccctcctt tgtccttctc ccaaactaat gtgcagatga gcagcacggt aatcaagtcc   2580
agccacccag aaacctatca acagaggttt gttttcccat actttgacct ctggggcaat   2640
gtggtcattg acaagagcta tctagaaaac ttgcagtcgg attcgtctat tgtcaccatg   2700
gctttcccaa ctctccaagc catccttgct caggatatcc aggaaaataa cttttgcagag   2760 agcttagtga tgacaaccac tgtcagccac aatacgacta tgccattcag gatttcaatg   2820
acttttaaga caaatagccc ttcaggcggc gaaacgaagt gtgtcttctg gaacttcagg   2880
cttgccaaca acacaggggg gtgggacagc agtgggtgct atgttgaaga aggtgatggg   2940
gacaatgtca cctgtatctg tgaccaccta acatcattct ccatcctcat gtcccctgac   3000
```

-continued

```
tccccagatc ctagttctct cctgggaata ctcctggata ttatttctta tgttggggtg    3060
ggcttttcca tcttgagctt ggcagcctgt ctagttgtgg aagctgtggt gtggaaatcg    3120
gtgaccaaga atcggacttc ttatatgcgc cacacctgca tagtgaatat cgctgcctcc    3180
cttctggtcg ccaacacctg gttcattgtg gtcgctgcca tccaggacaa tcgctacata    3240
ctctgcaaga cagcctgtgt ggctgccacc ttcttcatcc acttcttcta cctcagcgtc    3300
ttcttctgga tgctgacact gggcctcatg ctgttctatc gcctggtttt cattctgcat    3360
gaaacaagca ggtccactca gaaagccatt gccttctgtc ttggctatgg ctgcccactt    3420
gccatctcgg tcatcacgct gggagccacc cagccccggg aagtctatac gaggaagaat    3480
gtctgttggc tcaactggga ggacaccaag gccctgctgg ctttcgccat cccagcactg    3540
atcattgtgg tggtgaacat aaccatcact attgtggtca tcaccaagat cctgaggcct    3600
tccattggag acaagccatg caagcaggag aagagcagcc tgtttcagat cagcaagagc    3660
attggggtcc tcacaccact cttgggcctc acttggggtt ttggtctcac cactgtgttc    3720
ccagggacca accttgtgtt ccatatcata tttgccatcc tcaatgtctt ccagggatta    3780
ttcattttac tctttggatg cctctgggat ctgaaggtac aggaagcttt gctgaataag    3840
ttttcattgt cgagatggtc ttcacagcac tcaaagtcaa catccctggg ttcatccaca    3900
cctgtgtttt ctatgagttc tccaatatca aggagattta acaatttgtt tggtaaaaca    3960
ggaacgtata atgtttccac cccagaagca accagctcat ccctggaaaa ctcatccagt    4020
gcttcttcgt tgctcaacta a                                              4041
```

<210> SEQ ID NO 2
<211> LENGTH: 1346
<212> TYPE: PRT
<213> ORGANISM: Homo sapien
<220> FEATURE:
<221> NAME/KEY: VARIANT
<222> LOCATION: 604
<223> OTHER INFORMATION: Polymorphic amino acid Met or Thr
<220> FEATURE:
<221> NAME/KEY: VARIANT
<222> LOCATION: 801
<223> OTHER INFORMATION: Polymorphic amino acid Val or Ile
<220> FEATURE:
<221> NAME/KEY: VARIANT
<222> LOCATION: 856
<223> OTHER INFORMATION: Polymorphic amino acid Thr or Met

<400> SEQUENCE: 2

```
Met Lys Ser Pro Arg Arg Thr Thr Leu Cys Leu Met Phe Ile Val Ile
  1               5                  10                  15

Tyr Ser Ser Lys Ala Ala Leu Asn Trp Asn Tyr Glu Ser Thr Ile His
                 20                  25                  30

Pro Leu Ser Leu His Glu His Glu Pro Ala Gly Glu Glu Ala Leu Arg
         35                  40                  45

Gln Lys Arg Ala Val Ala Thr Lys Ser Pro Thr Ala Glu Glu Tyr Thr
     50                  55                  60

Val Asn Ile Glu Ile Ser Phe Glu Asn Ala Ser Phe Leu Asp Pro Ile
 65                  70                  75                  80

Lys Ala Tyr Leu Asn Ser Leu Ser Phe Pro Ile His Gly Asn Asn Thr
                 85                  90                  95

Asp Gln Ile Thr Asp Ile Leu Ser Ile Asn Val Thr Thr Val Cys Arg
            100                 105                 110

Pro Ala Gly Asn Glu Ile Trp Cys Ser Cys Glu Thr Gly Tyr Gly Trp
        115                 120                 125
```

-continued

```
Pro Arg Glu Arg Cys Leu His Asn Leu Ile Cys Gln Glu Arg Asp Val
    130                 135                 140
Phe Leu Pro Gly His His Cys Ser Cys Leu Lys Glu Leu Pro Pro Asn
145                 150                 155                 160
Gly Pro Phe Cys Leu Leu Gln Glu Asp Val Thr Leu Asn Met Arg Val
                165                 170                 175
Arg Leu Asn Val Gly Phe Gln Glu Asp Leu Met Asn Thr Ser Ser Ala
            180                 185                 190
Leu Tyr Arg Ser Tyr Lys Thr Asp Leu Glu Thr Ala Phe Arg Lys Gly
        195                 200                 205
Tyr Gly Ile Leu Pro Gly Phe Lys Gly Val Thr Val Thr Gly Phe Lys
    210                 215                 220
Ser Gly Ser Val Val Thr Tyr Glu Val Lys Thr Thr Pro Pro Ser
225                 230                 235                 240
Leu Glu Leu Ile His Lys Ala Asn Glu Gln Val Val Gln Ser Leu Asn
                245                 250                 255
Gln Thr Tyr Lys Met Asp Tyr Asn Ser Phe Gln Ala Val Thr Ile Asn
            260                 265                 270
Glu Ser Asn Phe Phe Val Thr Pro Glu Ile Ile Phe Glu Gly Asp Thr
        275                 280                 285
Val Ser Leu Val Cys Glu Lys Glu Val Leu Ser Ser Asn Val Ser Trp
    290                 295                 300
Arg Tyr Glu Glu Gln Gln Leu Glu Ile Gln Asn Ser Ser Arg Phe Ser
305                 310                 315                 320
Ile Tyr Thr Ala Leu Phe Asn Asn Met Thr Ser Val Ser Lys Leu Thr
                325                 330                 335
Ile His Asn Ile Thr Pro Gly Asp Ala Gly Glu Tyr Val Cys Lys Leu
            340                 345                 350
Ile Leu Asp Ile Phe Glu Tyr Glu Cys Lys Lys Ile Asp Val Met
        355                 360                 365
Pro Ile Gln Ile Leu Ala Asn Glu Glu Met Lys Val Met Cys Asp Asn
    370                 375                 380
Asn Pro Val Ser Leu Asn Cys Cys Ser Gln Gly Asn Val Asn Trp Ser
385                 390                 395                 400
Lys Val Glu Trp Lys Gln Glu Gly Lys Ile Asn Ile Pro Gly Thr Pro
                405                 410                 415
Glu Thr Asp Ile Asp Ser Ser Cys Ser Arg Tyr Thr Leu Lys Ala Asp
            420                 425                 430
Gly Thr Gln Cys Pro Ser Gly Ser Gly Thr Thr Val Ile Tyr Thr
        435                 440                 445
Cys Glu Phe Ile Ser Ala Tyr Gly Ala Arg Gly Ser Ala Asn Ile Lys
    450                 455                 460
Val Thr Phe Ile Ser Val Ala Asn Leu Thr Ile Thr Pro Asp Pro Ile
465                 470                 475                 480
Ser Val Ser Glu Gly Gln Asn Phe Ser Ile Lys Cys Ile Ser Asp Val
                485                 490                 495
Ser Asn Tyr Asp Glu Val Tyr Trp Asn Thr Ser Ala Gly Ile Lys Ile
            500                 505                 510
Tyr Gln Arg Phe Tyr Thr Thr Arg Arg Tyr Leu Asp Gly Ala Glu Ser
        515                 520                 525
Val Leu Thr Val Lys Thr Ser Thr Arg Glu Trp Asn Gly Thr Tyr His
    530                 535                 540
Cys Ile Phe Arg Tyr Lys Asn Ser Tyr Ser Ile Ala Thr Lys Asp Val
545                 550                 555                 560
```

```
Ile Val His Pro Leu Pro Leu Lys Leu Asn Ile Met Val Asp Pro Leu
            565                 570                 575

Glu Ala Thr Val Ser Cys Ser Gly Ser His His Ile Lys Cys Cys Ile
            580                 585                 590

Glu Glu Asp Gly Asp Tyr Lys Val Thr Phe His Met Gly Ser Ser Ser
            595                 600                 605

Leu Pro Ala Ala Lys Glu Val Asn Lys Lys Gln Val Cys Tyr Lys His
            610                 615                 620

Asn Phe Asn Ala Ser Ser Val Ser Trp Cys Ser Lys Thr Val Asp Val
625                 630                 635                 640

Cys Cys His Phe Thr Asn Ala Ala Asn Asn Ser Val Trp Ser Pro Ser
                645                 650                 655

Met Lys Leu Asn Leu Val Pro Gly Glu Asn Ile Thr Cys Gln Asp Pro
                660                 665                 670

Val Ile Gly Val Gly Glu Pro Gly Lys Val Ile Gln Lys Leu Cys Arg
                675                 680                 685

Phe Ser Asn Val Pro Ser Ser Pro Glu Ser Pro Ile Gly Gly Thr Ile
                690                 695                 700

Thr Tyr Lys Cys Val Gly Ser Gln Trp Glu Glu Lys Arg Asn Asp Cys
705                 710                 715                 720

Ile Ser Ala Pro Ile Asn Ser Leu Leu Gln Met Ala Lys Ala Leu Ile
                725                 730                 735

Lys Ser Pro Ser Gln Asp Glu Met Leu Pro Thr Tyr Leu Lys Asp Leu
                740                 745                 750

Ser Ile Ser Ile Asp Lys Ala Glu His Glu Ile Ser Ser Ser Pro Gly
                755                 760                 765

Ser Leu Gly Ala Ile Ile Asn Ile Leu Asp Leu Leu Ser Thr Val Pro
            770                 775                 780

Thr Gln Val Asn Ser Glu Met Met Thr His Val Leu Ser Thr Val Asn
785                 790                 795                 800

Val Ile Leu Gly Lys Pro Val Leu Asn Thr Trp Lys Val Leu Gln Gln
                805                 810                 815

Gln Trp Thr Asn Gln Ser Ser Gln Leu Leu His Ser Val Glu Arg Phe
                820                 825                 830

Ser Gln Ala Leu Gln Ser Gly Asp Ser Pro Pro Leu Ser Phe Ser Gln
                835                 840                 845

Thr Asn Val Gln Met Ser Ser Thr Val Ile Lys Ser Ser His Pro Glu
850                 855                 860

Thr Tyr Gln Gln Arg Phe Val Phe Pro Tyr Phe Asp Leu Trp Gly Asn
865                 870                 875                 880

Val Val Ile Asp Lys Ser Tyr Leu Glu Asn Leu Gln Ser Asp Ser Ser
                885                 890                 895

Ile Val Thr Met Ala Phe Pro Thr Leu Gln Ala Ile Leu Ala Gln Asp
                900                 905                 910

Ile Gln Glu Asn Asn Phe Ala Glu Ser Leu Val Met Thr Thr Thr Val
            915                 920                 925

Ser His Asn Thr Thr Met Pro Phe Arg Ile Ser Met Thr Phe Lys Asn
            930                 935                 940

Asn Ser Pro Ser Gly Gly Glu Thr Lys Cys Val Phe Trp Asn Phe Arg
945                 950                 955                 960

Leu Ala Asn Asn Thr Gly Gly Trp Asp Ser Ser Gly Cys Tyr Val Glu
                965                 970                 975

Glu Gly Asp Gly Asp Asn Val Thr Cys Ile Cys Asp His Leu Thr Ser
```

```
            980                 985                 990
Phe Ser Ile Leu Met Ser Pro Asp Ser Pro Asp Pro Ser Ser Leu Leu
        995                1000               1005
Gly Ile Leu Leu Asp Ile Ile Ser Tyr Val Gly Val Gly Phe Ser
    1010                1015               1020
Ile Leu Ser Leu Ala Ala Cys Leu Val Val Glu Ala Val Val Trp
    1025                1030               1035
Lys Ser Val Thr Lys Asn Arg Thr Ser Tyr Met Arg His Thr Cys
    1040                1045               1050
Ile Val Asn Ile Ala Ala Ser Leu Leu Val Ala Asn Thr Trp Phe
    1055                1060               1065
Ile Val Val Ala Ala Ile Gln Asp Asn Arg Tyr Ile Leu Cys Lys
    1070                1075               1080
Thr Ala Cys Val Ala Ala Thr Phe Phe Ile His Phe Phe Tyr Leu
    1085                1090               1095
Ser Val Phe Phe Trp Met Leu Thr Leu Gly Leu Met Leu Phe Tyr
    1100                1105               1110
Arg Leu Val Phe Ile Leu His Glu Thr Ser Arg Ser Thr Gln Lys
    1115                1120               1125
Ala Ile Ala Phe Cys Leu Gly Tyr Gly Cys Pro Leu Ala Ile Ser
    1130                1135               1140
Val Ile Thr Leu Gly Ala Thr Gln Pro Arg Glu Val Tyr Thr Arg
    1145                1150               1155
Lys Asn Val Cys Trp Leu Asn Trp Glu Asp Thr Lys Ala Leu Leu
    1160                1165               1170
Ala Phe Ala Ile Pro Ala Leu Ile Ile Val Val Val Asn Ile Thr
    1175                1180               1185
Ile Thr Ile Val Val Ile Thr Lys Ile Leu Arg Pro Ser Ile Gly
    1190                1195               1200
Asp Lys Pro Cys Lys Gln Glu Lys Ser Ser Leu Phe Gln Ile Ser
    1205                1210               1215
Lys Ser Ile Gly Val Leu Thr Pro Leu Leu Gly Leu Thr Trp Gly
    1220                1225               1230
Phe Gly Leu Thr Thr Val Phe Pro Gly Thr Asn Leu Val Phe His
    1235                1240               1245
Ile Ile Phe Ala Ile Leu Asn Val Phe Gln Gly Leu Phe Ile Leu
    1250                1255               1260
Leu Phe Gly Cys Leu Trp Asp Leu Lys Val Gln Glu Ala Leu Leu
    1265                1270               1275
Asn Lys Phe Ser Leu Ser Arg Trp Ser Ser Gln His Ser Lys Ser
    1280                1285               1290
Thr Ser Leu Gly Ser Ser Thr Pro Val Phe Ser Met Ser Ser Pro
    1295                1300               1305
Ile Ser Arg Arg Phe Asn Asn Leu Phe Gly Lys Thr Gly Thr Tyr
    1310                1315               1320
Asn Val Ser Thr Pro Glu Ala Thr Ser Ser Ser Leu Glu Asn Ser
    1325                1330               1335
Ser Ser Ala Ser Ser Leu Leu Asn
    1340                1345

<210> SEQ ID NO 3
<211> LENGTH: 4050
<212> TYPE: DNA
<213> ORGANISM: Rat
```

<400> SEQUENCE: 3

```
atgaaatcgt caaggactgt cacgctctac tttgtgctta ttgtgatttg ttcctcagaa     60
gctacatgga gcaggccagc agagcccatt gtccatcctt tgattctcca agaacatgaa    120
ctagcagggg aagagctact gaggccaaaa agagcagttg cagtgggtgg tcctgtggca    180
gaagaataca ccgtggatgt tgagatcagt tttgaaaatg tctccttcct ggagtccatc    240
agagctcact taaacagcct ccgttttcca gttcaggga acggcactga cattttgagt    300
atggcaatga ctacagtctg cactcctact gggaatgacc tcttgtgctt ctgcgagaaa    360
ggctaccagt ggcctgagga aaggtgtctc tcctctctca cttgtcaaga gcatgacagc    420
gccctgccag gccgatactg caattgtctg aaaggacttc ctccccaagg acctttctgc    480
cagctcccag aaacatacat taccttaaaa atcaaagtca gactgaacat aggatttcaa    540
gaagacctag agaacacatc ctctgccctc tataggtcct acaagactga tctggaaaga    600
gcgttccgag cggttacag aactttacca ggattcagat cggtgactgt gacacagttc    660
accaagggca gcgtggttgt ggactacata gtcgaggttg catcggcacc actgcctgga    720
tcaattcata aagccaatga gcaagtcata cagaacctca accagactta caaaatggac    780
tacaactcct tccaaggaac accaagcaat gaaacaaagt tcactgtgac accagagttc    840
atctttgaag agacaatgt aactctggaa tgcgaaagtg aattcgtgtc ctccaacaca    900
tcttggttct atggagaaaa acggtctgac atccagaaca gtgacaaatt ctccattcac    960
acctcaatca tcaacaatat aagcctggtc acccgcctca ctattttcaa cttcacacag   1020
catgatgcag gcttatatgg ttgcaatgtg acactggata ttttttgaata tgggacagtc   1080
agaaaattag atgtcactcc catccggatt ttggccaagg aagagagaaa ggtggtgtgt   1140
gacaataacc ctatatcgtt gaactgctgc agcgagaata tcgcgaactg gagcagaatc   1200
gagtggaaac aggagggaa aataaacatt gaagggaccc cagaaacaga cctagagtct   1260
agctgcagca cttatacact caaggcagat ggaacccagt gtcccagtgg ttcttctgga   1320
acaacagtca tctacacgtg tgagttcgtc agcgtctacg gagccaaagg cagtaagaac   1380
atagccgtga ccttcacctc tgtagccaac ctaacaataa ccccggaccc aatttctgtt   1440
tctgagggac aaagcttttc tataacttgc ctcagcgatg tgagtagctt tgatgaggtg   1500
tactggaaca cttccgctgg tattaaaatc catccaaggt tttataccat gaggaggtat   1560
cgggatggag cagagtcggt gctgacggtg aagacctcca ccagagagtg aacggaacc    1620
taccactgca tatttagata taagaattca tacagcatag ccaccaaaga tgtcactgtt   1680
caccctctgc ctctggagtc agacatcatg atggatcctt ggaagccag tggtctgtgc    1740
accagttccc atcagttcaa gtgctgcata aagagaacg atggggaaga gtacattgtg   1800
actttccacg tggattcctc atcctttcct gctgaaagag aagttattgg caagcaggca   1860
tgctacacat acagtctccc aggaaagtta ccatcacggt gtcccaaaga cattgacgtg   1920
ttctgccact ttaccaatgc agccaacagc tcagtccgga gcccatctat gaagcttacc   1980
cttgttccag gaagaatat cacatgccag gatcccatca taggtattgg ggaacctggg   2040
aaagtcatcc agaagctgtg ccagtttgca ggtgttccta gaagcccctgg acagaccatt   2100
ggtggaaccg tcacttataa atgtgtaggc tcccagtgga aggaggagac aagggcctgc   2160
atatcagccc caatcaatgg tttgctccag ttggccaagg ctttgatcaa gagcccctcc   2220
caggatcaga agctccctaa atacctgcgg gaccttttctg ttagcactgg aaggaagaa   2280
caggatatac gctcatcgcc cgggagcctg ggagccatca tcagcatcct tgatttgctt   2340
```

```
tcaacagttc ccactcaagt gaattcagaa atgatgaggg atatacttgc taccattaat    2400
gtcatcttag acaagtccac cttgaactcc tgggagaagt tactacagca acagagcaac    2460
cagagctctc agttcctgca gtcagtggag aggttttcca aagcgctcga gctgggagac    2520
agcacccctc ccttcctctt ccaccctaat gttcagatga gagcatggt gataaaacgt     2580
ggccacgccc aaatgtacca acagaaattt gtcttcacag actctgacct atggggtgat    2640
gtagccattg atgagtgtca gctgggaagc ttgcagcctg attcatcgat cgttactgtg    2700
gctttcccaa ctctcaaagc catcctggcc caggatggac agagaaagac ccctccaac     2760
agcctagtaa tgaccaccac tgtcagccat aatatcgtca agccttttag gatttctatg    2820
acattcaaga acaaccatcg ttcgggtggc aagccacagt gtgtcttctg aacttcagc    2880
cttgccaata atacaggggg ctgggatagc agtgggtgca ctgtggaaga tgatggtagg   2940
gacaataggg acagagtctt ctgcaagtgt aaccacctga cgtcattctc cattctcatg    3000
tccccagact ccccagaccc aggatctctt ttaaaaatac ttctggatat catttcttac    3060
atcgggttgg gcttttccat agtcagctta gctgcctgtc tagttgtgga agccatggtg    3120
tggaaatcag tgaccaagaa ccgaacttcc tatatgcgcc acatctgcat cgtcaacatt    3180
gccctttgcc ttctgattgc tgacatctgg ttcattgtgg ctggtgctat ccacgatggg    3240
cattacccac tcaacgaaac agcctgtgtg gccgccacat tcttcattca cttcttctac    3300
ctcagtgtct tcttctggat gctaactctg ggcctcatgc tcttctaccg gctgattttc    3360
attctacatg acgcgagcaa gtccacgcag aaagccattg cctttctct aggctatggc    3420
tgtccactca ttatctcatc catcacagtg ggggttacac agccacagga gtttacatg    3480
aggaagaatg catgttggct caactgggag acaccagag cactgctggc ttttgctatc     3540
ccagcgttga ttattgtggt ggtgaacgtg agcatcacag ttgtggtcat caccaagatc    3600
ctaaggccct ccgtcggaga caagccaggc aagcaggaaa agagcagcct attccagatc    3660
agcaagagca ttggagtcct cacgccactc ttggggctca cttggggttt tggtctggcc    3720
acagtgatcc aggggagcaa tgctgtgttc cacatcatat ttactctcct caatgccttt    3780
caggggctct tcattttgct cttttggctgc ctctgggatc agaaggtaca ggaagctttg    3840
ctgcataagt tttcattgtc aaggtggtct tctcaacact caaagtcaac atccttaggt    3900
tcatcaacac ctgtgttttc gatgagttct ccgatatccc gaagatttaa taatcttttt    3960
ggtaaaacag gaacatataa cgtttccacc ccagagacaa ccagctcatc cgtggaaaat    4020
tcctctagtg cttactcatt gctcaactag                                    4050
```

<210> SEQ ID NO 4
<211> LENGTH: 1349
<212> TYPE: PRT
<213> ORGANISM: Rat

<400> SEQUENCE: 4

Met Lys Ser Ser Arg Thr Val Thr Leu Tyr Phe Val Leu Ile Val Ile
1               5                   10                  15

Cys Ser Ser Glu Ala Thr Trp Ser Arg Pro Ala Glu Pro Ile Val His
            20                  25                  30

Pro Leu Ile Leu Gln Glu His Glu Leu Ala Gly Glu Glu Leu Leu Arg
        35                  40                  45

Pro Lys Arg Ala Val Ala Val Gly Gly Pro Val Ala Glu Glu Tyr Thr
    50                  55                  60

Val Asp Val Glu Ile Ser Phe Glu Asn Val Ser Phe Leu Glu Ser Ile
65                  70                  75                  80

-continued

```
Arg Ala His Leu Asn Ser Leu Arg Phe Pro Val Gln Gly Asn Gly Thr
                85                  90                  95
Asp Ile Leu Ser Met Ala Met Thr Thr Val Cys Thr Pro Thr Gly Asn
               100                 105                 110
Asp Leu Leu Cys Phe Cys Glu Lys Gly Tyr Gln Trp Pro Glu Glu Arg
               115                 120                 125
Cys Leu Ser Ser Leu Thr Cys Gln Glu His Asp Ser Ala Leu Pro Gly
130                 135                 140
Arg Tyr Cys Asn Cys Leu Lys Gly Leu Pro Gln Gly Pro Phe Cys
145                 150                 155                 160
Gln Leu Pro Glu Thr Tyr Ile Thr Leu Lys Ile Lys Val Arg Leu Asn
               165                 170                 175
Ile Gly Phe Gln Glu Asp Leu Glu Asn Thr Ser Ser Ala Leu Tyr Arg
               180                 185                 190
Ser Tyr Lys Thr Asp Leu Glu Arg Ala Phe Arg Ala Gly Tyr Arg Thr
               195                 200                 205
Leu Pro Gly Phe Arg Ser Val Thr Val Thr Gln Phe Thr Lys Gly Ser
210                 215                 220
Val Val Val Asp Tyr Ile Val Glu Val Ala Ser Ala Pro Leu Pro Gly
225                 230                 235                 240
Ser Ile His Lys Ala Asn Glu Gln Val Ile Gln Asn Leu Asn Gln Thr
               245                 250                 255
Tyr Lys Met Asp Tyr Asn Ser Phe Gln Gly Thr Pro Ser Asn Glu Thr
               260                 265                 270
Lys Phe Thr Val Thr Pro Glu Phe Ile Phe Glu Gly Asp Asn Val Thr
               275                 280                 285
Leu Glu Cys Glu Ser Glu Phe Val Ser Ser Asn Thr Ser Trp Phe Tyr
               290                 295                 300
Gly Glu Lys Arg Ser Asp Ile Gln Asn Ser Asp Lys Phe Ser Ile His
305                 310                 315                 320
Thr Ser Ile Ile Asn Asn Ile Ser Leu Val Thr Arg Leu Thr Ile Phe
               325                 330                 335
Asn Phe Thr Gln His Asp Ala Gly Leu Tyr Gly Cys Asn Val Thr Leu
               340                 345                 350
Asp Ile Phe Glu Tyr Gly Thr Val Arg Lys Leu Asp Val Thr Pro Ile
               355                 360                 365
Arg Ile Leu Ala Lys Glu Glu Arg Lys Val Val Cys Asp Asn Asn Pro
370                 375                 380
Ile Ser Leu Asn Cys Cys Ser Glu Asn Ile Ala Asn Trp Ser Arg Ile
385                 390                 395                 400
Glu Trp Lys Gln Glu Gly Lys Ile Asn Ile Gly Thr Pro Glu Thr
               405                 410                 415
Asp Leu Glu Ser Ser Cys Ser Thr Tyr Thr Leu Lys Ala Asp Gly Thr
               420                 425                 430
Gln Cys Pro Ser Gly Ser Ser Gly Thr Thr Val Ile Tyr Thr Cys Glu
               435                 440                 445
Phe Val Ser Val Tyr Gly Ala Lys Gly Ser Lys Asn Ile Ala Val Thr
               450                 455                 460
Phe Thr Ser Val Ala Asn Leu Thr Ile Thr Pro Asp Pro Ile Ser Val
465                 470                 475                 480
Ser Glu Gly Gln Ser Phe Ser Ile Thr Cys Leu Ser Asp Val Ser Ser
               485                 490                 495
Phe Asp Glu Val Tyr Trp Asn Thr Ser Ala Gly Ile Lys Ile His Pro
```

```
                500             505             510
Arg Phe Tyr Thr Met Arg Tyr Arg Asp Gly Ala Glu Ser Val Leu
            515             520             525

Thr Val Lys Thr Ser Thr Arg Glu Trp Asn Gly Thr Tyr His Cys Ile
        530             535             540

Phe Arg Tyr Lys Asn Ser Tyr Ser Ile Ala Thr Lys Asp Val Thr Val
545             550             555             560

His Pro Leu Pro Leu Glu Ser Asp Ile Met Met Asp Pro Leu Glu Ala
            565             570             575

Ser Gly Leu Cys Thr Ser Ser His Gln Phe Lys Cys Cys Ile Glu Glu
            580             585             590

Asn Asp Gly Glu Glu Tyr Ile Val Thr Phe His Val Asp Ser Ser Ser
            595             600             605

Phe Pro Ala Glu Arg Glu Val Ile Gly Lys Gln Ala Cys Tyr Thr Tyr
        610             615             620

Ser Leu Pro Gly Lys Leu Pro Ser Arg Cys Pro Lys Asp Ile Asp Val
625             630             635             640

Phe Cys His Phe Thr Asn Ala Ala Asn Ser Ser Val Arg Ser Pro Ser
                645             650             655

Met Lys Leu Thr Leu Val Pro Gly Lys Asn Ile Thr Cys Gln Asp Pro
            660             665             670

Ile Ile Gly Ile Gly Glu Pro Gly Lys Val Ile Gln Lys Leu Cys Gln
            675             680             685

Phe Ala Gly Val Ser Arg Ser Pro Gly Gln Thr Ile Gly Gly Thr Val
        690             695             700

Thr Tyr Lys Cys Val Gly Ser Gln Trp Lys Glu Glu Thr Arg Ala Cys
705             710             715             720

Ile Ser Ala Pro Ile Asn Gly Leu Leu Gln Leu Ala Lys Ala Leu Ile
                725             730             735

Lys Ser Pro Ser Gln Asp Gln Lys Leu Pro Lys Tyr Leu Arg Asp Leu
            740             745             750

Ser Val Ser Thr Gly Lys Glu Glu Gln Asp Ile Arg Ser Ser Pro Gly
            755             760             765

Ser Leu Gly Ala Ile Ile Ser Ile Leu Asp Leu Leu Ser Thr Val Pro
770             775             780

Thr Gln Val Asn Ser Glu Met Met Arg Asp Ile Leu Ala Thr Ile Asn
785             790             795             800

Val Ile Leu Asp Lys Ser Thr Leu Asn Ser Trp Glu Lys Leu Leu Gln
                805             810             815

Gln Gln Ser Asn Gln Ser Ser Gln Phe Leu Gln Ser Val Glu Arg Phe
            820             825             830

Ser Lys Ala Leu Glu Leu Gly Asp Ser Thr Pro Pro Phe Leu Phe His
            835             840             845

Pro Asn Val Gln Met Lys Ser Met Val Ile Lys Arg Gly His Ala Gln
            850             855             860

Met Tyr Gln Gln Lys Phe Val Phe Thr Asp Ser Asp Leu Trp Gly Asp
865             870             875             880

Val Ala Ile Asp Glu Cys Gln Leu Gly Ser Leu Gln Pro Asp Ser Ser
                885             890             895

Ile Val Thr Val Ala Phe Pro Thr Leu Lys Ala Ile Leu Ala Gln Asp
            900             905             910

Gly Gln Arg Lys Thr Pro Ser Asn Ser Leu Val Met Thr Thr Thr Val
            915             920             925
```

-continued

Ser His Asn Ile Val Lys Pro Phe Arg Ile Ser Met Thr Phe Lys Asn
930                 935                 940

Asn His Arg Ser Gly Gly Lys Pro Gln Cys Val Phe Trp Asn Phe Ser
945                 950                 955                 960

Leu Ala Asn Asn Thr Gly Gly Trp Asp Ser Ser Gly Cys Thr Val Glu
                965                 970                 975

Asp Asp Gly Arg Asp Asn Arg Asp Arg Val Phe Cys Lys Cys Asn His
                980                 985                 990

Leu Thr Ser Phe Ser Ile Leu Met Ser Pro Asp Ser Pro Asp Pro Gly
        995                 1000                1005

Ser Leu Leu Lys Ile Leu Leu Asp Ile Ile Ser Tyr Ile Gly Leu
    1010                1015                1020

Gly Phe Ser Ile Val Ser Leu Ala Ala Cys Leu Val Val Glu Ala
    1025                1030                1035

Met Val Trp Lys Ser Val Thr Lys Asn Arg Thr Ser Tyr Met Arg
    1040                1045                1050

His Ile Cys Ile Val Asn Ile Ala Leu Cys Leu Leu Ile Ala Asp
    1055                1060                1065

Ile Trp Phe Ile Val Ala Gly Ala Ile His Asp Gly His Tyr Pro
    1070                1075                1080

Leu Asn Glu Thr Ala Cys Val Ala Ala Thr Phe Phe Ile His Phe
    1085                1090                1095

Phe Tyr Leu Ser Val Phe Phe Trp Met Leu Thr Leu Gly Leu Met
    1100                1105                1110

Leu Phe Tyr Arg Leu Ile Phe Ile Leu His Asp Ala Ser Lys Ser
    1115                1120                1125

Thr Gln Lys Ala Ile Ala Phe Ser Leu Gly Tyr Gly Cys Pro Leu
    1130                1135                1140

Ile Ile Ser Ser Ile Thr Val Gly Val Thr Gln Pro Gln Glu Val
    1145                1150                1155

Tyr Met Arg Lys Asn Ala Cys Trp Leu Asn Trp Glu Asp Thr Arg
    1160                1165                1170

Ala Leu Leu Ala Phe Ala Ile Pro Ala Leu Ile Ile Val Val Val
    1175                1180                1185

Asn Val Ser Ile Thr Val Val Ile Thr Lys Ile Leu Arg Pro
    1190                1195                1200

Ser Val Gly Asp Lys Pro Gly Lys Gln Glu Lys Ser Ser Leu Phe
    1205                1210                1215

Gln Ile Ser Lys Ser Ile Gly Val Leu Thr Pro Leu Leu Gly Leu
    1220                1225                1230

Thr Trp Gly Phe Gly Leu Ala Thr Val Ile Gln Gly Ser Asn Ala
    1235                1240                1245

Val Phe His Ile Ile Phe Thr Leu Leu Asn Ala Phe Gln Gly Leu
    1250                1255                1260

Phe Ile Leu Leu Phe Gly Cys Leu Trp Asp Gln Lys Val Gln Glu
    1265                1270                1275

Ala Leu Leu His Lys Phe Ser Leu Ser Arg Trp Ser Ser Gln His
    1280                1285                1290

Ser Lys Ser Thr Ser Leu Gly Ser Ser Thr Pro Val Phe Ser Met
    1295                1300                1305

Ser Ser Pro Ile Ser Arg Arg Phe Asn Asn Leu Phe Gly Lys Thr
    1310                1315                1320

Gly Thr Tyr Asn Val Ser Thr Pro Glu Thr Thr Ser Ser Ser Val
    1325                1330                1335

```
Glu Asn Ser Ser Ser Ala Tyr Ser Leu Leu Asn
    1340                1345
```

<210> SEQ ID NO 5
<211> LENGTH: 423
<212> TYPE: DNA
<213> ORGANISM: Mouse

<400> SEQUENCE: 5

```
gcctgtctag ttgtggaagc catggtgtgg aaatctgtga ccaagaaccg aacttcctat      60
atgcgccaca tctgcatagt caacattgcc ttttgccttc tgattgctga catctggttc     120
attgtggctg gtgctatcca cgacggtcgc tacccactca acgaaacagc ctgtgtggcc     180
gccacattct tcattcactt cttctacctc agtgtcttct tctggatgct aactctaggc     240
ctcatgctct tctaccggct gattttcatt ctacacgatg caagcaagtc cactcagaaa     300
gccatcgcat ttctctagg ctatggctgt cccctcatta tctcctctat acagtgggg      360
gttacgcagc cacaggaagt ctacatgagg aagaacgcgt gttggctcaa ctgggaggac     420
acc                                                                   423
```

<210> SEQ ID NO 6
<211> LENGTH: 141
<212> TYPE: PRT
<213> ORGANISM: Mouse

<400> SEQUENCE: 6

```
Ala Cys Leu Val Val Glu Ala Met Val Trp Lys Ser Val Thr Lys Asn
1               5                   10                  15
Arg Thr Ser Tyr Met Arg His Ile Cys Ile Val Asn Ile Ala Phe Cys
            20                  25                  30
Leu Leu Ile Ala Asp Ile Trp Phe Ile Val Ala Gly Ala Ile His Asp
        35                  40                  45
Gly Arg Tyr Pro Leu Asn Glu Thr Ala Cys Val Ala Ala Thr Phe Phe
    50                  55                  60
Ile His Phe Phe Tyr Leu Ser Val Phe Phe Trp Met Leu Thr Leu Gly
65                  70                  75                  80
Leu Met Leu Phe Tyr Arg Leu Ile Phe Ile Leu His Asp Ala Ser Lys
                85                  90                  95
Ser Thr Gln Lys Ala Ile Ala Phe Ser Leu Gly Tyr Gly Cys Pro Leu
            100                 105                 110
Ile Ile Ser Ser Ile Thr Val Gly Val Thr Gln Pro Gln Glu Val Tyr
        115                 120                 125
Met Arg Lys Asn Ala Cys Trp Leu Asn Trp Glu Asp Thr
    130                 135                 140
```

<210> SEQ ID NO 7
<211> LENGTH: 41
<212> TYPE: DNA
<213> ORGANISM: Artificial
<220> FEATURE:
<223> OTHER INFORMATION: Novel Sequence

<400> SEQUENCE: 7

```
atatggtacc atgaaatccc caaggagaac cactttgtgc c                          41
```

<210> SEQ ID NO 8
<211> LENGTH: 43
<212> TYPE: DNA
<213> ORGANISM: Artificial

-continued

```
<220> FEATURE:
<223> OTHER INFORMATION: Novel Sequence

<400> SEQUENCE: 8
atatgcggcc gcttagttga gcaacgaaga agcactggat gag                    43

<210> SEQ ID NO 9
<211> LENGTH: 36
<212> TYPE: DNA
<213> ORGANISM: Artificial
<220> FEATURE:
<223> OTHER INFORMATION: Novel Sequence

<400> SEQUENCE: 9
gatcaagctt ccatggcgtg ctgcctgagc gaggag                            36

<210> SEQ ID NO 10
<211> LENGTH: 53
<212> TYPE: DNA
<213> ORGANISM: Artificial
<220> FEATURE:
<223> OTHER INFORMATION: Novel Sequence

<400> SEQUENCE: 10
gatcggatcc ttagaacagg ccgcagtcct tcaggttcag ctgcaggatg gtg         53

<210> SEQ ID NO 11
<211> LENGTH: 20
<212> TYPE: DNA
<213> ORGANISM: Artificial
<220> FEATURE:
<223> OTHER INFORMATION: Novel Sequence

<400> SEQUENCE: 11
gcctgtctag ttgtggaagc                                              20

<210> SEQ ID NO 12
<211> LENGTH: 24
<212> TYPE: DNA
<213> ORGANISM: Artificial
<220> FEATURE:
<223> OTHER INFORMATION: Novel Sequence

<400> SEQUENCE: 12
ggtgtcctcc cagttgagcc aaca                                         24
```